(12) United States Patent
Wei et al.

(10) Patent No.: US 8,043,801 B2
(45) Date of Patent: Oct. 25, 2011

(54) METHOD OF SCREENING FOR AGENTS TO TREAT HEART FAILURE

(75) Inventors: Jeanne Y. Wei, Little Rock, AR (US); Gohar Azhar, Little Rock, AR (US); Xiaomin Zhang, Little Rock, AR (US)

(73) Assignee: Jeanne Y. Wei, Little Rock, AR (US)

( * ) Notice: Subject to any disclaimer, the term of this patent is extended or adjusted under 35 U.S.C. 154(b) by 377 days.

(21) Appl. No.: 12/313,539

(22) Filed: Nov. 22, 2008

(65) Prior Publication Data
US 2009/0187998 A1   Jul. 23, 2009

Related U.S. Application Data

(60) Provisional application No. 61/004,131, filed on Nov. 23, 2007.

(51) Int. Cl.
*C12Q 1/00* (2006.01)
*C12Q 1/68* (2006.01)
*A61K 48/00* (2006.01)
*C07H 21/04* (2006.01)

(52) U.S. Cl. ............... 435/4; 435/6; 514/44 R; 536/24.5

(58) Field of Classification Search ................... None
See application file for complete search history.

(56) References Cited

U.S. PATENT DOCUMENTS
2006/0058237 A1   3/2006  Wei

*Primary Examiner* — Doug Schultz
(74) *Attorney, Agent, or Firm* — Hugh McTavish

(57) ABSTRACT

The invention provides a method of identifying candidate agents to test for treating heart failure involving diastolic impairment, the method comprising: testing an agent to determine whether it (a) binds to serum response factor (SRF), (b) reduces SRF binding to a serum response element (SRE), or (c) reduces SRF protein levels in a cell; wherein if the agent does one or more of (a), (b), and (c), it is identified as a candidate agent.

19 Claims, 20 Drawing Sheets

Figure 15
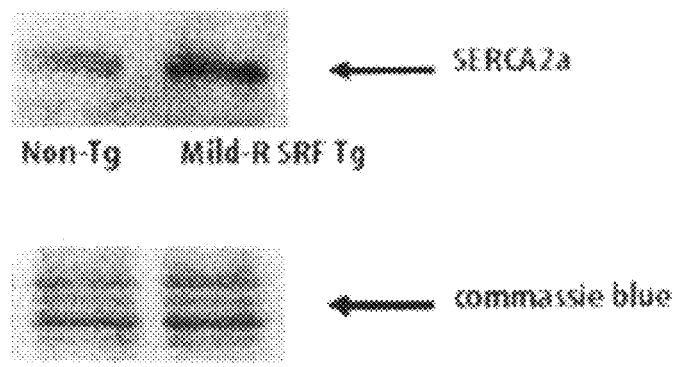
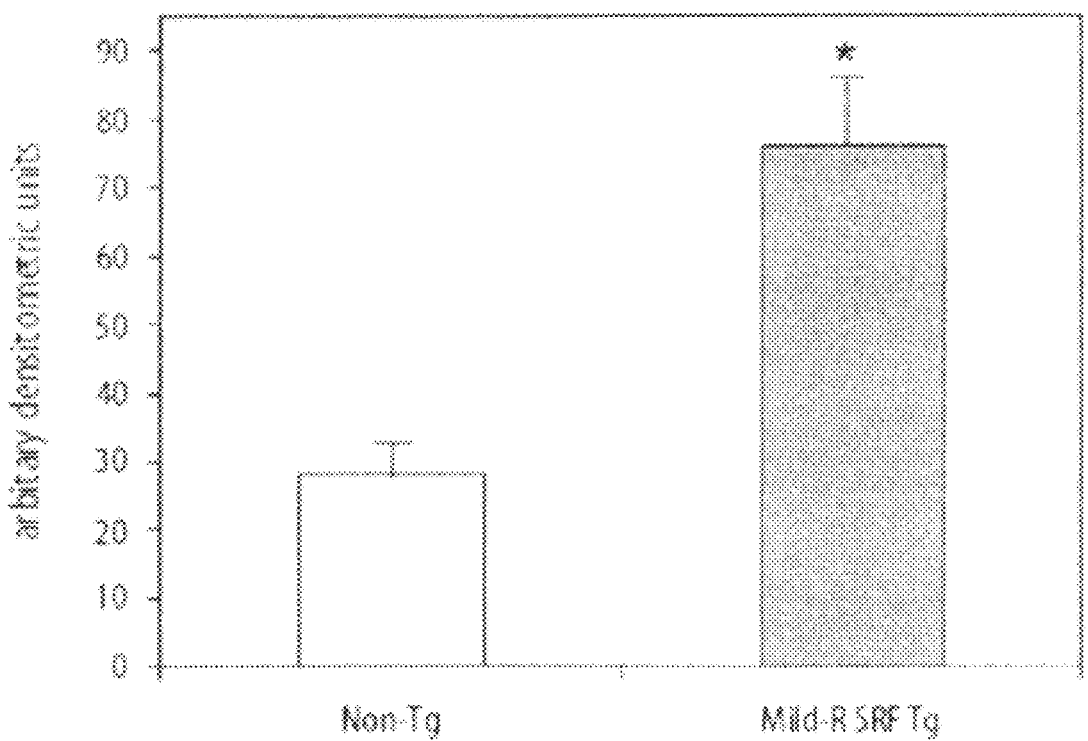

Figure 20

| | Downregulated | | Upregulated | |
|---|---|---|---|---|
| Classic CArG (56 genes) | 8430410A17Rik* | Il1f5*+ | Anxa10* | Rab8b* |
| | Aadac*+ | Jag2*+ | Aqr*+ | Serpine1*+ |
| | Akr1c6*+ | Lancl2*+ | R3hcc1*+ | Slc20a1*+ |
| | Aqp4 | LOC547428*+ | BB001228* | Tbp*+ |
| | Brca1*+ | Mup1*+ | Cyp2b10*+ | Tpm2+ |
| | C77681* | Mup2*+ | Dlg7*+ | Usp29*+ |
| | Cdca5*+ | Myh4*+ | Emp1*+ | |
| | Crk*+ | Ofa* | Emr1*+ | |
| | Cwf19l1* | Osteonectin*+ | Epb4.2*+ | |
| | Cyp3a16*+ | Pcsk5*+ | Fhl1+ | |
| | Dsc2*+ | Rrm1*+ | Hspa1b*+ | |
| | E2f3*+ | Serpina1a/b/c/d*+ | Icsbp1* | |
| | Elovl2* | Slc4a8*+ | Il4* | |
| | Es1*+ | Spink3*+ | Myh7+ | |
| | Hoxb8* | Ugt2b5*+ | Myl1*+ | |
| | Hpx*+ | Uox+ | Nppa+ | |
| | Ift81*+ | | Postn+ | |
| CArG-like (136 genes) | 1100001G20Rik* | Kcnq2* | A430107D22Rik* | Gdf15* |
| | AI042964* | Kng1* | AA222883* | Glpc1* |
| | Apc2* | Lgals2* | Acot9* | H2-DMb1* |
| | Apoa1* | Lhx8* | Acta2* | Hnedc2* |
| | Atp1a1* | Lifr* | Actn1 | Hspa1a* |
| | Bphl* | Lipc* | Apod* | Id2* |
| | Bub1* | Loc380988* | Arhgdig* | Il3a |
| | C77691* | Mug1/2* | Atf3* | Iqgap1* |
| | C8g* | Mup3* | Avpi1* | Maoa* |
| | Camk2a* | Mup5* | B4galnt1* | Ndrg4* |
| | Capn2* | Itga8 | Bdkrb1* | Rrp12* |
| | Cdh15* | Nsun2* | Bgn* | Pfkp* |
| | Cfi* | Oat* | Bmp10* | Plafl1* |
| | Cldn11* | Olfr18* | Casq1 | Ptpns1* |
| | Cpa3* | Orm1* | Ccl8* | Pus1* |
| | Csh1* | Pafah1b3* | Chx10* | Rap2ip* |
| | Cyp3a11* | Pgk2* | Col1a1* | Rho* |
| | Dcc* | Plekhh1* | Ctgf | Rps4y2* |
| | Dclre1a* | Ppil2* | Cxcl12* | Srxn1* |

Figure 20 continued

|  | | | | |
|---|---|---|---|---|
|  | Ddb1* | Prlpf* | Dnas1l2* | Tgfb3* |
|  | Ddx3x* | Pzp* | Dpp7* | Wbp5* |
|  | Defcr5* | Rpl34* | Dstn | Znrf4* |
|  | Diablo* | Rps12* | Fbln1* | |
|  | Dmrtb1* | Rps17* | | |
|  | Efnb3* | S100a9* | | |
|  | Eif2s3y* | Scg2* | | |
|  | F10* | Six3* | | |
|  | Fdft1* | Skb1* | | |
|  | Fgb* | Slc10a1* | | |
|  | Fmnl1* | Slc27a1* | | |
|  | Gabra6* | Sp4* | | |
|  | Gabrb2* | Stard10* | | |
|  | Gm1418* | Sult1a1* | | |
|  | Gm1419* | Syt3* | | |
|  | Gnmt* | Tecta* | | |
|  | Gria2* | Tesp2* | | |
|  | Gtf3c4* | Tk1* | | |
|  | H2-M10.1* | Tnfaip3* | | |
|  | Hba-x* | Trpm7* | | |
|  | Hcrt* | Tspan8* | | |
|  | Homer1* | Tyms-ps* | | |
|  | Hrc* | Ubd* | | |
|  | Il10ra* | Vax2* | | |
|  | Il15 | Vps13c* | | |
|  | Inhbc* | | | |
|  | Insm1* | | | |
| No CArG or CArG-like (9 genes) | 1500003O03Rik Arhgap9 Coasy D8Ertd738e | Hmx1 Plekha1 Plg | AV169168 Dlx5 | |
| Insuff Data (6) | Cr1 Gm106 | Igh-V Igh-VX24 | Birc1c H2-TL-T17-c | |

METHOD OF SCREENING FOR AGENTS TO TREAT HEART FAILURE

This application claims priority under 35 U.S.C. 119(e) from U.S. provisional patent application No. 61/004,131, filed Nov. 23, 2007.

STATEMENT OF GOVERNMENT SUPPORT

This work was supported in part by National Institutes of Health Grants AG-13314, AG-18388, and AG 026091, and Central Arkansas Veterans Healthcare System. The United States government may have certain rights in this invention.

BACKGROUND

Heart failure is a condition in which the heart can't pump blood the way it should. In some cases, the heart can't fill with enough blood. In other cases, the heart can't send blood to the rest of the body with enough force. Some people have both problems.

Heart failure affects at least 5 million people in the United States alone.

Heart failure can involve systolic impairment or diastolic impairment or both. In systolic dysfunction, the heart does not pump with enough force and fails to provide tissue with adequate circulatory output.

Diastolic impairment involves resistance to ventricular filling. Diastole is the period of time during which the heart is relaxed and is filling with blood. Thus, diastolic impairment involves the heart's inability to properly relax. It usually means the heart wall is stiff, and it directly relates to ventricular diastolic pressure. Diastolic impairment is generally associated with longer ventricular relaxation time.

About 20-40% of heart failure cases involve diastolic impairment.

SUMMARY

The invention involves the discovery that overexpression in cardiac tissue of a protein termed serum response factor (SRF) in mice mimics many of the symptoms seen in normal cardiac aging in humans. It also is found to mimic some symptoms of heart failure with diastolic impairment. These include (1) a higher peak A, maximal late diastolic (atrial contraction induced) transmittal flow velocity, as measured by echocardiogram; (2) a lower peak E, the maximal early transmittal flow velocity; and (3) a lower E/A ratio (ratio of peak E over peak A). The transgenic mice mildly overexpressing SRF also had increased left ventricular wall thickness.

The inventors have now found that mildly reducing expression of SRF prevents development of diastolic impairment in older normal mice. That is, normal mice have significantly decreased peak E at 15 months of age as compared to 3 months of age, and transgenic mice with mildly reduced expression of SRF do not. The transgenic mice with mildly reduced SRF expression also have thinner heart walls at 15 months of age than normal controls and maintain the ejection fraction over aging, while the normal mice have significant decrease in ejection fraction. Thus, reducing SRF expression prevents or reduces development of diastolic impairment over aging. This indicates that other compounds or agents that reduce SRF expression levels or otherwise act in a manner similar to the transgene of the transgenic mice with reduced SRF expression would be good candidate compounds or agents to test for treatment of heart failure involving diastolic impairment.

The transgenic mice with mildly reduced SRF expression expressed a transgenic mutant SRF. The mutant SRF was found to bind to wild-type SRF and to prevent SRF binding to serum response elements (SRE). The normal mice had increased SRF expression with aging, while the transgenic mice did not and therefore had approximately 3-fold lower SRF protein levels at 15 months age than normal mice at 15 months age. SRF binding to SRE enhances SRF expression, so preventing SRF binding to SRE is probably a mechanism by which the transgenic mice reduce SRF expression. It appears that the mutant SRF acts by binding to SRF, thereby preventing SRF from binding to SRE, which in turn prevents the enhancement of SRF gene transcription caused by SRF binding to SRE, and thereby mildly reduces SRF protein levels.

Therefore, any agent that (1) binds to SRF, (2) prevents SRF binding to SRE, or (3) reduces SRF protein levels in a cell, is more likely to be useful to treat heart failure involving diastolic impairment and may be considered a candidate compound to test for treating congestive heart failure.

One embodiment of the invention provides a method of identifying candidate agents to test for treating heart failure involving diastolic impairment, the method comprising: testing an agent to determine whether it (a) binds to serum response factor (SRF), (b) reduces SRF binding to a serum response element (SRE), or (c) reduces SRF protein levels in a cell; wherein if the agent does one or more of (a), (b), and (c), it is identified as a candidate agent.

Another embodiment of the invention provides a method of screening an agent for activity in treating heart failure involving diastolic impairment, the method comprising: (i) testing an agent to determine whether it (a) binds to serum response factor (SRF), (b) reduces SRF binding to a serum response element (SRE), or (c) reduces SRF protein levels in a cell; (ii) identifying a candidate agent that does one or more of (a), (b), and (c); and (iii) testing the candidate agent in a vertebrate model of heart failure with diastolic impairment to determine whether the candidate agent reduces one or more symptoms of heart failure with diastolic impairment.

One embodiment of the invention provides a method of identifying an agent for treating heart failure comprising: testing one or more candidate agents in a transgenic mammal whose cells comprise a recombinant nucleic acid encoding serum response factor (SRF) and whose cells overexpress serum response factor to identify an agent that reduces one or more symptoms of heart failure; wherein the agent that reduces one or more symptoms of heart failure (a) binds to SRF, (b) reduces SRF binding to a serum response element (SRE), or (c) reduces SRF levels in a cell.

BRIEF DESCRIPTION OF THE DRAWINGS

FIG. 15a: Representative Western blot of SERCA2 protein from hearts of 15 month old Non-Tg and Mild-R SRF Tg. n=5 in each group. Monoclonal SERCA2 antibody (Affinity Bioreagents, Golden, USA) was used. 15b: Averaged results of densitometric analysis of Western blot data from FIG. 15a. Data is representative of n=5 mice in Mild-R SRF Tg and non-transgenic group. Results are provided as means±SD, *p<0.05.

FIG. 20: List of the 207 differentially expressed genes in the 6 month old Mild-SRF Tg hearts classified on the basis of "classic CArG", "CArG-like", "No CArG or CArG-like" and "insufficient data", based on the existence of classic CArG and/or CArG-like elements in their promoter regions. Within each category, the numbers in green indicate genes that were significantly down-regulated and the numbers in red indicate genes that were up-regulated.

DETAILED DESCRIPTION

Figure 1:
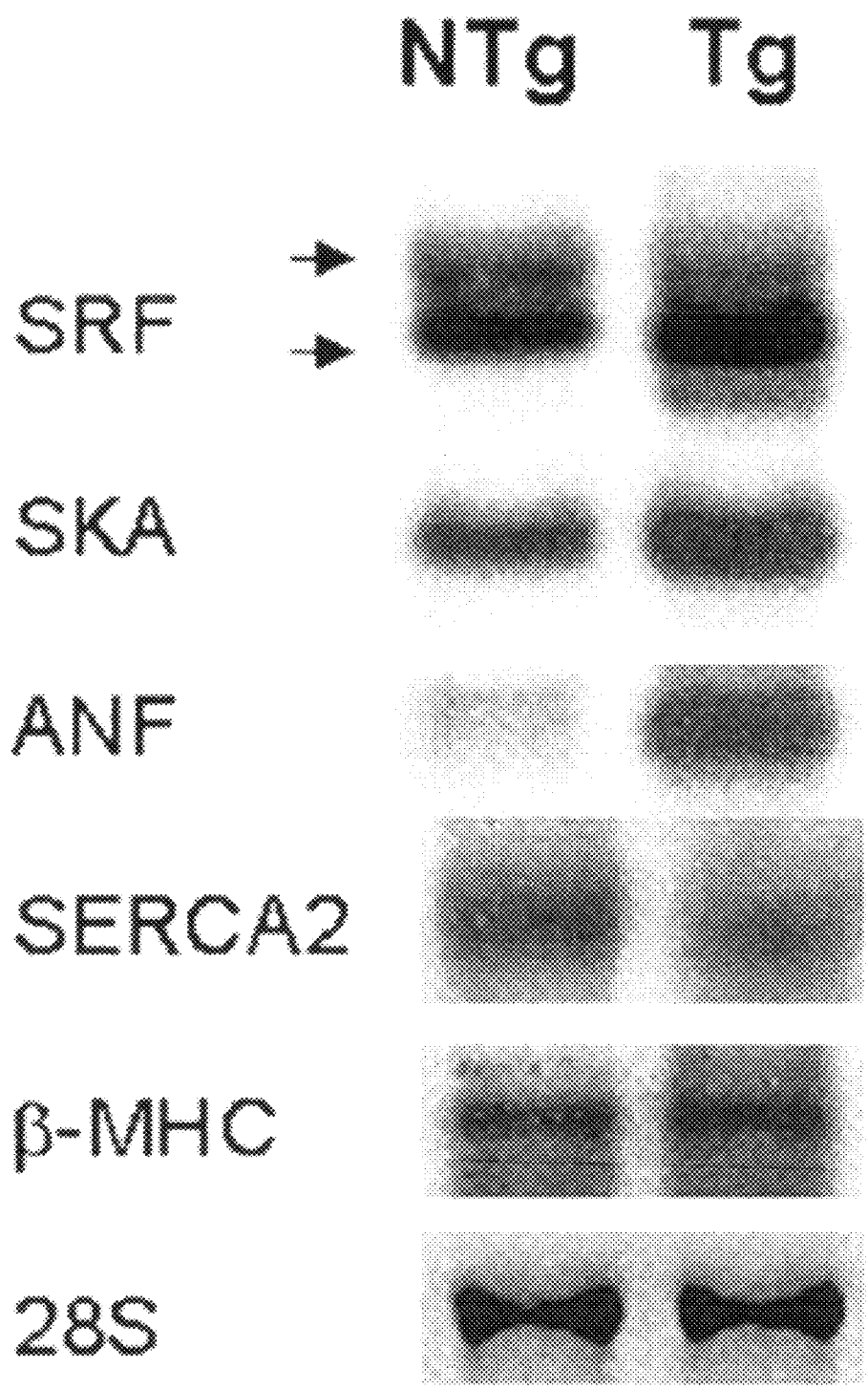
FIG. 1. mRNA levels of cardiac genes were altered in transgenic mice (Tg) compared with those of nontransgenic mice (NTg). 28S was used as a loading control. SRF, serum response factor; ANF, atrial natriuretic factor; MHC, myosin heavy chain.

Section 1 of the Example below discloses that a line of transgenic mice that mildly overexpresses SRF displays symptoms characteristic of normal cardiac aging and symptoms of heart failure with diastolic impairment. In particular, among the symptoms of diastolic impairment are (1) a higher peak A, maximal late diastolic (atrial contraction induced) transmittal flow velocity, as measured by echocardiogram; (2) a lower peak E, the maximal early transmittal flow velocity; and (3) a lower E/A ratio (ratio of peak E over peak A), well as (4) increased left ventricular wall thickness. This line of mice had a 49% increase of cardiac SRF mRNA relative to age-matched nontransgenic mice. Mice with greater expression of SRF all died within 6 months after birth (ref. 56 of Section 1 of the Example).

Section 2 of the Example below shows characterization of a line of transgenic mice expressing a mutant form of SRF that compromises the ability of SRF to bind to SRE in the promoter region of target genes. These transgenic mice expressed the mutant SRF in a cardiac-specific manner. They had mildly reduced wild-type SRF expression levels and at an elevated age did not show any of the signs of diastolic impairment seen in age-match non-transgenic mice.

By electrophoretic mobility shift assays with biotin-labeled SRE probe, it is shown in Section 2 of the Example that the mutant SRF protein prevents binding of wild-type SRF to SRE. It is believed that this is because the mutant SRF binds to wild-type SRF, and the hybrid complexes have decreased or no ability to bind to SRE. SRF is known to form oligomers, which further suggests that mutant SRF binds to wild-type SRF.

It is also shown that in 3-month-old mice, the transgenic mice expressing mutant SRF had SRF protein levels reduced by 11-12%. In 15-month-old non-transgenic mice, the SRF protein level increases 3.4 fold. But the transgenic mice have no significant increase in SRF protein levels at 15 months of age as compared to 3 months of age. Thus, the mutant SRF mildly decreases SRF levels in young mice and substantially decreases SRF protein levels in older mice.

This is evidence that an agent that decreases SRF protein levels is likely to be effective to treat heart failure involving diastolic impairment.

The evidence also indicates that an agent that reduces SRF binding to SRE is likely to be effective to treat heart failure involving diastolic impairment. Reducing SRF binding to SRE will have the effect of reducing expression of SRF itself, and affect expression of other genes transcriptionally regulated by SRF at SREs. Some of these other genes, as discussed in the Examples below, are also likely involved in defects of cardiac function with aging and in diastolic impairment.

An agent that binds to SRF is likely to have some effect on SRF oligomerization, on SRF binding to SRE, and therefore on SRF protein levels. Thus, an agent that binds to SRF is also a good candidate for testing to determine whether it treats cardiac failure involving diastolic impairment.

Whether an agent affects binding of SRF to an SRE can be tested by electrophoretic mobility shift assay as described in Section 2 of the Example below, and as described in Zhang X et al., 2001 (Early postnatal cardiac changes and premature death in transgenic mice overexpressing a mutant form of serum response factor, J Biol Chem 276(43):40033-40).

Whether an agent affects expression of SRF protein levels can be tested by western blotting of cellular extracts with labeled antibody against SRF, as described in Section 2 of the Example below.

Whether an agent binds to SRF can be tested by in vitro and in vivo interaction assays described in U.S. Pat. No. 7,211, 427. It can also be tested, for instance by coating each individual well of a multi-well plate with a distinct test compound, incubating the wells with labeled SRF, washing unbound SRF from the wells, and identifying wells containing labeled SRF. Unlabeled SRF may also be used and detected by ELISA assay using antibody against SRF.

Phage display assays may also be used to identify agents that bind to SRF.

One embodiment of the invention provides a method of identifying candidate agents to test for treating heart failure involving diastolic impairment, the method comprising: testing an agent to determine whether it (a) binds to serum response factor (SRF), (b) reduces SRF binding to a serum response element (SRE), or (c) reduces SRF protein levels in a cell; wherein if the agent does one or more of (a), (b), and (c), it is identified as a candidate agent.

Diastolic impairment may be characterized as having a reduced E/A ratio, i.e., ratio of peak early phase diastolic flow (E) over peak late phase diastolic flow (A). This may be measured by echocardiograph, as described in the Example below.

Preferably the testing to identify a candidate agent is in vitro. Testing for binding to SRF or reducing SRF binding to SRE can be in cell-free assays. Testing for reducing SRF protein levels in a cell can use cells in tissue culture in vitro.

The testing may also be in vivo, e.g., in an experimental vertebrate, such as a mouse.

In a particular embodiment, the method of identifying candidate agents comprises testing an agent to determine whether it reduces SRF protein levels in vivo in a vertebrate in heart tissue.

Various types of agents may be tested to determine whether they are candidate agents. These include small molecules, i.e., compounds with molecular weight less than 2,000. They also include larger molecular weight compounds. They also include proteins, peptides of less than 50 amino acid residues or less than 30 amino acid residues, vectors encoding mutant SRFs, such as the mutant SRF identified in Section 2 of the Example below, and vectors expressing antisense nucleic acids, for instance siRNAs, that would be expected to reduce SRF expression.

Another embodiment of the invention provides a method of screening an agent for activity in treating heart failure involving diastolic impairment, the method comprising: (i) testing an agent to determine whether it (a) binds to serum response factor (SRF), (b) reduces SRF binding to a serum response element (SRE), or (c) reduces SRF protein levels in a cell; (ii) identifying a candidate agent that does one or more of (a), (b), and (c); and (iii) testing the candidate agent in a vertebrate model of heart failure with diastolic impairment to determine whether the candidate agent reduces one or more symptoms of heart failure with diastolic impairment.

The vertebrate model of heart failure with diastolic impairment (or without diastolic impairment) may be a transgenic vertebrate that overexpresses SRF in cardiac tissue, for example the transgenic line of mice described in Section 1 of the Example herein. The vertebrate in particular embodiments may be a mammal. In more specific embodiments it is a mouse or rat. The SRF that the vertebrate overexpresses may be wild-type human SRF (SEQ ID NO:8) or the native SRF of whichever species of vertebrate is used. In particular embodiments, the SRF is at least 80% identical, at least 90% identical, or at least 95% identical to SEQ ID NO:8).

Another model of heart failure with diastolic impairment that may be used is older vertebrates displaying symptoms of diastolic impairment, for example the 15-month-old non-transgenic mice described in Section 2 of the Example.

Testing a candidate agent in a vertebrate model can involve testing to determine whether the candidate agent reduces cardiac wall thickness.

In other embodiments, testing a candidate agent in a vertebrate model can involve testing to determine whether the candidate agent increases peak E, decreases peak A, or increases the E/A ratio (as described in the Example below).

In another embodiment, testing a candidate agent in a vertebrate model can involve testing to determine whether a candidate agent increases ejection fraction.

In another embodiment, testing a candidate agent in a vertebrate model can involve testing to determine whether a candidate agent reduces diastolic blood pressure.

The invention will now be illustrated by the following Example, which is intended to illustrate the invention but not limit its scope.

EXAMPLE

Example Section 1

Mouse Model of Cardiac Aging and Heart Failure with Diastolic Impairment

Introduction

SERUM RESPONSE FACTOR (SRF) is a member of the MADS (MCM1, agamous, deficiens, SRF) family of transcriptional activators that has been implicated in the regulation of a number of genes that are important in cell proliferation and differentiation. SRF regulates its target genes by binding to the serum response element (SRE), which contains a consensus CC(A/T)GGG (CArG) motif (13, 32, 44). This cognate binding site of SRF is found in the promoter region of certain immediate-early genes and many muscle-specific genes (43, 50, 51). The level of SRF expression apparently increases during development and aging by 16-20%. In addition, the mRNA levels of a number of SRF target genes, such as atrial natriuretic factor (ANF), skeletal-actin, cardiac $\alpha$-actin, $\alpha$-myosin heavy chain ($\alpha$-MHC), and $\beta$-MHC, have been reported to undergo changes during maturational development and growth, cardiac hypertrophy, and in some instances cardiomyopathy (3, II, 12, 14). These findings suggest that SRF may also play an important role in the regulation of genes that are responsible for the maintenance of cardiac structure and function (56).

In previous studies, we observed that SRF binding activity to its cognate response sequence, the SRE, of the c-fos promoter appeared to be slightly increased in the hearts of old rats compared with young adult rats (47). Furthermore, the basal expression of SRF protein was increased by 20% in the hearts of old rats compared with young adult animals (28, 52). To pursue the significance of the increased SRF and its potential contribution to cardiac changes during aging, we previously generated transgenic mice with moderate to high levels (at least 1-fold increase compared with nontransgenic littermates) of cardiac SRF overexpression (56). These transgenic mice developed enlarged hearts with cardiomyopathy, and all died within 6 months after birth. Also, the results suggested that moderately high levels of SRF transgene overexpression correlated with earlier onset of cardiomyopathy and earlier mortality in a dose-dependent manner. However, it was unclear whether a mild increase of 20%, such as is observed during normal adult aging in the rats, or a 16% increase as observed in mice would have any effect. We therefore decided to generate transgenic mice with mild overexpression of SRF in the heart to better mimic the normal aging process. Using a previously tested DNA construct (56), we produced transgenic mouse lines with mild cardiac overexpression of SRF of 49%.

Interestingly, there were cardiac changes in the apparently healthy young adult transgenic mice at 6 mo of age that resembled those that usually occur much later (18-22 mo) during the aging process in the old mice hearts and mirrored those which have often been observed clinically in elderly individuals.

Materials and Methods

Creation of transgenic mice with mild overexpression of SRF. Two transgenic mouse lines with cardiac-specific overexpression of SRF were obtained as previously described (56). Briefly, a DNA construct that contained the -MHC promoter (a generous gift from Dr. J. Robbins, The Children's Hospital and Research Foundation, Cincinnati, Ohio) and human SRF cDNA (a generous gift from Dr. R. Prywes, Columbia University, New York, N.Y.) was constructed. It was linearized and was injected into the pronuclear stage zygotes of FVB/N mouse strain according to the standard transgenic procedure of Beth Israel Deaconess Medical Center transgenic facility. At 2-3 weeks of age, all animals had a 1-cm portion of tail removed for DNA analysis. The potential transgenic mice were screened twice by the polymerase chain reaction using two different forward primers (5'-ACAGGTGGTGAACCTGGACAC-3' (SEQ ID NO:4) and 5'-CCATTCAAGTGCACCAGGC-3' (SEQ ID NO:5)) and one reverse primer (5'-CACTGGAGTGGCAACTTCCAG-3'

(SEQ ID NO:6)). Southern blot analysis, using a [$\alpha$-$^{32}$P] dCTP-labeled SRF cDNA fragment from plasmid pCGN-SRF, was employed to confirm the identification of transgenic founder mice and to determine the transgene copy number in the transgenic mice. The studies were conducted with approval of the Institutional Review Board and are in accordance with the *Guiding Principles for Research Involving Animals and Human Beings* of the American Physiological Society. In all experiments that were performed in this study, age- and sex-matched nontransgenic littermates were used for comparison with the SRF transgenic mice.

Northern blot analysis. Total RNA was isolated from ventricular tissue using the ULTRA-SPEC RNA isolation reagent (Biotecx Laboratories, Houston, Tex.). Ten micrograms of total RNA was then fractionated on a 1% formaldehyde-agarose gel and transferred to a nylon membrane (Amersham Life Science) by capillary action in high-salt solution (10×SSC-1 mM EDTA). Blots were prehybridized in a hybridization solution containing 7% SDS, 0.5 M NaHPO4 (pH 7.2), and 200 mg/ml salmon sperm DNA for 5 h at 65° C. and followed by overnight hybridization with [$\alpha$-$^{32}$P]ATP-labeled oligonucleotide probes or [$\alpha$-$^{32}$P]dCTP-labeled SRF cDNA probe. Blots were washed three times in 2×SSC-0.2% SDS at room temperature for 30 min and then in 0.5×SSC-0.2% SDS at 65° C. for 15-30 min before exposure to X-ray film.

The sequences of the oligonucleotide probes were as follows: ANF, 5'-CCGGAAGCTGTTGCAGCCTAGTC-CACTCTGGGCTCCAATCCTGTCAATCCTACCC CCGAAGCAGCTGGA-3'(SEQ ID NO: 1); skeletal $\alpha$-actin, 5'-TGGAGCAAAACAGAATGGCTGGCTT TAATGCT-TCAAGTTTTC CATTTCCTTTCCACAGGG-3' (SEQ ID NO:2); sarcoplasmic reticulum $Ca^{2+}$-ATPase (SERCA2), 5'-TCAGTCATGCAGAGGGCTGGTAGATGTGTTGC-TAACAACGCACATGCACGCACCCGAACA-3' (SEQ ID NO:3).

A double-stranded SRF cDNA fragment from plasmid pCGNSRF was used as a probe to examine the mRNA level of SRF.

Histological analysis. After animals were killed, mouse hearts were immediately removed and placed in relaxing buffer (25 mM KCl in PBS). After treatment with relaxing buffer, the hearts were placed in 10% neutral-buffered formalin overnight. After fixing, the samples were subjected to a dehydration series and embedded in paraffin.

The atria were separated from the ventricles and then each ventricle was sectioned in 3- to 4-µm intervals from the apex upward. The sections were stained using standard hematoxylin and eosin (HE) or Masson Trichrome staining (MTS) protocols (Poly Scientific; Bayshore, N.Y.). Photomicrographs were obtained using a Nikon ES400 microscope.

Measurement of wall thickness, myocyte size, and fibrotic area. Slides of cross sections of the heart taken at the level of the left ventricular (LV) papillary muscles were stained with HE or MTS. Ventricular wall thicknesses were measured under the microscope using an objective micrometer with 0.01-mm ruler markings. The septum, LV, and right ventricular (RV) free walls were each measured at the level of the papillary muscles, and the average thickness was reported as means±SD in millimeters.

Measurement of cardiac myocyte size. Digital images of HE-stained sections of the heart were acquired at ×400 magnification with a Polaroid digital microscope camera mounted on a light microscope (Nikon). True-color image analysis was performed using Image-Pro Plus image analysis software (Media Cybernetics, Silver Spring, Md.). The slides were analyzed by two independent observers blind to the transgenic status of the mice. Ten fields from each section of the heart, LV free wall, septum, and RV free wall were chosen at random. Both endocardium and epicardial regions were included in the selection. In each one of the 10 fields, 100 cardiomyocytes with nuclear profiles were measured. Myocyte diameter was expressed as means±SD in micrometers.

To evaluate the fibrosis in the mouse myocardium, the digital images of MTS-stained cross section of the heart were captured at ×200 magnification. The true-color image analysis was performed by using the above software to quantify the collagen deposition as an indicator of fibrosis in the transgenic mice relative to that of the nontransgenic control mice. The observer performing the evaluations was blind to the transgenic status of the mice. The fibrotic areas stained blue with the MTS. A grid was applied to the monitor providing 100 intersection points superimposed on the image of muscle cells and interstitial tissue. The number of nonmuscle areas (from a possible number of 100 intersections) was expressed as a percent of the blue-staining fibrotic area. The results of the fibrotic area were reported as means±SD in square millimeters. Volume was calculated by multiplying the fibrotic area with the depth of penetration of fibrosis into the ventricular wall in serial sections of the heart from the epicardium to the endocardium. Further qualitative assessment of fibrosis was noted as either focal, diffuse, interstitial, or perivascular.

Aortic wall thickness was measured in three pairs of nontransgenic and transgenic mice. The ascending aorta used in analysis was embedded in paraffin and cut at 4-µm intervals until the aortic cusps were reached. Staining with HE and MTS was performed on two sections from the aortic root, two from the aorta proximal to the carotid bifurcation and two from the middle of the root and bifurcation of the ascending aorta. The slides of sections were imaged at ×200 magnification, and aortic wall thickness was measured at five different points of the aortic circumference using Image-Pro Plus software. The means±SD in micrometers were used in analysis.

Blood pressure measurements. Systolic blood pressure measurements were performed in conscious mice that had been acclimatized to a restrainer by the tail-cuff method (IITC Life Sciences Instruments, Woodland Hills, Calif.). Mice were placed in a temperature-controlled restrainer on a warm pad for 30 min before measurements were taken. A mean of a minimum of three readings was taken and graphed. Data were stored and analyzed using the ITTC computer software.

Echocardiography. Adult mice at 6 months of age were anesthetized with intraperitoneal injection of ketamine (50 mg/kg) and xylazine (4 mg/kg). The ventral chest was shaved, and the mouse was placed on a thermally controlled foam pad. Echocardiography was performed using a Hewlett-Packard Sonos 5500 ultrasound imaging system equipped with a 10-MHz pulsed array transducer. Electrocardiogram leads (1 front paw and 2 hind paws) were placed. Conventional two-dimensional imaging, M-mode recordings, and spectral color Doppler evaluations were performed. Cardiac size and shape were determined using M-mode and two-dimensional image recordings. The LV wall thickness, contractility, and chamber dimensions were determined at end diastole and end systole. All values were based on the average of at least three consecutive beats to minimize noise and respiratory variation. Derivative measurements included LV mass, LV volume, and systolic function. Spectral Doppler recordings of mitral inflow patterns were used for evaluation of LV diastolic filling parameters.

Data analysis. Values were expressed as means±SD. Data were analyzed by two independent observers blind to the transgenic status of the mice. Normality testing was performed on all data, and the t-test was used to determine the significance of differences between the two groups. When the data did not pass normality testing, the results were evaluated by the nonparametric Mann-Whitney U test and the equivalent Kruskall Wallis test for ANOVA. The criterion for significance was 0.05. Bonferonni correction was applied to multiple comparisons. A linear regression analysis of echocardiographic data from wild-type mice was performed with the E/A ratio as a dependent and age as an independent variable (Sigma Stat software). An R of >0.8 and a P value of 0.05 was considered significant in the regression analysis.

Results

Generation of transgenic mice with mild overexpression of SRF. On the basis of our prior observation that the severity of cardiomyopathy and premature mortality in those transgenic mouse lines correlated directly with the SRF transgene copy number and the cardiac SRF mRNA level (56), we sought to generate transgenic founder mice with a very low transgene copy number and with milder overexpression of SRF compared with the SRF transgenics with severe overexpression of SRF as reported in our previous publication (56).

After multiple microinjections were performed, the transgenic mice with mild SRF overexpression and one single transgene copy number were obtained. Northern blotting revealed that the levels of cardiac SRF mRNA were elevated (FIG. 1). Quantitation of the SRF mRNA level revealed that the transgenic mice had a mild (49%) increase of cardiac SRF mRNA relative to age-matched nontransgenic animals. These transgenic mice with 49% SRF overexpression had the lowest level of SRF overexpression among all the SRF transgenic mouse lines that have been produced to date in our laboratory (56).

Changes in gene expression in transgenic mice. Changes in cardiac gene expression were observed in transgenic mice, which included a 50% increase in skeletal α-actin (SKA), a 400% increase in ANF, a 10% increase in β-MHC, and a 50% decrease in SERCA2 compared with the nontransgenic mice (FIG. 1).

Figure 2:
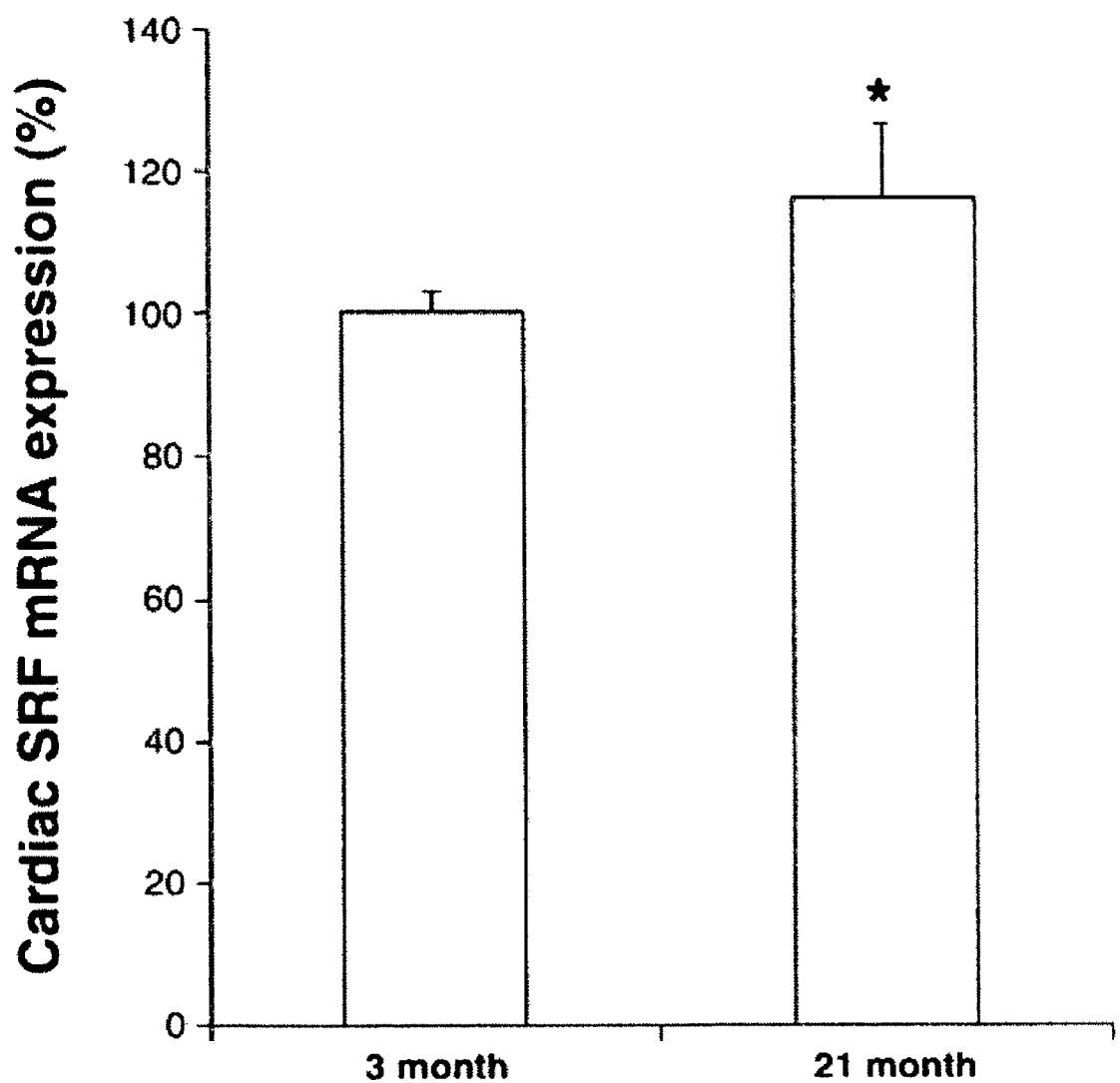
FIG. 2. mRNA expression of SRF in 3- and 21-mo-old mouse hearts at baseline. Hearts are from wild-type mice. Hearts of older animals have a 16% greater SRF mRNA expression compared with young (*$P<0.05$, n=4) mice.

SRF expression in young and old nontransgenic mice. We also evaluated the expression of SRF mRNA in 3- and 21-month-old wild-type mice and found that the 21-month-old mice had 16% greater SRF mRNA expression compared with the 3-month-old (FIG. 2, $P<0.05$) mice.

Figure 3:
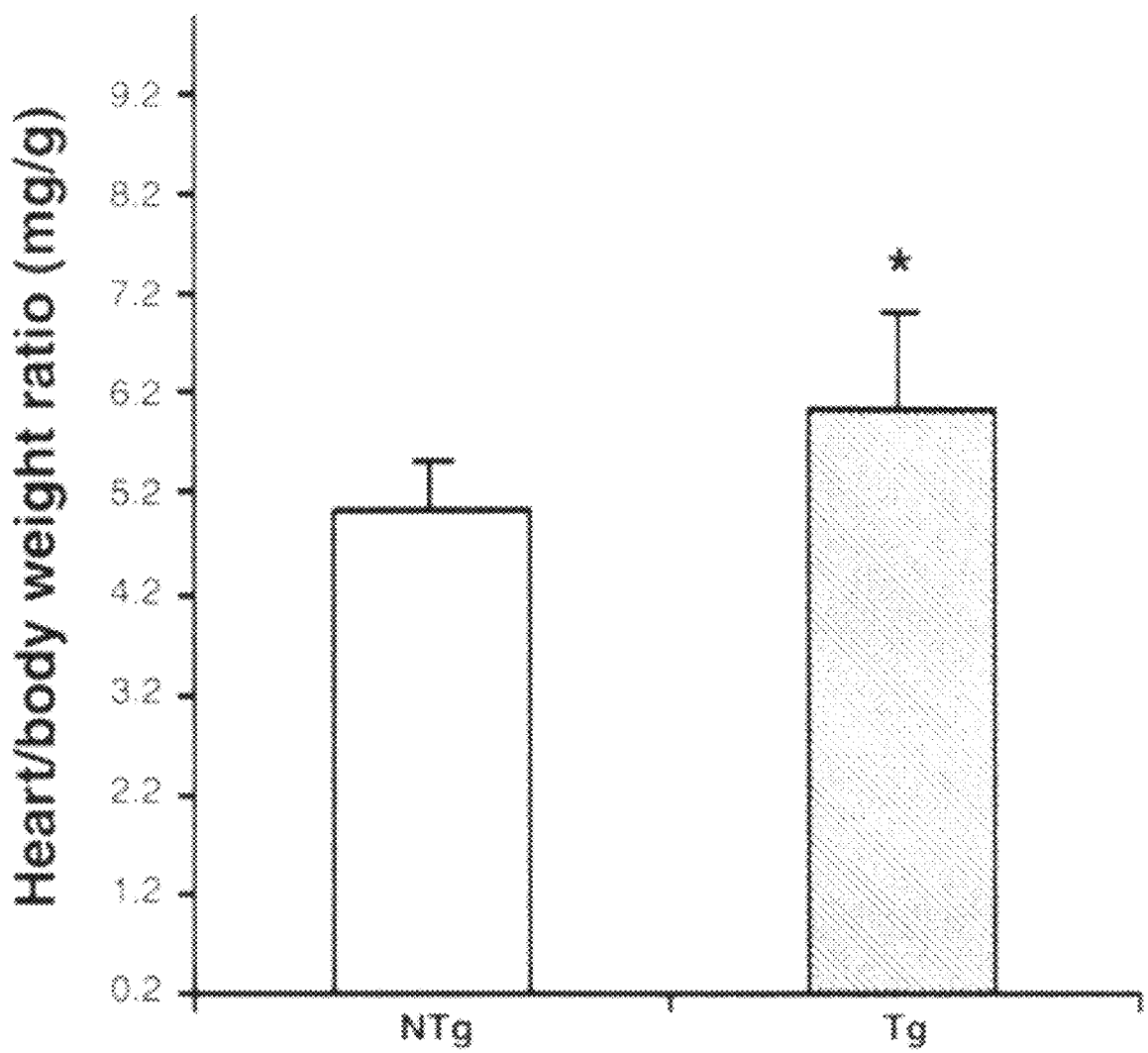
FIG. 3. Heart weight (mg)-to-body weight (g) ratio was slightly increased in Tg (6.03±1.0) vs. NTg (5.03+0.5, n=8, *$P<0.05$). Actual heart and body weights were used in the determination of the ratio.
Figure 4:
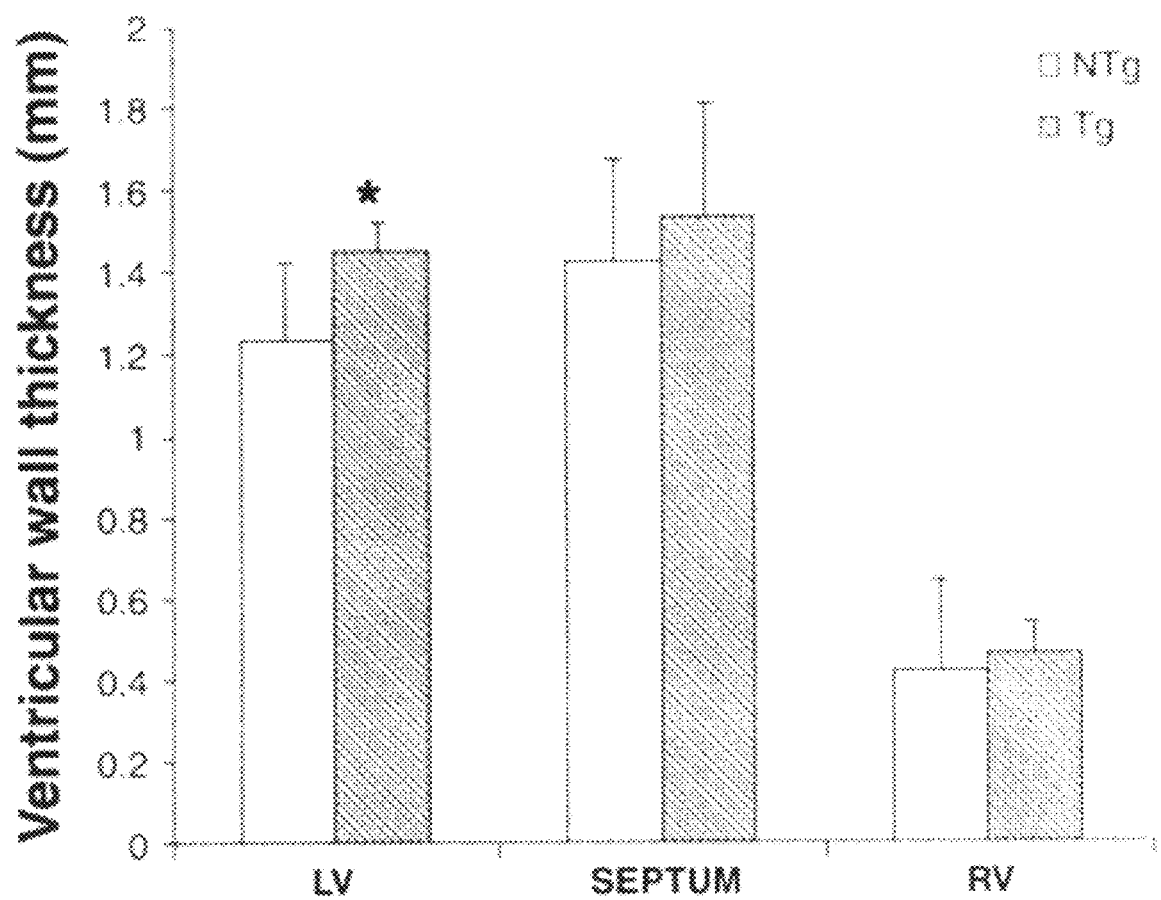
FIG. 4. Ventricular wall thickness. Left ventricle (LV) was 1.45 mm in Tg, whereas it was 1.23 mm in NTg (n=5, *P<0.05). Septum was 1.53 mm in Tg, whereas it was 1.42 mm in NTg [n=5, not significant (NS)]. Right ventricle (RV) was 0.46 mm in Tg, whereas it was 0.42 mm in NTg (n=5, NS).
Figure 5:
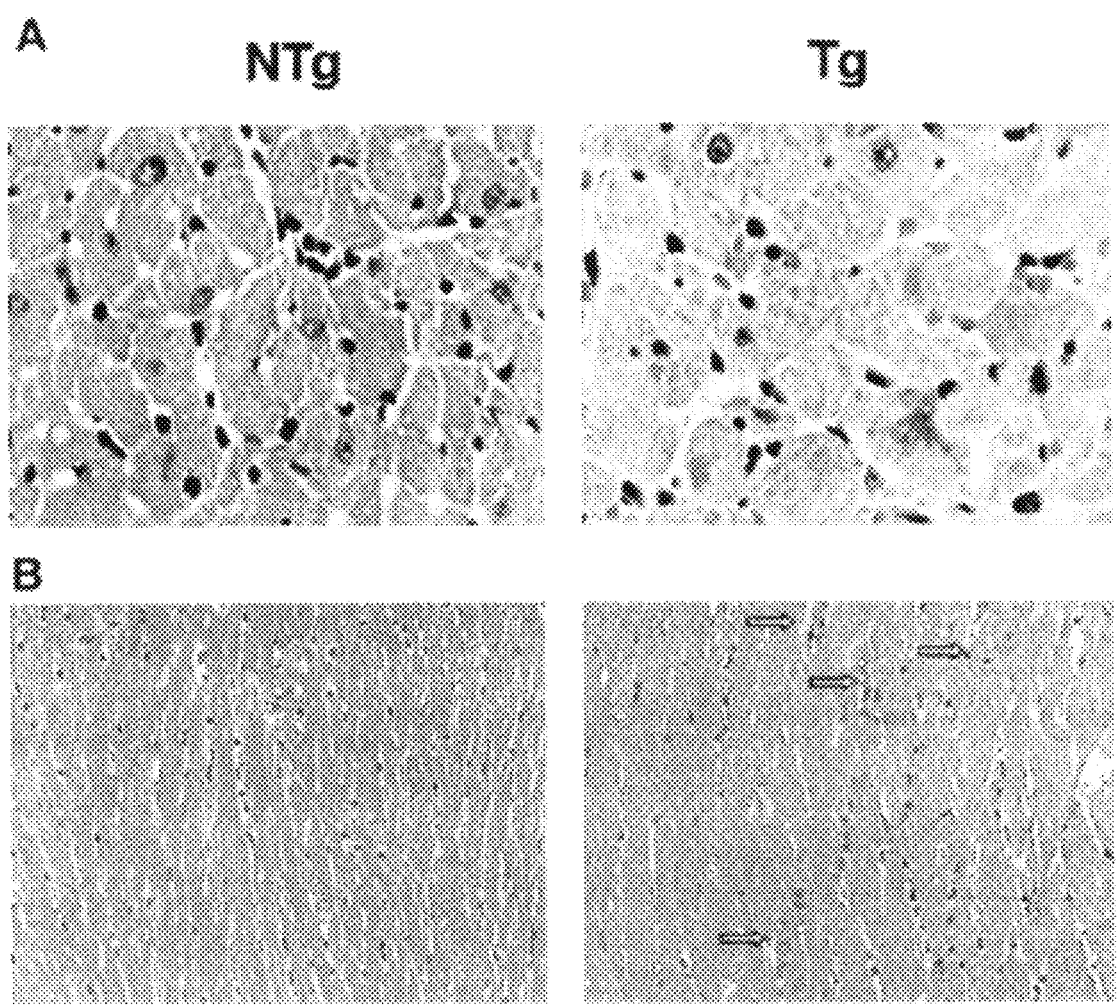
FIG. 5. Histological examination of hearts from NTg and Tg. A: cross section of the heart showing hematoxylin and eosin (HE) staining of cardiac myocytes of NTg and Tg (magnification of ×400). B: longitudinal section of the heart with Masson Trichrome staining of NTg and Tg (magnification of ×200). Interstitial fibrosis was present in the Tg heart (arrows).
Figure 6:
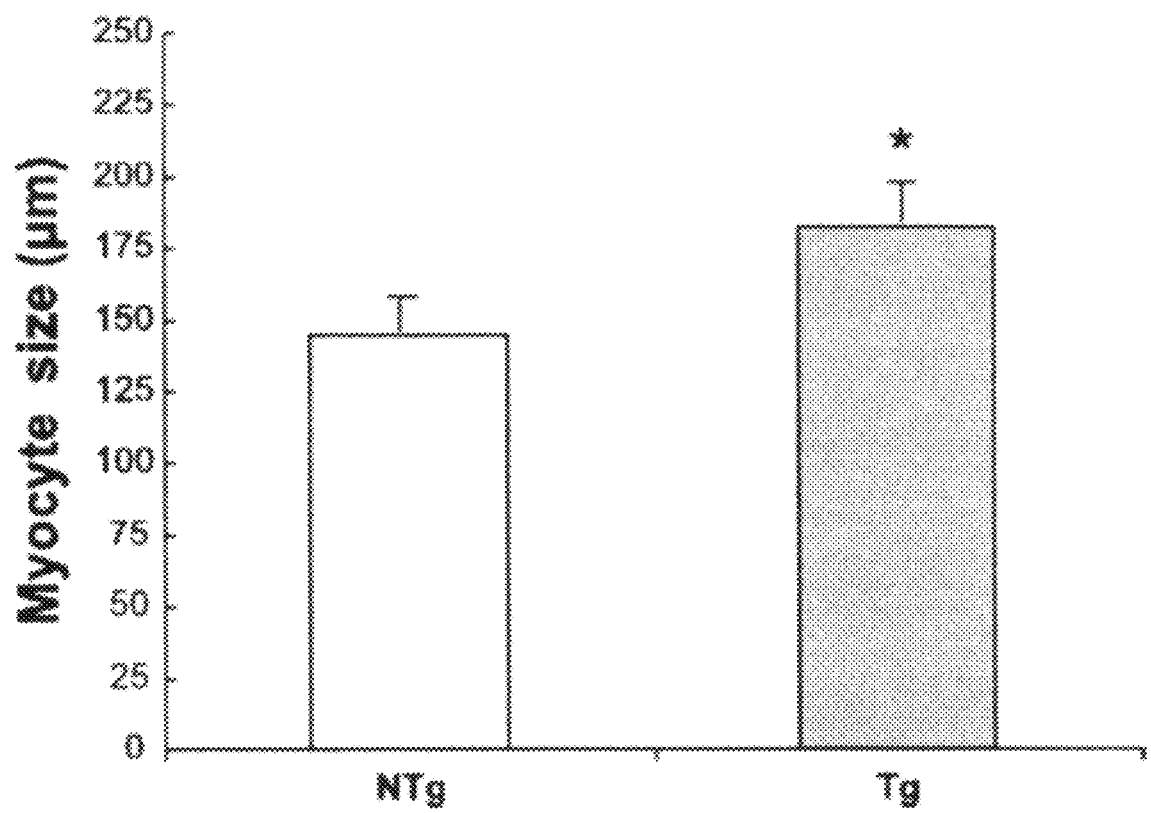
FIG. 6. Average diameter of cardiomyocytes of Tg (182±13 μm) was larger than that of NTg (145±8 μm, n=100, *P<0.001).

Cardiac morphological changes in transgenic mice. There were no obvious differences between the transgenic and non-transgenic mouse hearts at 6 months of age. However, the heart weight-to-body weight ratio was slightly increased in transgenic (6.03±1.0) compared with nontransgenic (5.03±0.5, n=8, $P<0.05$) mice (FIG. 3). Measurement of ventricular wall thickness in the fixed sections using a micrometer under light microscopy revealed a slight increase of wall thickness in transgenic [17% increase in LV, n=5, $P<0.05$; 7.7% increase in septum, n=5, not significant (NS); and 9.5% increase in RV, n=5, NS, respectively] relative to nontransgenic mice (FIG. 4). The cardiac myocytes of the transgenic mice were heterogeneous in size, but most cells appeared to be larger in size than those of age-matched nontransgenic littermates (FIG. 5A). Measurement of the average cell size of cardiac myocytes, based on the cross-sectional diameter of the cardiomyocytes (FIG. 6), revealed a 12% increase in transgenic relative to nontransgenic mice (n=1,000, $P<0.001$).

There was an increase in the collagen deposition of 6.7% (NS) observed in the hearts of the transgenic relative to the nontransgenic mice (FIG. 5B). The volume percentage of collagen increase in the transgenic mice was 6.7% more than that of the nontransgenic (NS). Collagen deposition was diffuse interstitial and present mainly in the epicardial region.

Aortic wall thickness as measured in age-matched (6-month-old) nontransgenic mice was 173±35 μm (n=3) and in transgenic mice was 168±57 μm (n=3). There was no significant difference between the two groups in the aortic wall thickness.

Cardiac morphological changes in 3-month-old vs. 21-month-old nontransgenic mice demonstrated a difference in morphology that was similar to that of the 6-month-old nontransgenic compared with the age-matched transgenic mouse. Although the aging changes were more advanced in the hearts of 21-month-old nontransgenic mice compared with those of the 6-mo-old transgenic mice, the trend was similar.

The heart weight-to-body weight ratio of the 3-month-old nontransgenic was 3.7±0.5 compared with 5.6±0.8 in the 21-month-old (n=3, $P<0.05$) mice. Measurement of LV wall thickness showed a 24% increase (n=3, $P<0.05$) in 21-month-old relative to 3-month-old mice.

Measurement of the average cell size of cardiac myocytes, as based on the cross-sectional diameter of the cardiomyocytes, revealed an 18% increase in the 21-month-old relative to that in 3-mo-old mice (n=1,000, $P<0.001$). The volume of fibrosis in the 21-month-old mice was 14% greater than that in the 3-month-old mice.

Functional assessment. Systolic blood pressure, as measured by the tail-cuff method in the conscious mice, did not demonstrate any significant difference, with the 6-month-old nontransgenic mice having a blood pressure of 123±12 mmHg and the age-matched transgenic mice having that of 126±18 mmHg.

Detailed evaluation of in vivo cardiac structure and function was performed using echocardiographic imaging and Doppler flow assessment techniques. The chamber dimensions were measured, and the derived calculations of LV mass and volume as well as fractional shortening and relative wall thickness were made to gain a better characterization of the physiological consequences of mild cardiac specific overexpression of the SRF gene. LV diastolic filling parameters were also determined. As shown in Table 1, there was no difference between nontransgenic and transgenic F1 young adult animals at the age of 6 months in terms of body weight or estimated LV mass.

TABLE 1

Echocardiagraphic findings.

|  | Non-Tg | Tg | P value |
|---|---|---|---|
| Body weight, g | 30 ± 4.9 | 29 ± 4.5 | NS |
| Mass, g | 0.12 ± 0.031 | 0.12 ± 0.030 | NS |
| PWd, mm | 0.83 ± 0.15 | 0.97 ± 0.13 | NS |
| PWs, mm | 1.36 ± 0.24 | 1.51 ± 0.07 | NS |
| AWd, mm | 0.86 ± 0.17 | 1.01 ± 0.16 | NS |
| AWs, mm | 1.33 ± 0.22 | 1.44 ± 0.16 | NS |
| LVDd, mm | 3.90 ± 0.34 | 3.30 ± 0.24 | <0.01 |
| LVDs, mm | 2.31 ± 0.36 | 1.74 ± 0.24 | <0.01 |
| EFS, % | 41.00 ± 9.43 | 48.0 ± 4.64 | NS |
| epi-D, mm | 5.59 ± 0.366 | 5.27 ± 0.39 | <0.05 |
| epi-V, μl | 176.53 ± 35.85 | 149.15 ± 33.03 | <0.05 |
| Vold, μl | 60.70 ± 15.56 | 36.48 ± 7.60 | <0.01 |
| Vols, μl | 13.18 ± 6.22 | 5.53 ± 2.35 | <0.01 |
| RWth | 0.43 ± 0.10 | 0.59 ± 0.08 | <0.01 |
| SV, μl/beat | 47.52 ± 15.99 | 30.95 ± 6.07 | <0.01 |
| CI, μl/min$^{-1}$/gm$^{-1}$ | 379.08 ± 124.11 | 294.85 ± 53.21 | NS |
| Peak E, m/s | 0.63 ± 0.105 | 0.51 ± 0.08 | <0.01 |

TABLE 1-continued

Echocardiagraphic findings.

| | Non-Tg | Tg | P value |
|---|---|---|---|
| Peak A, m/s | 0.22 ± 0.05 | 0.27 ± 0.06 | NS |
| E/A | 2.79 ± 0.93 | 1.84 ± 0.31 | <0.05 |

Values are expressed as means ± SE; n = 10 mice. PWd, posterior wall thickness (diastolic); PWs, posterior wall thickness (systolic); AWd, anterior wall thickness (diastolic); AWs, anterior wall thickness (systolic); LVDd, left ventricular diastolic dimension; LVDs, left ventricular systolic dimension; EFS (%), endocardial fractional shortening; epi-D, epicardial dimension; epi-V, epicardial volume; Vold, end diastolic volume; Vols, end systolic volume; RWth, relative wall thickness; SV, stroke volume; CI, cardiac index; Peak E, maximal early diastolic transmitral flow velocity; Peak A, maximal late diastolic (atrial contraction induced) transmitral flow velocity; E/A, Peak E/Peak A ratio; NS, not significant.

Evaluation of LV performance revealed that compared with age-matched nontransgenic mice, the young adult transgenic mice at 6 months of age displayed characteristic cardiac functional changes resembling those that are usually observed much later in life in the aged human heart. The changes in the young adult transgenic mice included slightly increased diastolic posterior wall thickness, as well as significantly decreased LV diastolic and systolic dimensions (P<0.01, and P<0.01, respectively). Along with the changes observed above, the end-diastolic and end-systolic volumes were also decreased, whereas the relative wall thickness was increased in the young adult transgenic compared with non-transgenic littermates (P<0.01, P<0.01, and P<0.01, respectively). Also, the parameters of pumping capacity such as stroke volume (ml/beat) decreased in transgenic compared with nontransgenic animals (P<0.01). Significant differences were also observed between the transgenic and nontransgenic animals in the peak E wave and E/A ratio (P<0.01 and P<0.05, respectively).

These findings demonstrate that in young adult transgenic mice with mild SRF overexpression, there was evidence of mildly altered cardiac systolic and diastolic dimensions and function in terms of reduced LV stroke volume, as well as slightly delayed LV filling. However, there was no evidence of clinically significant cardiac hypertrophy, cardiac dysfunction, and/or congestive heart failure.

Figure 7:
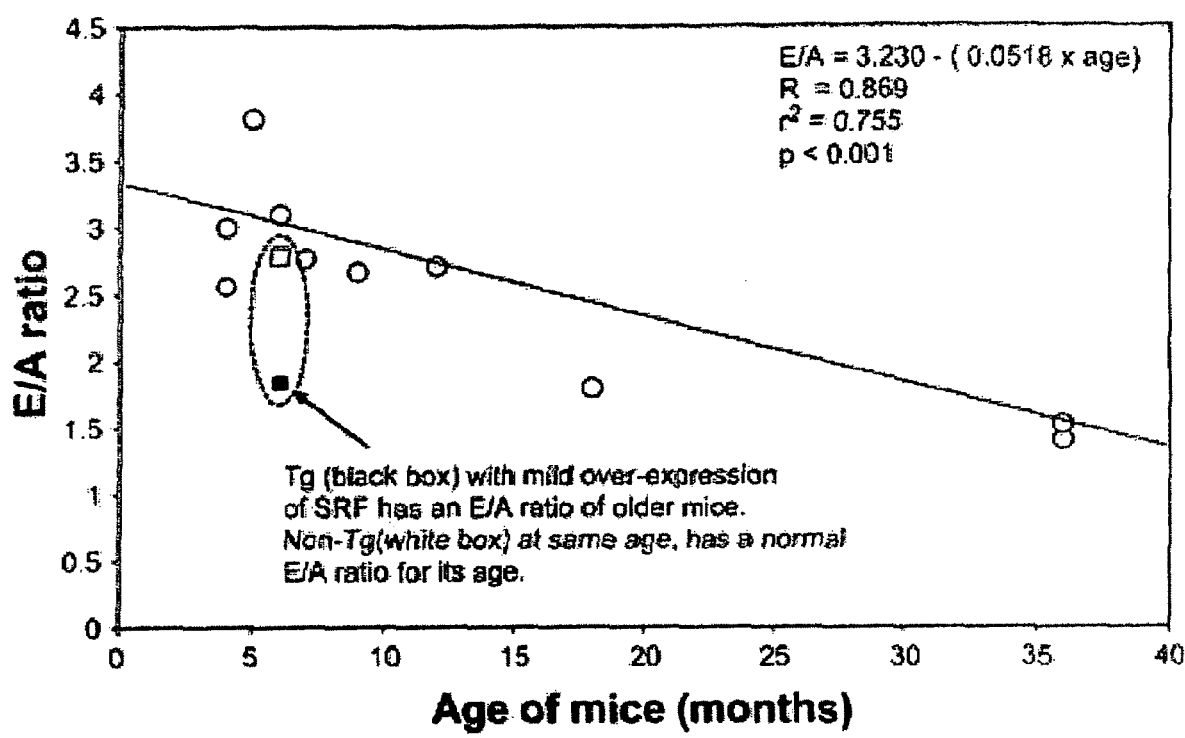
FIG. 7. E/A ratios of healthy wild-type mice at different ages. Data from the Tg mice and NTg littermates are depicted within the oval outline. SRF Tg mice (■) had an E/A ratio resembling that of the old mice. NTg littermate (□) mice had an E/A ratio that was normal for their age as depicted in the linear regression. E/A ratios from all mice except the SRF Tg were used in the regression analysis. R=0.869, $r^2$=0.755, and P<0.001.

To confirm that the E/A ratio in the young adult transgenic mice was similar to that of older wild-type mice, we used the echocardiographic data from wild-type mice at different ages to perform a linear regression analysis of E/A ratio with age using Sigma Stat software. Our results demonstrated a significant association of E/A ratio with age, with an R of 0.869 and a P<0.001 (FIG. 7). Interestingly, the hearts of 6-month-old transgenic mice had an E/A ratio that matched that of older wild-type mice.

Discussion

The major findings in the present study are that mild cardiac overexpression of SRF is associated with slightly increased relative wall thickness and decreased LV volumes in young adult transgenic mice. It is also associated with increased LV stiffness, with reduced early diastolic LV filling (peak E) and increased late diastolic filling (peak A). The observed changes in LV function, including the reduced E/A ratio, are similar to those that have often been observed during adult mammalian aging (18, 19, 22-24, 41).

Aging is a complex biological process associated with a progressive decline in the physiological and biochemical performance of individual tissues and organs, leading to increased susceptibility to age-associated disease and functional senescence (26, 37, 54, 55). Multiple factors are likely involved in this life-long process. However, it is plausible that changes in a single gene level could potentially result in certain changes and/or syndromes that mimic aspects of accelerated aging, as has been observed with the mutations in the Werner's, Bloom's, and Ataxia-Telangiectasia genes (25, 30, 31, 33). Recently, a few mouse models with phenotypes that resemble various aspects of aging have been created. For example, defects in the klotho gene cause mice to die prematurely with a number of disorders commonly found in elderly people, such as arteriosclerosis, osteoporosis, skin atrophy, and emphysema (21). Targeted mutations in the first six exons of the p53 gene in the mouse can result in reduced life span, osteoporosis, generalized organ atrophy, and/or diminished stress tolerance. In addition, transgenic overexpression of a truncated form of the p53 gene results in an aging phenotype that is similar to that which has been observed in the p53 knockout mice (53). Delineation of the role of important transcription factors in the aging process using transgenic or gene-targeting approaches could significantly enrich our understanding of the process of normal adult aging.

The efforts of our laboratory have focused on understanding the mechanisms of cardiac aging. The present study indicates that it is feasible to create a transgenic mouse model with changes in cardiac function and morphology resembling those of normal adult aging by mild cardiac-specific overexpression of an important transcription factor such as SRF. We have shown that SRF expression in mice increased by 16% from 3 to 21 mo of age, which suggested to us that the level of overexpression of SRF in a transgenic mouse model needed be relatively low to mimic the aging process. We therefore generated the SRF transgenic mice with only one copy number of SRF transgene that overexpressed SRF in the heart by 49% vs. the nontransgenic control mice.

Aging of the heart is associated with a number of morphological and functional changes (2, 37, 38, 46). These age-related alterations show variability among rats, mice, and other species studied. In humans too, there is a range of cardiac changes that might occur with normal aging in the heart. In the absence of disease, aging may alter cardiac function during both systole and diastole, especially a reduction in the early LV diastolic filling (16, 37, 46). However, these changes are usually "mild" and without clinical significance in the majority of elderly who are free of cardiac diseases; therefore, they may be referred to as part of "normal cardiac aging" (17, 37, 46). Nevertheless, age-related changes in the heart in the absence of overt clinical disease predispose the heart to develop pathological changes. These changes also reduce the reserve capacity of the heart and make it more vulnerable to injury.

Most components of the cardiovascular system undergo some degree of change with aging, and various morphological alterations have been attributed to aging (22, 38). The myocardium in older individuals is characterized by a loss of myocytes with subsequent hypertrophy of the remaining viable myocytes. Ventricular mass is usually preserved or may be slightly increased. Those surviving myocytes may contain multiple nuclei and increased copies of chromosomes (polyploidy). As myocytes are lost and fibroblasts continue to proliferate and produce collagen, the physical properties of the aging heart become altered (16, 34, 37, 45). The histological changes observed in the hearts of the transgenic mice in the present study included cardiomyocyte hypertrophy and slight interstitial fi-brosis and LV wall thickness, which indicate that these transgenic mice had some morphological features resembling cardiac aging. The morphological changes seen in the transgenic mice in our studies were not as marked as those seen in the studies of Anversa and colleagues (Olivetti et al., Ref. 34), which showed a 60% increase in myocyte size and a 22% increase in collagen content in the old rat hearts. However, we believe that the results of Anversa and colleagues are representative of the extreme end of aging in rats, whereas ours represent an earlier phase of aging in otherwise healthy, young adult mouse hearts.

Interestingly, the echocardiographic changes observed in the young adult transgenic mice with mild SRF overexpression at 6 mo of age mirrored those that have been observed in older mice and also in elderly persons. For the majority of older individuals who are free of clinically significant cardiac disease, the aging heart adapts and performs its required functions fairly well in the basal state (9, 23, 37). However, certain cardiac changes have been observed in the healthy elderly, which include increased LV end-diastolic relative wall thickness, decreased early diastolic filling, increased duration of myocardial relaxation, increased myocardial stiffness, decreased responsiveness to P-adrenergic agonists, decreased arterial compliance, decreased maximum aerobic capacity, and decreased baroreceptor reflex sensitivity (37, 39).

The prolonged contraction duration and myocardial relaxation phase observed in the heart of the older mammal is partly due to prolonged calcium entry during an extended sarcolemmal depolarization, as well as decreased velocity of calcium uptake from the sarcoplasmic reticulum after depolarization. Age-related decreases in the activity of the sarcoplasmic reticulum pump (ATPase) are correlated with age-associated changes in SERCA2 gene expression (4, 27, 37). The SRE is in the promoter region of SERCA2. SRF binds to SRE and regulates the expression of SERCA2 gene (6). In the present study, we demonstrated that mild overexpression of SRF resulted in downregulation of cardiac SERCA2 mRNA in the transgenic mice. This finding supports the notion that the mildly increased SRF that has been observed in the heart of the older animal (28, 52) might contribute to the age-associated decrease of SERCA2 level in senescence and thereby also contribute to the age-associated prolongation of cardiac relaxation.

The increase in the expression level of ANF and skeletal actin in our transgenic mouse model in this project parallels the increase seen in these genes in other cardiac hypertrophic conditions in which reexpression of the fetal gene program occurs (22). The increase in -MHC observed in our transgenic mouse is also similar to that observed during normal cardiac aging (37).

The combination of prolonged cardiac relaxation and increased myocardial stiffness during adult aging may result in an elevated LV end-diastolic pressure at rest and with exertion (1, 5). This has also been associated with the characteristic finding of decreased early diastolic filling in elderly individuals. Because early diastolic filling is reduced, there is consequently relatively more filling during late diastole in old compared with younger individuals. These changes are demonstrated on Doppler echocardiography as a change in the ratio of E/A ratio (7, 37). A long-term follow-up study has reported that E/A ratio changes during aging and drops more than one-half from the 30s to the 80s during a person's lifetime (9). It has been considered that the E/A ratio is a sensitive and important indicator of cardiac aging (8-10, 15-17, 20, 29, 35, 36, 38, 40, 46, 48, 49). In the current study, the young adult transgenic mice had a 20% decline in peak E and a 35% decrease in the E/A ratio relative to the nontransgenic mice. Our result of an E/A ratio of 1.84±0.31 is larger than the E/A ratio of 1.55±0.07 reported by Taffet et al. (46). However, the mice used in the study by Taffet et al. were significantly older (32 mo), and it is likely that transgenic mice at a slightly older age than 6 mo (perhaps 9-11 mo) would have had a lower E/A ratio. A linear regression analysis of E/A ratios of other healthy wild-type mice of different ages performed in our laboratory demonstrates a significant correlation between E/A ratio and age, with an R of 0.869 and a P<0.001 (FIG. 7). In addition, the E/A values of the older wild-type mice in the current study (age 36 mo) are in agreement with those reported by other observers (10, 16, 20, 40, 46, 48).

When diastolic dysfunction is present, a greater portion of end-diastolic volume is the result of late filling rather than early filling. Thus the E/A ratio is reduced in diastolic dysfunction. Thus, a reduced E/A ratio is also characteristic of diastolic impairment.

In summary, aging is a process that spans many decades in human beings and, similarly, many months in rodents. To translate human cardiac aging with a much longer life span into rodent years may be fraught with complexities. However, in general, aging might be arbitrarily divided into an earlier phase (humans between 50 and 60 years and in rodents between 10 and 17 months), a middle phase (humans between 61 and 80 years and in rodents between 18 and 24 months), and a late phase (humans between 81 and 100 years and in rodents between 25 and 32 months). Of course, with the progressively changing demographics and aging of the population, these arbitrary divisions of what might be considered "early" or "late" aging will likely undergo revision and change. Currently, the most consistently characteristic change studied in individuals in the mid-phase of aging is the reduced cardiac E/A ratio. Our transgenic mice at a chronological age of 6 months demonstrate this E/A reduction. Hence, the findings from the present study suggest that the age-associated increase in SRF expression that has been observed in rodents has functional significance and likely contributes to the changes considered to be characteristic of the aging heart. The cardiac-specific overexpression of SRF at a low level has resulted in the creation of a mouse model of myocardial aging, with an "old heart" in a young adult body. This model could potentially help to further elucidate the molecular mechanisms of human cardiac aging.

References Cited

1. Ambrose J A, Teichholz L E, Meller J, Weintraub W, Pichard A D, Smith H Jr, Martinez E E, and Herman M V. The influence of left ventricular late diastolic filling on the A wave of the left ventricular pressure trace. *Circulation* 60: 510-519, 1979.
2. Anversa P and Nadal-Ginard B. Myocyte renewal and ventricular remodelling. *Nature* 415: 240-243, 2002.
3. Argentin S, Ardati A, Tremblay S, Lihrmann I, Robitaille L, Drouin J, and Nemer M. Developmental stage-specific regulation of atrial natriuretic factor gene transcription in cardiac cells. *Mol Cell Biol* 14: 777-790, 1994.
4. Assayag P, Charlemagne D, de Leiris J, Boucher F, Valere P E, Lortet S, Swynghedauw B, and Besse S. Senescent heart compared with pressure overload-induced hypertrophy. *Hypertension* 29: 15-21, 1997.
5. Bak M I, Wei J Y, and Ingwall J S. Interaction of hypoxia and aging in the heart: analysis of high energy phosphate content. *J Mol Cell Cardiol* 30: 661-672, 1998.
6. Baker D L, Dave V, Reed T, Misra S, and Periasamy M. A novel E box/AT-rich element is required for muscle-specific expression of the sarcoplasmic reticulum $Ca^{2+}$-ATPase (SERCA2) gene. *Nucleic Acids Res* 26: 1092-1098, 1998.
7. Bella J N, Palmieri V, Roman M J, Liu J E, Welty T K, Lee E T, Fabsitz R R, Howard B V, and Devereux R B. Mitral ratio of peak early to late diastolic filling velocity as a predictor of mortality in middle-aged and elderly adults: the Strong Heart Study. *Circulation* 105: 1928-1933, 2002.
8. Benjamin E J, Levy D, Anderson K M, Wolf P A, Plehn J F, Evans J C, Comai K, Fuller D L, and Sutton M S. Determinants of Doppler indexes of left ventricular diastolic function in normal subjects (the Framingham Heart Study). *Am J Cardiol* 70: 508-515, 1992.

9. Besse S, Delcayre C, Chevalier B, Hardouin S, Heymes C, Bourgeois F, Moalic J M, and Swynghedauw B. Is the senescent heart overloaded and already failing? *Cardiovasc Drugs Ther* 8: 581-587, 1994.

10. Brenner D A, Apstein C S, and Saupe K W. Exercise training attenuates age-associated diastolic dysfunction in rats. *Circulation* 104: 221-226, 2001.

11. Chien R. Signaling mechanisms for the activation of an embryonic gene program during the hypertrophy of cardiac ventricular muscle. *Basic Res Cardiol* 87: 49-58, 1992.

12. Colucci W S. Molecular and cellular mechanisms of myocardial failure. *Am J Cardiol* 80: 15L-25L, 1997.

13. Ding W, Witte M M, and Scott R E. Transformation blocks differentiation-induced inhibition of serum response factor interactions with serum response elements. *Cancer Res* 59: 3795-3802, 1999.

14. Durand J B. Genetic basis of cardiomyopathy. *Curr Opin Cardiol* 14: 225-229, 1999.

15. Eysmann S B, Douglas P S, Katz S E, Sarkarti M, and Wei J Y. Left ventricular mass and diastolic filling patterns in quad-riplegia and implications for effects of normal aging on the heart. *Am J Cardiol* 75: 201-203, 1995.

16. Forman D E, Cittadini A, Azhar G, Douglas P S, and Wei J Y. Cardiac morphology and function in senescent rats: gender-related differences. *J Am Coll Cardiol* 30: 1872-1877, 1997.

17. Forman D E, Manning W J, Hauser R, Gervino E V, Evans W J, and Wei J Y. Enhanced left ventricular diastolic filling associated with long-term endurance training. *J Gerontol* 47: M56-M58, 1992.

18. Grandi A M, Venco A, Barzizza F, Scalise F, Pantaleo P, and Finardi G. Influence of age and sex on left ventricular anatomy and function in normals. *Cardiology* 81: 8-13, 1992.

19. Grodzicki T and Messerli F H. The heart in the hypertensive elderly. *J Hum Hypertens* 12: 593-597, 1998.

20. Knollmann B C, Blatt S A, Horton K, de Freitas F, Miller T, Bell M, Housmans P R, Weissman N J, Morad M, and Potter J D. Inotropic stimulation induces cardiac dysfunction in transgenic mice expressing a troponin T (179N) mutation linked to familial hypertrophic cardiomyopathy. *J Biol Chem* 276: 10039-10048, 2001.

21. Kuro-o M. Disease model: human aging. *Trends Mol Med* 7: 179-181, 2001.

22. Lakatta E G. Cardiovascular aging in health. *Clin Geriatr Med* 16: 419-444, 2000.

23. Lakatta E G. Changes in cardiovascular function with aging. *Eur Heart J* 11, Suppl C: 22-29, 1990.

24. Lakatta E G and Sollott S J. Perspectives on mammalian cardiovascular aging: humans to molecules. *Comp Biochem Physiol A* 132: 699-721, 2002.

25. Land S C and Collett A. Detection of Cl$^-$ flux in the apical microenvironment of cultured foetal distal lung epithelial cells. *J Exp Biol* 204: 785-795, 2001.

26. Linnane A W, Kovalenko S, and Gingold E B. The universality of bioenergetic disease. Age-associated cellular bioenergetic degradation and amelioration therapy. *Ann NY Acad Sci* 854: 202-213, 1998.

27. Lompre A M, Lambert F, Lakatta E G, and Schwartz K. Expression of sarcoplasmic reticulum Ca(2+)-ATPase and calsequestrin genes in rat heart during ontogenic development and aging. *Circ Res* 69: 1380-1388, 1991.

28. Lu X G, Azhar G, Liu L, Tsou H, and Wei J Y. SRF binding to SRE in the rat heart: influence of age. *J Gerontol A Biol Sci Med Sci* 53: B3-B10, 1998.

29. Manning W J, Shannon R P, Santiga J A, Parker A, Gervino E V, Come P C, and Wei J Y. Reversal of changes in left ventricular diastolic filling associated with normal aging using diltiazem. *Am J Cardiol* 67: 894-896, 1991.

30. Martin G M. Genetics and the pathobiology of ageing. *Philos Trans R Soc Lond B Biol Sci* 352: 1773-1780, 1997.

31. Mohaghegh P and Hickson I. Premature aging in RecQ helicase-deficient human syndromes (Abstract). *Int J Biochem Cell Biol* 34: 1496, 2002.

32. Morin S, Paradis P, Aries A, and Nemer M. Serum response factor-GATA ternary complex required for nuclear signaling by a G-protein-coupled receptor. *Mol Cell Biol* 21: 1036-1044, 2001.

33. Nakura J, Ye L, Morishima A, Kohara K, and Miki T. Helicases and aging. *Cell Mol Life Sci* 57: 716-730, 2000.

34. Olivetti G, Melissari M, Capasso J M, and Anversa P. Cardiomyopathy of the aging human heart. Myocyte loss and reactive cellular hypertrophy. *Circ Res* 68: 1560-1568, 1991.

35. Pearson A C, Gudipati C V, and Labovitz A J. Effects of aging on left ventricular structure and function. *Am Heart J* 121: 871-875, 1991.

36. Peterson L R, Rinder M R, Schechtman K B, Spina R J, Glover K L, Villareal D T, and Ehsani A A. Peak exercise stroke volume: associations with cardiac structure and diastolic function. *J Appl Physiol* 94: 1108-1114, 2003.

37. Pugh K G and Wei J Y. Clinical implications of physiological changes in the aging heart. *Drugs Aging* 18: 263-276, 2001.

38. Roffe C. Ageing of the heart. *Br J Biomed Sci* 55: 136-148, 1998.

39. Sakai M, Danziger R S, Staddon J M, Lakatta E G, and Hansford R G. Decrease with senescence in the norepinephrine-induced phosphorylation of myofilament proteins in isolated rat cardiac myocytes. *J Mol Cell Cardiol* 21: 1327-1336, 1989.

40. Semeniuk L M, Severson D L, Kryski A J, Swirp S L, Molkentin J D, and Duff H J. Time-dependent systolic and diastolic function in mice overexpressing calcineurin. *Am J Physiol Heart Circ Physiol* 284: H425-H430, 2003.

41. Slotwiner D J, Devereux R B, Schwartz J E, Pickering T G, de Simone G, Ganau A, Saba P S, and Roman M J. Relation of age to left ventricular function in clinically normal adults. *Am J Cardiol* 82: 621-626, 1998.

43. Spencer J A and Misra R P. Expression of the serum response factor gene is regulated by serum response factor binding sites. *J Biol Chem* 271: 16535-16543, 1996.

44. Spencer J A and Misra R P. Expression of the SRF gene occurs through a Ras/Sp/SRF-mediated-mechanism in response to serum growth signals. *Oncogene* 18: 7319-7327, 1999.

45. Swynghedauw B, Besse S, Assayag P, Carre F, Chevalier B, Charlemagne D, Delcayre C, Hardouin S, Heymes C, and Moalic J M. Molecular and cellular biology of the senescent hypertrophied and failing heart. *Am J Cardiol* 76: 2D-7D, 1995.

46. Taffet G E, Pham T T, and Hartley C J. The age-associated alterations in late diastolic function in mice are improved by caloric restriction. *J Gerontol A Biol Sci Med Sci* 52: B285-B290, 1997.

47. Takahashi T, Schunkert H, Isoyama S, Wei J Y, Nadal-Ginard B, Grossman W, and Izumo S. Age-related differences in the expression of proto-oncogene and contractile protein genes in response to pressure overload in the rat myocardium. *J Clin Invest* 89: 939-946, 1992.
48. Tanaka N, Dalton N, Mao L, Rockman H A, Peterson K L, Gottshall K R, Hunter J J, Chien K R, and Ross J. Jr. Transthoracic echocardiography in models of cardiac disease in the mouse. *Circulation* 94: 1109-1117, 1996.
49. Tokushima T, Reid C L, and Gardin J M. Left ventricular diastolic function in the elderly. *Am J Geriatric Cardiol* 10: 20-29, 2001.
50. Treisman R. The serum response element. *Trends Biochem Sci* 17: 423-426, 1992.
51. Treisman R. Journey to the surface of the cell: Fos regulation and the SRE. *EMBO J* 14: 4905-4913, 1995.
52. Tsou H, Azhar G, Lu X G, Kovacs S, Peacocke M, and Wei J Y. Age-associated changes in basal c-fos transcription factor binding activity in rat hearts. *Exp Cell Res* 229: 432-437, 1996.
53. Tyner S D, Venkatachalam S, Choi J, Jones S, Ghebranious N, Igelmann H, Lu X, Soron G, Cooper B, Brayton C, Hee Park S, Thompson T, Karsenty G, Bradley A, and Donehower L A. p53 mutant mice that display early aging-associated phenotypes. *Nature* 415: 45-53, 2002.
54. Vijg J and Wei J Y. Understanding the biology of aging: the key to prevention and therapy. *J Am Geriatr Soc* 43: 426-434, 1995.
55. Wei J Y and Levkoff S. *Aging Well: The Complete Guide to Physical and Emotional Health*. New York: Wiley, 2000.
56. Zhang X, Azhar G, Chai J, Sheridan P, Nagano K, Brown T, Yang J, Khrapko K, Borras A M, Lawitts J, Misra R P, and Wei J Y. Cardiomyopathy in transgenic mice with cardiac-specific overexpression of serum response factor. *Am J Physiol Heart Circ Physiol* 280: H1782-H1792, 2001.

Example Section 2

Maintaining Serum Response Factor Activity in the Older Heart Equal to that of the Young Adult is Associated with Better Cardiac Response to Isoproterenol Stress Introduction:

The process of cardiac aging transitions and overlaps with a number of cardiac pathological process such as hypertrophy and is often associated with reduced cardiac function, particularly during stress. It is hence plausible that cardiac aging and cardiac pathology share certain key molecular pathways in common and that understanding the process of cardiac aging will also advance the knowledge about disease processes and vice versa.

We have been interested in the transcriptional control during cardiac aging and have previously reported that SRF protein levels were increased in the old heart vs that in the young adult (5). SRF is a key cardiac transcription factor that regulates target genes by binding to the consensus sequence, CC(A/T)6GG (CArG) in genes (1-5). This CArG sequence is found in the promoter region of a number of key cardiac genes such as cardiac α-actin, α skeletal actin, desmin, sarcoplasma reticulum calcium ATPase (SERCA2a), sodium calcium exchanger (NCX1) and SRF itself (3, 5-11). SRF gene deletion results in embryonic death due to a defect in mesoderm formation (2-14).

In an effort to better understand the role of SRF in the adult heart we have developed several SRF transgenic mouse models with varying levels of cardiac-specific SRF expression. The SRF transgenic mice with moderate overexpression of wtSRF in the heart manifested significant cardiac hypertrophy and premature death (6). In addition, we have observed that a moderate reduction of SRF activity in the heart can also result in severe cardiomyopathy, and early post-natal mortality (8). These findings suggested that a moderate increase or decrease in SRF level was extremely detrimental for the heart. On the other hand, in another transgenic line of very mild wt SRF over-expression, there were changes of mild cardiac hypertrophy and diastolic impairment in young adulthood which mimicked that which is commonly seen in old mice and normal elderly persons (Example, Section 1). We hypothesized that if premature aging changes in the young adult heart could occur with a mild increase in SRF activity, then perhaps maintaining SRF protein levels in the old heart at that of the young adult would help to delay the appearance of age-related cardiac alterations. In this paper we describe the findings in binary transgenic mice with a reduction in SRF activity that was achieved by over-expressing a mutant form of SRF in a cardiac-specific, conditionally repressible manner. Interestingly, the hearts of the middle-aged binary transgenic mice had better function during stress compared to that of age-matched non-transgenic mice, suggesting that maintenance of cardiac SRF activity at levels similar to that of the young adult might be beneficial for the older heart.

Materials and Methods

Generation of Binary Mutant SRF Conditional Transgenic Mouse Lines

All mice used were on an FVB background and all the experiments conform with the *Guide for the Care and Use of Laboratory Animals* published by the US National Institutes of Health (NIH Publication No. 85-23, revised 1996). The studies were conducted with approval of the Institutional Review Boards of Beth Israel Deaconess Medical Center and University of Arkansas for Medical Sciences. A functional dominant negative mutant form of the human SRF gene (generous gift of Dr. Ravi Misra), termed dnSRF, was generated by site-directed mutagenesis (9). When compared with wild type SRF, this mutant protein is severely compromised in its ability to bind to the c-fos DNA SRE binding site (8). The sequence of wild-type SRF cDNA is accession number J03161, and the protein is AAA36647 (SEQ ID NO:8). The mutant is Thr->Ser at position 159 and Lys->Glu at position 163 of SRF.

The BD Biosciences Tet-Off gene expression system was used in the development of these transgenic models. One line was generated using a tetracycline-controlled trans-activator fusion protein (tTA) under the control of the alpha-MHC promoter. The tet-controlled transcriptional activator (tTA), is a fusion of the wild-type Tet repressor (TetR) to the VP16 activation domain of the herpes simplex virus. A second line of transgenic mice was generated with a tetracycline response element (TRE) fused with a minimal promoter from human cytomegalovirus (hCMV) followed by the mutant, dominant negative SRF coding sequence, containing 2 mutations in the amino acid positions of 159 and 163 of the SRF protein that compromises its ability to bind to SRE in the promoter region of target genes. When tTA binds to the TRE, it activates transcription in the absence of tetracycline or doxycline. A NotI fragment containing the transgenic construct and the pronuclear stage zygotes of FVB/N mouse were used for microinjection. At 2-3 weeks of age, a 1-cm portion of tail was removed from each mouse for DNA analysis. Two male founder mice were identified from 159 screened that were carrying the mutant SRF gene. These mice were then bred into a FVB/N background and transmitted the gene in an autosomal fashion. The SRF mutant mice were crossed with the α MHC-tTA mice to produce a line of binary transgenic mice. Of the progeny of the binary mice, 3 transgenic lines expressed the dominant negative SRF (dnSRF) under αMHC in the heart. Lines A and C showed significantly reduced (approximately 47%) SRF binding to SRE on EMSA and a mild reduction in protein expression (by 18%) on Western blots. Line B did not demonstrate reduced SRF binding to SRE. The potential binary, Mild-R SRF mice were screened twice by the polymerase chain reaction to confirm the identification of transgenic founder mice and to determine the transgene copy number in different transgenic lines. The data presented in this paper are from lines A and C. The primers used for identification of TRE-dnSRF were: forward: 5'-GT-TCATGCCTTCTTCTTTTTCCTA-3' (SEQ ID NO:9) and reverse: 5' GGTTTGTCCAAACTCATCAATGTA-3' (SEQ ID NO: 10). The primers used for identification of alpha MHC tTA were: forward:: 5'-GAGCTCCACTTAGACGGCGA-3' (SEQ ID NO: 1) and reverse: 5" CAACTTCCAGGGCCAG-GAGA-3' (SEQ ID NO:12).

We also studied the αMHC-tTa and the TRE-dn mutant SRF mice separately and found no significant differences in their hearts, compared to that in the Non-Tg. Hence, for this paper, we have employed age and sex-matched Non-Tg littermates as controls for the Mild-R-SRF Tg. To further test for cardiac specificity of expression and to test for any potential leakiness, the binary transgene mice were crossed with beta galactosidase Tg mice and the beta galactosidase was assayed in different tissues. No leakiness was detected with beta galactosidase assays.

Western blot Analysis 50 μg of protein was separated by SDS-polyacrylamide gel electrophoresis on a 10% polyacrylamide gel and transferred to nitrocellulose and subjected to Western blotting as previously published (5). The following antibodies were used: monoclonal SRF, 05-612, Upstate USA, and monoclonal SERCA2, Affinity Bioreagents, Golden, USA. Secondary antibodies were, Anti-Mouse IgG (Goat), HRP-Labeled, NEF822, from PerkinElmer Life.

Electrophoretic Mobility Shift Assay

Synthetic complementary oligonucleotides were 3'-biotinylated using the biotin 3'-end DNA labeling kit (Pierce) according to the manufacturer's instructions and annealed for 2 h at room temperature. The sequences of the oligonucleotides used are 5'-GGATGTCCATATTAGGACATCT-3' (SEQ ID NO: 13) for the wild-type SRE, and 5'-GGATGTC-CATATTATTACATCT-3' (SEQ ID NO:14) for the mutant SRE. Binding reactions were carried out for 20 min at room temperature in the presence of 50 ng/μl poly(dl-dC), 0.05% Nonidet P-40, 5 mM $MgCl_2$, and 2.5% glycerol in 1× binding buffer (LightShift™ chemiluminescent EMSA kit, Pierce) using 20 fmol of biotin-end-labeled target DNA and 4 μg of nuclear extract. Unlabeled target DNA (4 pmol) was added per 20 μl of binding reaction where indicated. Supershift reactions were run as described above with 2 μg of monoclonal anti-SRF antibody (TransCRUZ, Santa Cruz Biotechnology, Inc.) used for detection. Assays were loaded onto native 6% polyacrylamide gels pre-electrophoresed for 60 min in 0.5×TBE Buffer and electrophoresed at 100 V before being transferred onto a positively charged nylon membrane in 0.5×TBE Buffer at 100 V for 30 min. Transferred DNAs were cross-linked to the membrane for 15 min on a UV transilluminator equipped with 312 nm bulbs, and detected using horseradish peroxidase-conjugated streptavidin (LIGHTSHIFT™ chemiluminescent EMSA kit) according to the manufacturer's instructions.

Real-Time Polymerase Chain Reaction qRT-PCR was performed on the ABI PRISM 7700 Sequence Detection System by using random hexamers from the TaqMan Reverse Transcription Reagents and the Sybr Green PCR Master Mix for the PCR step (Applied Biosystems, CA). Below is the list of primers used in the study: BNP:(+)5' GGGAGAACACGCATCATTG-3" (SEQ ID NO:39), (−) 5'-ACAGCACCTTCAGGAGATCCA-3' (SEQ ID NO:15);

To allow comparison of qRT-PCR values, the concentration of cDNA in each sample was adjusted to yield similar amounts of PCR product when amplified by primers for 18 S. The 18S reaction was performed using standard curves representing 5, 1.25, 0.31, and 0.08 ng/ul of the pooled cDNA. Standard curves were generated for all other targets using pooled RT-PCR products at 80, 20, 5 and 1.25 ng/ul. Relative standard curve method is used to calculate the amplification difference between the samples.

Histological Analysis

After animals were killed, mouse hearts were immediately removed and placed in relaxing buffer (25 mM KCl in PBS). After treatment with relaxing buffer, the hearts were placed in 10% neutral-buffered formalin overnight. The atria were separated from the ventricles and then each ventricle was sectioned in 3- to 4-μm intervals from the apex upward. The sections were stained using standard hematoxylin and eosin (HE) or Masson Trichrome staining (MTS) protocols (Poly Scientific; Bayshore, N.Y.). Photomicro-graphs were obtained using a Nikon ES400 microscope.

To evaluate the fibrosis in the mouse myocardium, the digital images of MTS-stained cross section of the heart were captured at ×200 magnification. The true-color image analysis was performed by using the above software to quantify the collagen deposition as an indicator of fibrosis in the transgenic mice relative to that of the nontransgenic control mice. The observer performing the evaluations was blind to the transgenic status of the mice. The fibrotic areas stained blue with the MTS. The volume of fibrosis, measurement of wall thickness and myocyte size was quantified as previously reported (7).

Echocardiography

Adult mice were anesthetized with intraperitoneal injection of ketamine (50 mg/kg) and xylazine (4 mg/kg). The ventral chest was shaved, and the mouse was placed on a thermally controlled foam pad. Echocardiography was performed using a Hewlett-Packard Sonos 5500 ultrasound imaging system equipped with a 10-MHz pulsed array transducer. The ventral chest was shaved, and the mouse was placed on a thermally controlled foam pad. Echocardiography was performed using a Hewlett-Packard Sonos 5500 ultrasound imaging system equipped with a 10-MHz pulsed array transducer as previously reported (7). We also performed EKG monitoring on subgroups of Non-Tg and Mild-R SRF Tg mice at 3 and 15 months at baseline, and after isoproterenol injections to monitor any arrhythmias. The mice had sinus tachycardia in response to isoproterenol but none of the mice displayed any significant arrhythmias.

Intraventricular Pressure Measurements

Isoproterenol studies were used to produce acute hemodynamic stress of different intensities. Young (3 months) and older adult (15 months) male SRF-R Tg and age-matched non-Tg were used in the stress experiments. β adrenergic stress was employed because it has been standardized in rodent studies. Briefly, the carotid artery of each mouse was isolated and cannulated with a 1.4 F microtip catheter (Millar Instruments, Houston, Tex.), connected to an analog-to-digital recorder (PowerLab ML820, AD Instruments, Boulder, Colo.). After blood pressure was recorded, the transducer was advanced into the left ventricle LV peak systolic pressure (LVSP) and end-diastolic pressures (LVEDP), HR and maximum and maximum rates of pressure rise ($+dp/dt_{max}$) and fall ($-dp/dt_{min}$) were recorded at a sampling rate of 1 kHz. Isoproterenol was administered at a dose of 100 ng/kg/min with a low dose ranging between 30-35 ng or a moderate dose of 50-55 ng IV in different groups of mice. Intra-ventricular pressures recorded with a 1.4 F Millar catheter. Sham injections of 0.9% normal saline (0.9% NS), isovolumic to the isoproterenol, were given to age-matched mice. After the measurements, the mice were euthanized by ip administration of pentobarbital (150 mg/kg), consistent with the American Veterinary Medical Association Panel on Euthanasia guidelines.

Data Analysis

All values were expressed as means±SD. Data were analyzed by two independent observers blind to the transgenic status of the mice. Normality testing was performed on all data, and the t-test was used to determine the significance of differences between the two groups. When the data did not pass normality testing, the results were evaluated by the non-parametric Mann-Whitney U test and the equivalent Kruskall Wallis test for ANOVA. The criterion for significance was 0.05. Bonferonni correction was applied to multiple comparisons.

Results

Characterization of the Phenotype of the Binary Mild-R SRF Tg Mice

The binary transgenic, Mild-R SRF Tg mice over-expressed the mutant dominant negative SRF protein in a cardiac-specific manner. However, there were no developmental or reproductive abnormalities, and the litter sizes were normal (between 5-7). Initially, the binary transgenic mice were not distinguishable from the nontransgenic littermates, but in later adulthood (by middle-age), the transgenic mice appeared healthier and more active than the non-transgenic litter-mates. There was no significant difference in the heart weight to body weight ratio of the binary transgenic vs non-transgenic mice.

Figure 8:
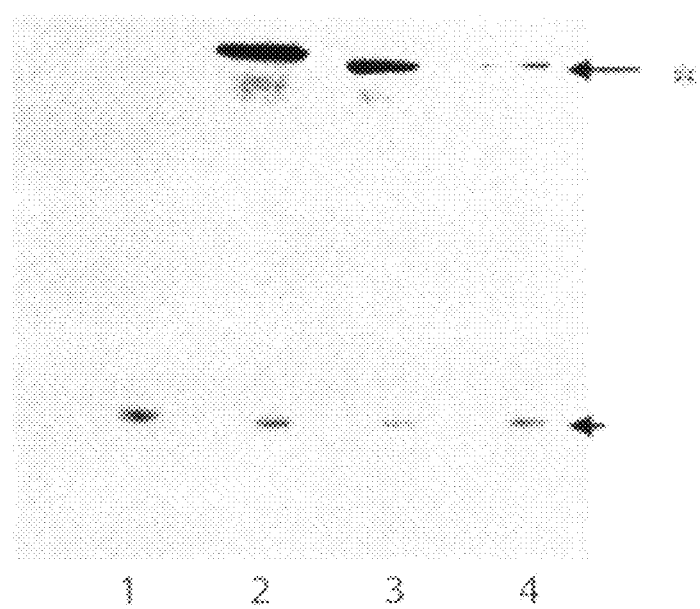
FIG. 8. Representative electrophoretic mobility shift assay of cardiac extract from hearts. Biotin labeled SRE probe is used in lanes 1-4. Lane 2 shows the retarded DNA protein complex formed from extract from a non-transgenic heart. Lane 3 and 4 have protein extract from hearts of Mild-R SRF Tg. Lane 3 shows reduced DNA binding compared with non-transgenic heart in lane 2. The specificity of DNA binding was confirmed by the top band in lane 4 (*) being competed away by excess specific unlabeled SRE probe. The arrow indicates free DNA probe that has migrated to the bottom of the gel because of its small size.
Figure 9:
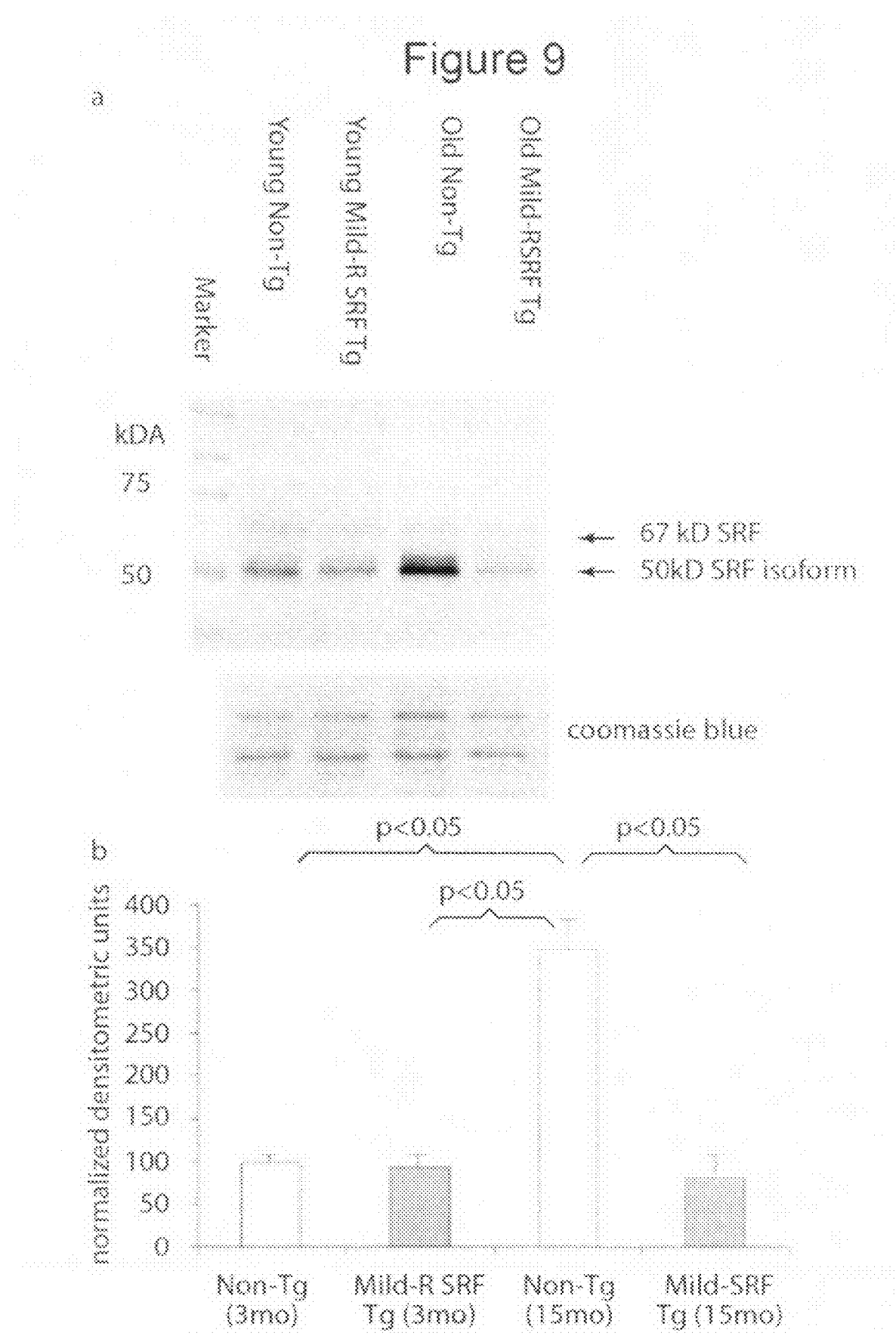
FIG. 9a. Representative Western blot of SRF protein from hearts. Y=young adult, 3 mos, O=older, 15 mos; n=5 in each group. The level of the shorter SRF isoform in the Mild-R-SRF Tg old heart is similar to that of a Non-Tg, young adult heart. Monoclonal SRF antibody (Upstate) was used. 9b. Averaged results of densitometric analysis of Western blot data from FIG. 9a. Data is representative of n=5 mice in Mild-R SRF Tg and non-transgenic group. Results are provided as means±SD, *p<0.05.

Expression of the Dominant Negative Mutant SRF in the Heart, Reduces SRF Protein Levels In EMSA assays, the protein lysate from hearts of the Mild-R SRF Tg showed an approximate 47% reduced binding of SRF to the wild-type SRE probe (p<0.05 Mild-R SRF Tg vs Non-Tg, FIG. 8). The expression of the mutant SRF protein caused a mild 11-12% reduction of SRF protein levels in the 3 month of Mild-R SRF Tg hearts compared to the age-matched non-Tg (FIG. 9a&b). However, in the older adults, at 15 months of age Mild-R SRF Tg had a 3.4 fold reduced protein expression of SRF compared with age-matched non-transgenic hearts (p<0.05, Mild-R SRF Tg vs Non-Tg, FIG. 9a&b). Also, there was no age-associated increase of the SRF protein levels in the Mild-R SRF Tg hearts as compared to that which was seen in the Non-Tg hearts.

Histological Examination of the Mild-R SRF Tg

Figure 10:
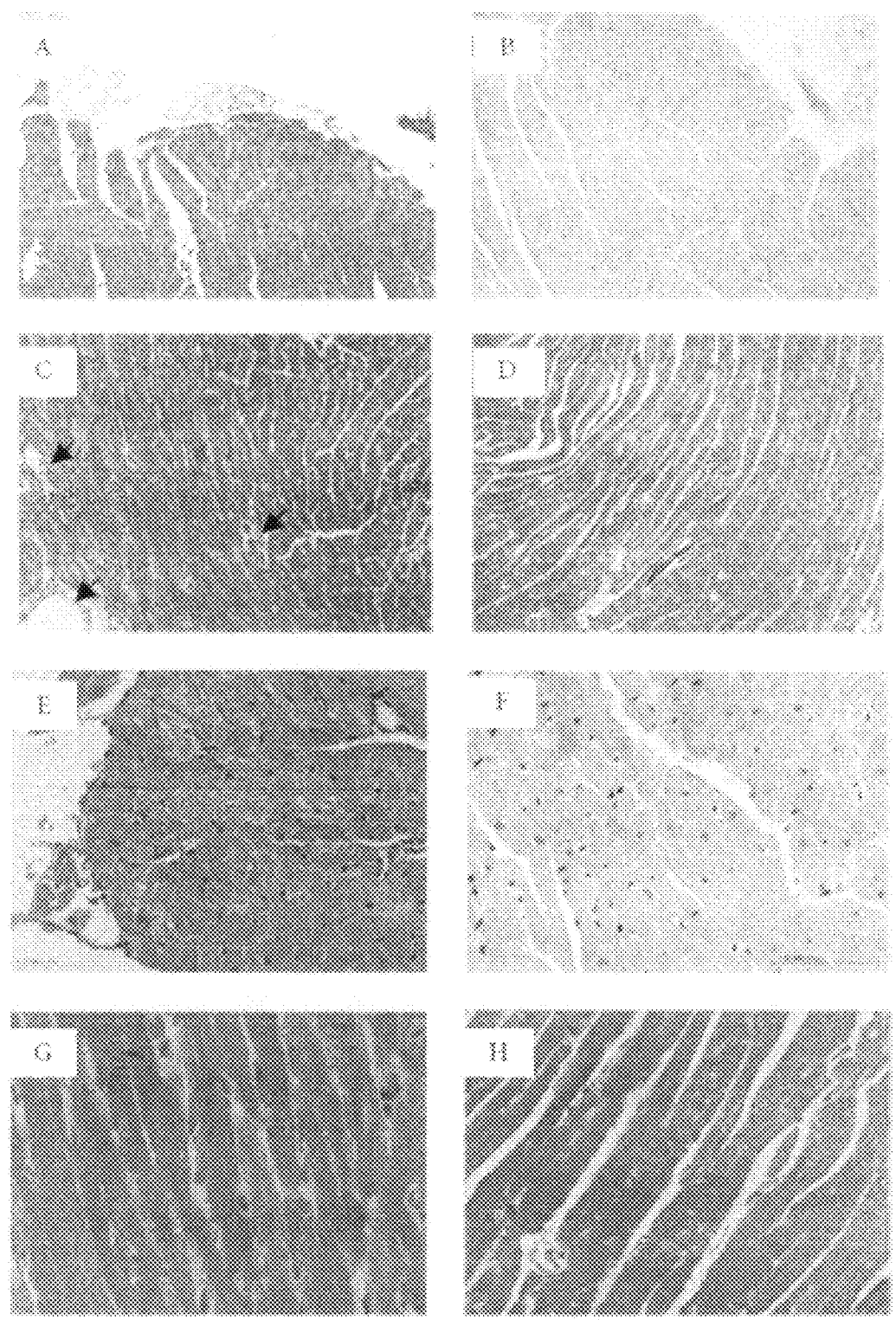
FIG. 10: Representative histological cross-sections from hearts of 15 month old Mild-R SRF Tg and age-matched non-Tg mice that have not been repressed by doxycyline. Left panel, A, C, E, G=Non-transgenic, hearts; Right panel, B, D, F, H=Mild-R SRF Tg hearts. A-B are cross-sections, H&E stain (4×); C-D are Masson Trichome stain for collagen (20×). The Masson Trichome stain in C and D, shows significantly greater fibrosis in the Non-transgenic control (represented by the black arrows), than in the Mild-R SRF Tg heart. Panels E-H represent H&E staining of Non-Tg and Mild-R SRF Tg heart cross-sections (40×), with micrometer in lower left hand corner. There is no significant difference in cardiomyocyte size but the structure of cardiomyocytes appears better in the Mild-R SRF Tg mouse hearts (H), with well defined cardiomyocytes (pink, polygonal shaped cells) and larger nuclei (blue dots) as compared to non-Tg (E). Panels I-J are Masson Trichome stain, longitudinal sections (40×) of Non-Tg and Mild-R SRF Tg.

The gross morphological examination of all the organs of the binary Mild-R SRF Tg mice was normal. The hearts of the Mild-R SRF Tg mice showed no significant difference in atrial or ventricular wall thickness at baseline compared to the non-transgenic. The cardiomyocyte structure was well maintained in the 15 month old Mild-R SRF Tg with well defined cardiomyocytes and nuclei, whereas in the age-matched non-transgenic hearts, the cardiomyocytes were heterogenous in size and were not well aligned (FIG. 10). Since the FVB strain of mice have a relatively short life-span (18-24 months), the morphology of the 15-month-old Non-Tg mouse hearts correlated with alterations occurring in normal older middle-aged mice. There was also a mild increase in cardiomyocyte cross-sectional area in the Mild-R-SRF Tg, but it was not significant. There was an approximate 5.8% volume of reduced cardiac fibrosis in Mild-R SRF Tg mice compared with the non-transgenic (FIGS. 10C and D, p<0.05). The collagen increase in the age-matched non-transgenic hearts was mainly interstitial and perivascular.

Functional Cardiac Changes

Figure 11:
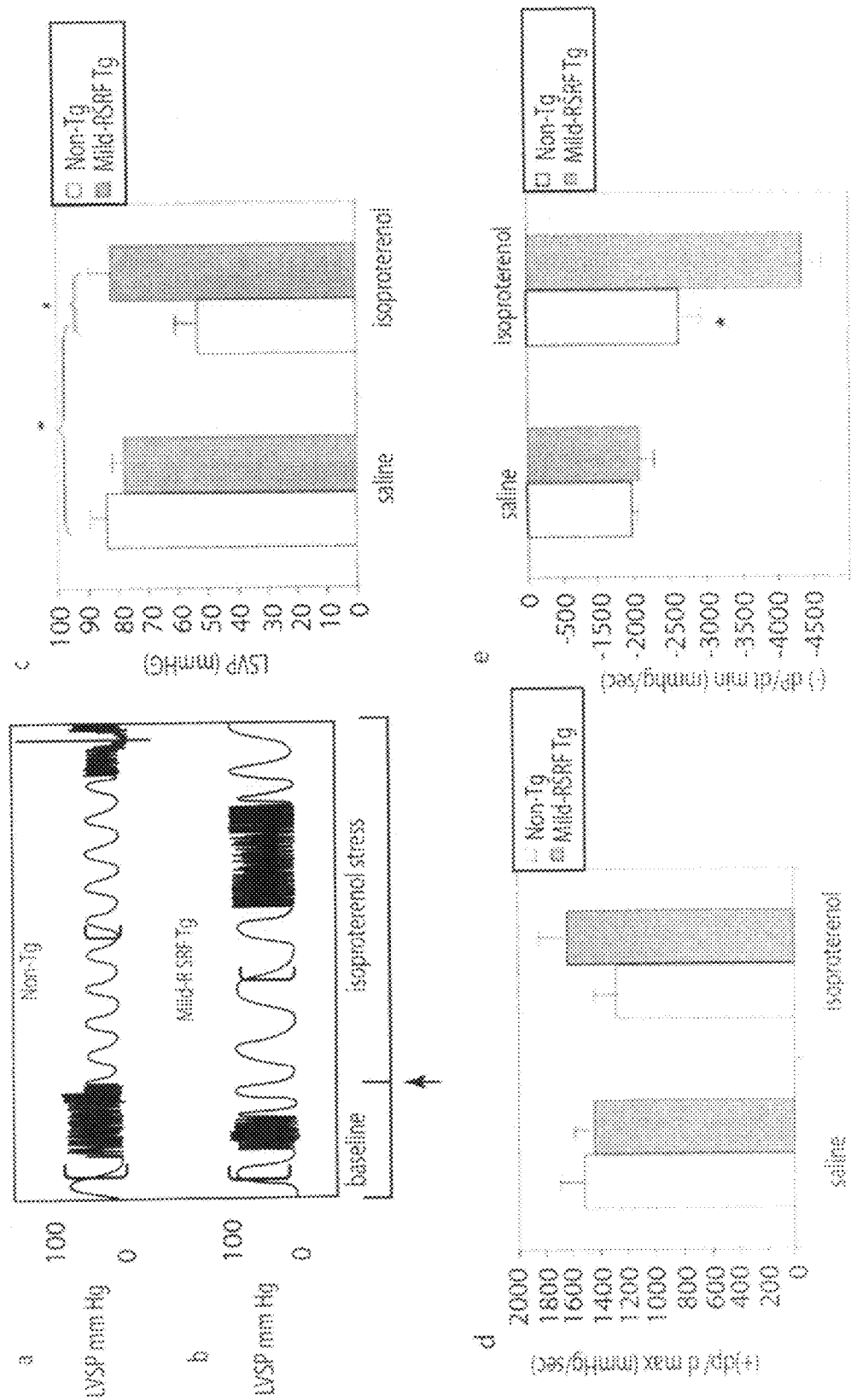
FIG. 11a: Left ventricular pressures (LVSP) under isoproterenol stress in 15 month old Non-Tg mice. 11b: LVSP in Mild-R SRF Tg mice, under same conditions as the Non-Tg mice. Note, LVSP decreases with moderate isoproterenol stress in the Non-Tg mice, but is maintained in the Mild-R SRF Tg. The vertical red lines on the tracing show differences in amplitude change in LVSP. The crowded dark lines in the tracing are just indicative of a slower paper speed. ISO=isoproterenol. NS non-significant. 11c. Bar graphs showing differences in LVSP between 15 month old Non-Tg and Mild-R SRF Tg hearts. Data shown in the bar graphs is representative of n=4 mice in each group and is provided as means±SD with *p<0.05. 11d. Bar graphs showing differences in (+) dp/dt indices between 15 month old Non-Tg and Mild-R SRF Tg hearts. Data shown in the bar graphs is representative of n=4 mice in each group and is provided as means±SD. 11e. Bar graphs showing differences in (−) dp/dt indices between 15 month old Non-Tg and Mild-R SRF Tg hearts. Data shown in the bar graphs is representative of n=4 mice in each group and is provided as means±SD with *p<0.05.

Baseline evaluation of Mild-R SRF Tg mice at 15 months of age displayed cardiac functional indices similar to that of age-matched non-transgenic (Table 2). Although there was a tendency towards a greater cardiac index in the Mild-R SRF Tg, it was not significant. However, there was significantly better cardiac relaxation in the Mild-R SRF Tg compared with Non-Tg (69.4±7.5 vs 56.1±4.9, p<0.05). We also evaluated cardiac function using intravenous isoproterenol to induce β-adrenergic stress. Our data suggest that the older adult 15 month Mild-R SRF Tg mouse hearts performed better than their age-matched non-transgenic litter-mates in similar conditions of β-adrenergic stress. In response to a low dose of isoproterenol, the LVSP slightly increased in both non-Tg and Mild-R SRF Tg mice, but the difference was not significant (data not shown). However, in response to a moderate dose of intravenous isoproterenol stress, the left ventricular systolic pressure (LVSP) values fell significantly in the non-transgenic mice in contrast to the Mild-R SRF Tg mice where the LVSP was much better maintained (p<0.05 Mild-R SRF Tg vs Non-Tg, FIG. 11a-c). The maximal rate of developed pressure over time (+dp/dt) did not change significantly with isoproterenol stress in the Mild-R SRF Tg, or in the Non-Tg (FIG. 11d). The rate of relaxation (−dp/dt) was significantly better in the Mild-R SRF Tg in response to isoproterenol than the Non-Tg (p<0.05, FIG. 11e).

TABLE 2

Echocardiographic findings.

| | Non-Tg | | SRF-R TC | | |
|---|---|---|---|---|---|
| | Mean value | SD ± | Mean value | SD ± | p value |
| Body Wt (gms) | 39.5 | 7.4 | 37.5 | 5.1 | <0.4 |
| LV mass (g) | 0.16 | 0.003 | 0.14 | 0.01 | <0.1 |
| LV mass/body weight | 3.9 | 0.42 | 4.1 | 0.53 | <0.7 |
| Heart rate (beats/min) | 504 | 48.7 | 528 | 25.9 | <0.2 |
| PWd mm$^3$ | 0.96 | 0.11 | 0.88 | 0.03 | <02 |
| PWs mm$^3$ | 1.55 | 0.16 | 1.42 | 0.04 | <0.1 |
| Awd mm$^3$ | 1.006 | 0.02 | 0.8 | 0.07 | <0.4 |
| AWs mm$^3$ | 1.59 | 0.17 | 1.49 | 0.07 | <0.2 |
| LVDd mm$^3$ | 3.92 | 0.23 | 4.02 | 0.21 | <0.3 |
| LVDs mm$^3$ | 2.3 | 0.4 | 2.4 | 0.1 | <0.5 |
| Ejection fraction % | 44.3 | 7.3 | 49.1 | 2.1 | <0.08 |
| Vol d mm$^3$ | 73.1 | 14.9 | 68.1 | 6.0 | <0.3 |
| Vol s mm$^3$ | 14.1 | 9.7 | 15.2 | 2.2 | <0.7 |
| RW th mm$^3$ | 0.46 | 0.02 | 0.43 | 0.07 | <0.1 |
| Candiac index μl/min/g | 650.2 | 184.4 | 818.9 | 204.0 | <0.1 |
| peak E | 56.1 | 4.9 | 69.4 | 7.5 | <0.05 |

Values are expressed as means ± SD; n = 12 mice. PWd = posterior wall thickness (diastolic); PWs = posterior wall thickness (systolic); AWd = anterior wall thickness diastolic; AWs = anterior wall thickness (systolic); LVDd = left ventricular diastolic dimension; LVDs = left ventricular systolic dimension; Vol d = volume in diastole; Vol s = volume in systole; RWth = relative wall thickness; Peak E = maximal early diastolic transmitral flow velocity.

Figure 12:
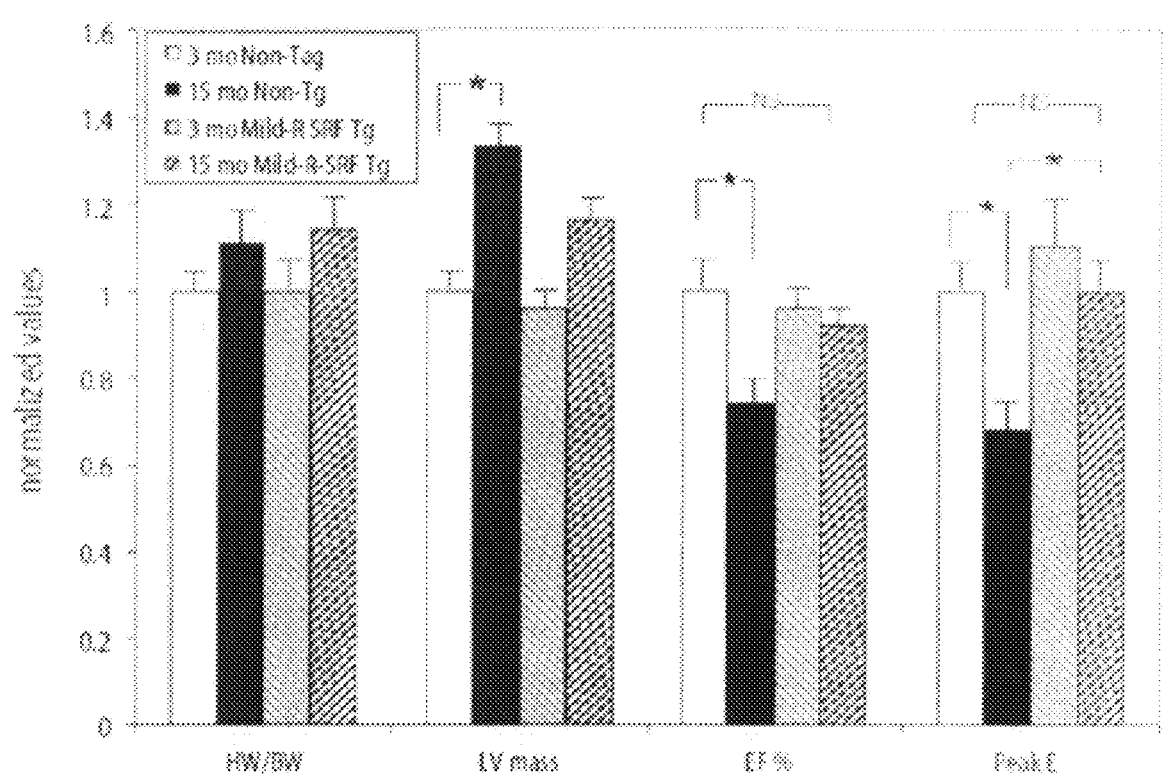
FIG. 12: Bar graph of normalized data obtained from echocardiography of 3 month and 15 month old Non-Tg and age-matched Mild-R-SRF Tg mice. All data was obtained at baseline and normalized to 3 month old Non-Tg for comparison. n=5 mice in each group and the normalized values are provided as means±SD, *p<0.05.

Because of the favorable cardiac function in the 15 month old Mild-R SRF Tg, we also compared alterations in cardiac function in Non-transgenic FVB mice and Mild-R SRF Tg mice at baseline, between 3 and 15 months of age. We observed an age-related decline in cardiac function in Non-transgenic mice with a significant increase in left ventricular mass, but a significant decrease in ejection fraction and peak E (p<0.05, FIG. 12). On the other hand, cardiac function was well maintained in the Mild-R SRF Tg and did not suffer a decline by 15 months of age (FIG. 12).

Alteration of Gene Expression in the Mild-R SRF Tg Hearts could Favor Better Cardiac Performance.

Figure 13:
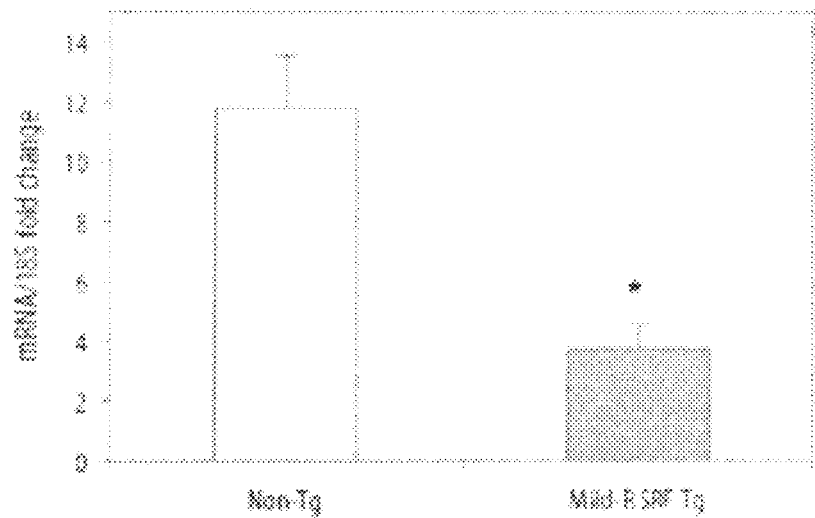
FIG. 13: Expression of brain naturetic peptide (BNP) in 15 month old Mild-R SRF Tg and age-matched controls. The results of real-time RT-PCR are given as a relative expression of mRNA normalized to 18S housekeeping gene, fold change in gene expression. n=5 mice in Mild-R SRF Tg and non-transgenic group. Results are provided as means±SD, *p<0.05 Non-Tg, vs Mild-R SRF Tg using the Mann Whitney U test.
Figure 14:
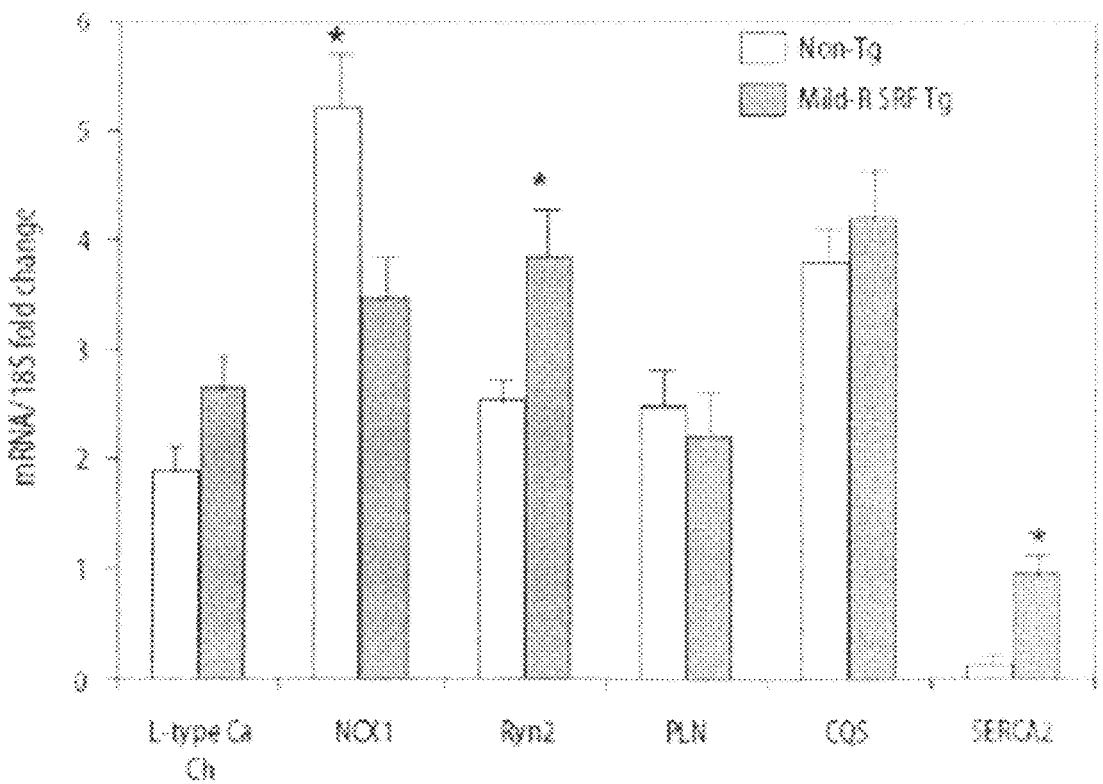
FIG. 14: Expression of genes involved in calcium handling in 15 month old Mild-R SRF Tg and 7ge-matched controls. The results of real-time RT-PCR are given as a relative expression of mRNA normalized to 18S housekeeping gene, fold change in gene expression. n=5 mice in Mild-R SRF Tg and non-transgenic group. Results are provided as means±SD, *p<0.05 Non-Tg, vs Mild-R SRF Tg using the Mann Whitney U test. x axis: Ca Ch=α 1 sub-type L-type calcium channel; NCX1=Sodium Calcium exchanger type1; Ryr2=ryanodine receptor type 2; PLN=phospholmaban; CQS=calsequestrin, SERCA=Sarcoplasmic endoplasmic reticulum calcium ATPase.

We have analyzed 2 sets of genes: the first set belonged to genes usually expressed in cardiac hypertrophic conditions which included cardiac actin, skeletal actin, BNP, αMHC and βMHC. Among this set of genes, a significant notable finding was the reduced BNP expression in the Mild-R SRF Tg hearts (p<0.05, Mild-R SRF Tg vs Non-Tg, FIG. 13). Other cardiac structural genes such as cardiac actin, skeletal actin α MHC and β MHC expression showed no significant change as compared to the non-transgenic (data not shown). The second set of genes were selected for their control of calcium regulation in the heart, being upstream of SRF, and hence their influence on cardiac contractility. Sodium-Calcium exchanger was significantly reduced but SERCA2 and the ryanodine receptor 2 had significantly increased expression in the Mild-R SRF Tg hearts compared to Non-Tg (p<0.05, Mild-R SRF Tg vs Non-Tg, FIG. 14). We also evaluated protein expression of the calcium regulating genes and found a significant difference only in the SERCA2 expression (p<0.05, Mild-R SRF Tg vs Non-Tg, FIG. 15a&b).

Discussion

Several interesting results have emerged from these studies. They suggest that preventing the usual age-associated increase in SRF protein level in the heart might be advantageous in older adults.

The adult binary Mild-R SRF Tg mice did not exhibit any features of cardiac hypertrophy, pre-mature cardiac aging or cardiac dysfunction which have been reported with wild-type SRF over-expression models (6-8). In fact, the hearts of older adult Mild-R SRF Tg mice were on the whole better preserved than that of normal age-matched non-transgenic mice (Non-Tg), both morphologically and functionally. This was also true at the level of gene and protein expression.

The finding on baseline echocardiography of an increased peak E, or early ventricular relaxation, in the older adult Mild-R SRF Tg vs Non-Tg heart, suggests that the usual age-associated stiffening of the left ventricle did not occur in these older adult binary transgenic mice. This finding might also have contributed to the somewhat higher cardiac index that was observed in the older adult Mild-R SRF Tg vs Non-Tg mice (7, 15). We have also evaluated echocardiograms in young adult (3 month) vs older adult (15 month) non-transgenic mice of the same background (FVB) strain as the Mild-R SRF Tg, which showed a mild but significant age-related decrease in the ventricular relaxation rate that is similar to what we and others have previously observed (7, 15, 16). Although for most strains of mice 15 months is generally not considered 'old', the FVB-N strain of mice usually have a shorter life-span, with a median life-span of about 21-24 months (17-18). Hence, the Non-Tg hearts, at 15 months, are approximately equivalent to the hearts of late middle-age for the FVB strain of mice, displaying some of the morphological and functional features observed during typical cardiac aging (7, 15-18). It would be of interest to determine whether in the very old FVB mice (over 21 months), the Mild-R SRF Tg mice can still maintain cardiac health better than their very old Non-Tg counter-parts.

By using a specific monoclonal antibody against the full-length SRF, we have observed that the shorter SRF isoform appears prominently and compared with the full-length SRF isoform, appears to show more of an age-associated increase. Davis et al reported that a 52 kDa SRF isoform was increased in failing human hearts (19). However, the antibody used in that study was polyclonal, and the tissues studied were from human and rabbit hearts, while the antibody used in the present study was monoclonal and the tissue studied was from mouse hearts.

The Mild-R SRF Tg hearts displayed better parameters of diastolic function than that of Non-Tg mice, with an increased peak E at baseline and increased (−) dp/dt values in response to isoproterenol stress. This finding is in contrast to the reduced relaxation rate and the prolonged cardiac relaxation duration usually observed during adult aging, also in cardiomyopathies and in other lines of transgenic mice with mild over-expression of wild-type SRF (7, 20). The increased peak E in the Mild-R SRF Tg might also have contributed to the somewhat higher cardiac index observed in these mice, although it did not reach significance (15-16). At the morphological level, there was significantly reduced fibrosis in the 15 month old Mild-R SRF Tg compared to that of age-matched Non-Tg, which might be indicative of a reduced activation of collagen gene promoter activity in these mice (3-11)

Another interesting finding in the present study was that the cardiac function in response to a moderate degree of β adrenergic stress was better maintained in the Mild-R SRF Tg vs Non-Tg mice. The β adrenergic receptor (β-AR) signaling pathway influences many aspects of cardiac function including the contractile and relaxation ability, heart rate and the response to stress (20-22). Many clinical trials have shown that beta-blockers significantly reduce morbidity and mortality in cardiac patients (23). In general, βAR responsiveness decreases with normal adult aging, perhaps as a natural endogenous downregulation to protect against stress and the age-associated increased levels of circulating catecholamines (20). The usual age-related decline in β-adrenergic response may result in a flat or even negative ionotropic response in older hearts (20, 22-23). The cardiac functional response to isoproterenol in-vivo is complex and concentration dependent. In our study, using a moderate dose of isoproterenol, the cardiac function was better maintained in the Mild-R SRF Tg mice, supporting the notion that mechanisms downstream of the β adrenergic receptors as well as possibly others independent of the βAR signaling pathway might have contributed to the observed age-related decline in βAR responsiveness.

We found that a number of target genes regulated by SRF were altered in the transgenic mice and these changes could have favorably influenced cardiac function in the older adult (15 month old) Mild-R SRF Tg vs Non-Tg mouse. Notable among these was a reduced level of BNP expression in the Mild-R SRF Tg compared with Non-Tg. The reduction in BNP might be indicative of and might also be participatory in the maintenance of cardiac performance under stress in the older adult Mild-R SRF Tg vs Non-Tg mice, since high levels of BNP and ANF are often associated with hypertrophic cardiomyopathies and are often interpreted to be poor prognostic indicators of poor outcome in congestive heart failure (7, 26). Both ANP and BNP have important beneficial physiological effects on the heart, vasculature and kidneys (27-29). The intravenous infusion of BNP, which promotes diuresis, has been shown to alleviate acute heart failure. However, when levels of BNP remain elevated for prolonged periods, it is usually a natural adaptive mechanism for some degree of cardiac decompensation (27). In the absence of acute hemodynamic stress, ANP and BNP levels are normally quite low, and reduced levels of BNP after myocardial infarction are a good prognostic indicator and predict reduced risk of death and heart failure (29). It has also been suggested that BNP might be more than just a hemodynamic marker of cardiac decompensation, and that elevated levels reflect cardiac structural remodelling and active inflammation (30). Our previous models of SRF over-expression have shown significantly higher levels of ANF and a recent study of SRF regulated gene expression in cardiomyocytes revealed that cells deficient in SRF had reduced expression of ANF, NCX1, c-fos, α MHC, β MHC and c-fos (3, 6-8). Hence, it is plausible that the lower levels of cardiac BNP in the older adult Mild-R SRF Tg vs Non-Tg might reflect preserved function in the heart.

Our study also suggests that SRF might play a significant role in cardiac function via regulation of calcium handling proteins in the hearts. This might also partly form the basis of the improved β-adrenergic stress response of the Mild-R SRF Tg mice. Calcium also directly promotes phosphorylation of an important serine 103 site on the SRF molecule which then potentiates its binding to the serum response element in the promoter region of SRF target genes (1-10). SRF has also been shown to regulate the NCX promoter, which can influence cytoplasmic calcium content of the cell (31). It has recently been reported that a reduced level of NCX1 might increase cardiac tolerance to ischemic stress (31). Hence, it appears plausible that the reduced NCX1 expression in the Mild-R SRF Tg could potentially also be protective under other conditions associated with β-adrenergic stress such as myocardial ischemia. Further studies on the NCX protein levels and phosphorylation status in the Mild-R SRF Tg and Non-Tg will be of interest.

It was also notable that the expression of SERCA2 gene, which is usually decreased in the heart with advancing age, in congestive heart failure, and in wild-type SRF over-expressing mice, was significantly increased in the hearts of Mild-R SRF Tg vs Non-Tg mice (6-7, 32-34). Since SERCA2 is also an SRF target gene, the finding of an increased level of SERCA2 in the Mild-R SRF Tg is of interest. One explanation could be that an increase in SERCA2 might be compensatory to a reduced level of NCX1, with which it tends to maintain an inverse relationship (32). These findings also highlight the complex in-vivo gene regulation by SRF which includes both cooperative and repressive partnering with different co-factors. We have recently identified a novel co-factor of SRF, p49/STRAP, which might also influence SRF regulated gene expression (9).

The increased SERCA2 protein, as a key sarcoplasmic calcium pump protein, might have been the basis for the improved cardiac contractility of the older adult Mild-R SRF vs Non-Tg hearts under stress. The fact that cardiac contractility was not changed at baseline in the Mild-R SRF Tg hearts, in spite of the increase in SERCA2 protein, is compatible with the notion that the level of increase was not sufficient to later function at baseline, but was sufficient for maintaining function under stress. It could also be attributed to alterations in the phosphorylation status of phospholamban, which was not assessed in the present study. The level of L-type calcium channel, which is reported to undergo a mild compensatory increase with age, showed slight but no significant increase in the Mild-R SRF Tg (34-35). A recent study by Maier et al demonstrated increased contractility in SERCA2a transgenic rat hearts (34). However, there was also increased mortality in these mice, which might have been due to calcium leak across the ryanodine receptor, resulting in afterdepolarizations and arrhythmias (34). Thus, it is likely that an optimal level of SERCA2 expression might be required for a beneficial effect.

A relative reduction in ryanodine receptor levels or alterations in its phosphorylation have been associated with fatal arrhythmias and congestive heart failure (29). The ryanodine receptors were increased at the mRNA but not the protein level, in the Mild-R SRF Tg. It is possible though that the phosphorylation status of the ryanodine receptor, which we did not assess, might have also contributed to the better maintained cardiac function under stress, since Recently, the study by Parlakian et al showed that conditional deletion of SRF in the adult heart resulted in rapid development of cardiomyopathy and death (36). The work of Parlakian et al is in support of our previous study in which we markedly reduced SRF activity in hearts which caused dilated cardiomyopthay and death within 2 weeks (36). A number of other studies highlight the significant role of SRF in controlling cardiac specific genes in primary cardiomyocytes (36-39). In humans the importance of SRF in the development of pathophysiology is illustrated by cases in which increased expression of SRF in cardiac tissue is associated with heart failure (19). Nevertheless, more studies need to conducted to elucidate the role of SRF in cardiac pathophysiology, especially with regards to adult aging (25, 40). We have observed that even a mild increase of wtSRF in young adult hearts could mimic cardiac aging, and interestingly, the current paper further supports that hypothesis and suggests that a mild reduction of SRF in the heart might actually be beneficial and help maintain cardiac function in the older adult heart.

Conclusion: The field of SRF research is rapidly advancing and it is becoming increasingly clear that SRF has an important role in regulating a number of immediate early and muscle-specific genes, as well as cell proliferation, cell size, cell survival and calcium regulation. Our current study suggests that by preventing SRF protein increase in the hearts of older adults and by maintaining SRF levels close to that of the young adult, the cardiac reserve capacity and function can be maintained. Further studies of the effect of a mild reduction in SRF gene expression in the heart could be helpful in the future to improve cardiac functional reserve.

References

1. West A G, Shore P, Sharrocks A D. DNA binding by MADS-box transcription factors: a molecular mechanism for differential DNA bending. Mol Cell Biol. 1997 May; 17(5):2876-87.
2. Spencer J A and Misra R P. Expression of the serum response factor gene is regulated by serum response factor binding sites. J Biol Chem 271: 16535-16543, 1996.
3. Nelson T J, Balza R Jr, Xiao Q, Mistra R P. SRF-dependent gene expression in isolated cardiomyocytes: regulation of genes involved in cardiac hypertrophy. J Mol Cell Cardiol. 2005 September; 39(3):479-89.
4. Tsou H, Azhar G, Lu X G, Kovacs S, Peacocke M, Wei J Y. Age-associated changes in basal levels of c-fos transcription factor binding activity in rat hearts. Exp Cell Res 1996; 229:432-437.
5. Lu X G, Azhar G, Liu L, Tsou H, Wei J Y. SRF binding to SRE in the rat heart: influence of age. J Gerontol 1998; 53A:B3-B10.
6. Zhang X M, Azhar G, Chai J, Sheridan P, Nagano K, Brown T et al. Cardiomyopathy in transgenic mice with cardiac-specific overexpression of serum response factor. Am J Physiol. 2001, 280 (4): H 1782-92.
7. Zhang X, Azhar G, Furr M, Wei J Y. Model of functional cardiac aging: Young adult mice with mild over-expression of serum response factor. Am. J. Physiol. 2003, 285: R552-R560.
8. Zhang X, Chai J, Azhar G, Sheridan P, Borras A M, Furr M C et al. Early postnatal cardiac changes and premature death in transgenic mice overexpressing a mutant form of serum response factor. J Biol. Chem. 2001, 276(43): 40033-40.

9. Zhang X, Azhar G, Zhong Y, Wei J Y. Identification of a Novel Serum Response Factor Cofactor in Cardiac Gene Regulation. J Biol Chem 2004; 279(53):55626-32.
10. Miano J M. Serum response factor: toggling between disparate programs of gene expression. J Mol Cell Cardiol. 2003; 35: 577-593.
11. Balza R O Jr., Misra R P. Role of the serum response factor in regulating contractile apparatus gene expression and sarcomeric integrity in cardiomyocytes. J Biol Chem. 2006 Mar. 10;281(10):6498-510.
12. Parlakian A, Tuil D, Hamard G, Tavernier G, Hentzen D, Concordet J P et al. Targeted inactivation of serum response factor in the developing heart results in myocardial defects and embryonic lethality. Mol Cell Biol. 2004; 24: 5281-5289.
13. Miano J M, Ramanan N, Georger M A, de Mesy Bentley K L, Emerson R L et al. Restricted inactivation of serum response factor to the cardiovascular system. Proc Natl Acad Sci U S A. 2004; 101: 17132-17137.
14. Niu Z et al. Conditional mutagenesis of the murine serum response factor gene blocks cardiogenesis and the transcription of downstream gene targets. J Biol Chem. 2005 Septmber 16;280(37):32531-8.
15. Assayag P, Charlemagne D, de Leiris J, Boucher F, Valere P E, Lortet S et al. Senescent heart compared with pressure overload-induced hypertrophy. Hypertension 29: 15-21, 1997.
16. Forman D E, Cittadini A, Azhar G, Douglas P S and Wei J Y. Cardiac morphology and function in senescent rats: gender-related differences. J Am Coll Cardiol. 1997 December; 30(7):1872-7.
17. Mahler F. Joel, Stokes W, Mann C. P, Takaoka M and Maronpot R. R. Spontaneous lesions in Aging FVB/N mice. Toxicologic Pathology, 24:710-716, 1996.
18. Hennings H, Glick A. B., Lowry D. T., Krsmanovic L. S., Sly L. M., and Yuspa S. H. FVB/N mice: An inbred strain sensitive to the chemical induction of squamous cell carcinomas in the skin. Carcinogenesis 14; 2352-2358, 1993.
19. Gupta M, Davis F J, Jayakar D and Jeevanandam V. Increased expression of alternatively spliced dominant-negative isoform of SRF in human failing hearts. Am J Physiol Heart Circ Physiol. 2002 April;282(4):H1521-33.
20. Lakatta E G and Sollott S J. Perspectives on mammalian cardiovascular aging: humans to molecules. Comp Biochem Physiol A 132: 699-721, 2002.
21. J. Mark Jones, Jason A. Petrofski, Katrina H. Wilson, Charles Steenbergen, Walter J. Koch and Carmelo A. Milano beta2 adrenoceptor gene therapy ameliorates left ventricular dysfunction following cardiac surgery. Eur J Cardiothorac Surg. 2004 December;26(6):1161-8.
22. Hendrik T. Tevaearai, G. Brant Walton, Janelle R. Keys, Walter J. Koch, Andrea D. Eckhart. Acute ischemic cardiac dysfunction is attenuated via gene transfer of a peptide inhibitor of the β-adrenergic receptor kinase (βARK1) J Gene Med. 2005 September;7(9):1172-7.
23. Jost A et al. Beta-blocker treatment of chronic systolic heart failure improves prognosis even in patients meeting one or more exclusion criteria of the MERIT-HF study. Eur Heart J. 2005 December;26(24):2689-97
24. Stratton J R, Levy W C, Schwartz R S, Abrass I B, Cerqueira M D. Beta-adrenergic effects on left ventricular filling: influence f aging and exercise training. J Appl Physiol. 77(6): 2522-9, 1994.
25. P. Anversa, M. Rota, K. Urbanek, T. Hosoda, E. H. Sonnenblick, A. Leri, J. Kajstura and R. Bolli. Myocardial Aging. Basic Res. Cardiology October; 482-493, 2005
26. Walther T, Klostermann K, Heringer-Walther S, Schultheiss H P, Tschope C, Stepan H. Fibrosis rather than blood pressure determines cardiac BNP expression in mice. Regul Pept. 2003 Nov. 15;116(1-3):95-100.
27. Kawakami R, Saito Y, Kishimoto I, Harada M, Kuwahara K, Takahashi N et al. Overexpression of brain natriuretic peptide facilitates neutrophil infiltration and cardiac matrix metalloproteinase-9 expression after acute myocardial infarction. Circulation. 110 (21):3306-12. 2004.
28. Molkentin D. J. A friend within the heart:natriuretic peptide receptor signaling. The J of Clinic Investigation, 111: 1275-1277, 2003.
29. Lemos J. A., Morrow D. A, Bentley J. H., Omland T, Sabatine M. S., McCabe C. H. et al. The prognostic value of B-type natriuretic peptide in patients with acute coronary syndromes. N Engl J Med. 2001 Oct. 4;345(14):1014-21.
30. Mahra M R, Uber P A, Walther D, Vesely M, Wohlgemuth J G, Prentice J et al. Gene expression profiles and B-type natriuretic peptide elevation in heart transplantation: more than a hemodynamic marker. Circ. 114(1 Suppl):121-6, 2006.
31. Cheng, G, Hagen T P, Dawson M L, Barnes K V, Menick D R. The role of GATA, CArG, E-box, and a novel element in the regulation of cardiac expression of the Na-ca exchanger gene. J Biol. Chem. 1999; 274(18):12819-26.
32. Iyuki Namekata, Hideki Nakamura, Hideaki Shimada, Hikaru Tanaka and Koki Shigenobu. Cardioprotection without cardiosuppression by SEA0400, a novel inhibitor of Na+-Ca2+ exchanger, during ischemia and reperfusion in guinea-pig myocardium. Life Sci. 2005 June 3;77(3): 312-24.
33. Heerdt P M, Klotz S, Burkhoff D. Cardiomyopathic etiology and SERCA2a reverse remodeling during mechanical support of the failing human heart. Anesth Analg. 2006 January;102(1):32-7.
34. Maier L S et al. Increased SR Ca2+ cycling contributes to improved contractile performance in SERCA2a-overexpressing transgenic rats. Cardiovasc Res. 2005 September 1;67(4):636-46.
35. Cerrone M, Colombi B, Santoro M, di Barletta M R, Scelsi M, Villani L et al. Bidirectional ventricular tachycardia and fibrillation elicited in a knock-in mouse model carrier of a mutation in the cardiac ryanodine receptor. Circ Res. 2005 May 27;96(10):77-82.38-40).
36. Parlakian A, Charvet C, Escoubet B, Mericskay M, Molkentin J D, Gary-Bobo G et al. Temporally controlled onset of dilated cardiomyopathy through disruption of the SRF gene in adult heart. Circulation. 2005;112(19):2930-9.
37. Parlakian A, Tuil D, Hamard G, Tavernier G, Hentzen D, Concordet J P, et al. Targeted inactivation of serum response factor in the developing heart results in myocardial defects and embryonic lethality. Mol Cell Biol. 2004; 24(12):5281-9.
38. Balza R O Jr, Misra R P. Role of the serum response factor in regulating contractile apparatus gene expression and sarcomeric integrity in cardiomyocytes. J Biol Chem. 2006 Mar. 10;281(10):6498-510.
39. Iyer D et al. Serum response factor MADS box serine-162 phosphorylation switches proliferation and myogenic gene programs. Proc Natl Acad Sci USA 103(12):4516.

Example Section 3

Identification of Novel SRF Target Genes in Response to Mild Overexpression of Serum Response Factor in Mouse Hearts Introduction It is well appreciated that the mammalian adult heart undergoes a number of changes with advancing age (36, 52, 53). Recent studies indicate that one of the key transcription factors, serum response factor (SRF), plays an important role in the regulation of cardiac genes during development and adult aging (4, 25, 51, 59, 61). SRF is a member of MADS (MCM1, Agamous, Deficiens, SRF) family of transcription factors that regulates the genes that are usually considered to be immediate-early genes and muscle-related genes (29, 48). SRF also serves to regulate cell proliferation, cell size, and cell survival (35, 40, 54, 61).

SRF regulates its target genes by binding to the cognate response element, the serum response element (SRE), which contains a consensus sequence of CC(A/T)6GG also known as the CArG box (5, 12, 45, 47). In addition, SRF also regulates the gene promoters containing the "CArG-like" elements that have only a single base mismatch from the classic CArG box (29, 62). It has been estimated that hundreds of SRF target genes that contain CArG and/or CArG-like motifs may exist in both mouse and human genomes (30). It remains a challenge to identify these unknown SRF target genes, and to define their roles in the heart.

The level of SRF expression increases by approximately 20% from the age of 3 months to 20 months (from young adulthood to early senescence) in rodent hearts (25, 59). It is plausible that this increased SRF might contribute to altered expression of SRF target genes, thereby affecting cardiac function in aged mice. In our previous study, we reported the generation and characterization of transgenic mice with mild cardiac-specific SRF overexpression of approximately 40-50% (59). Mild overexpression of SRF produced cardiac changes similar to that of senescence in the young adult transgenic mice. By 6 months of age, the hearts of young adult transgenic mice had changes that usually appear later, at around 20 months or later, which include mild cardiomyocyte hypertrophy, cardiac fibrosis and mildly increased left ventricular wall thickness. The cardiac functional changes, including a 20% reduction in early diastolic LV filling (peak E) and a 35% decline in peak E-to-peak-A (late diastolic filling) ratio, are similar to those seen clinically in late life as part of human adult myocardial aging (10, 19, 59). It appeared likely that SRF target genes may have contributed to the cardiac phenotype in this model of myocardial aging (59).

To determine the response in vivo of SRF target genes to SRF regulation, we examined the cardiac gene profile of transgenic mouse hearts with SRF overexpression. We found that the expression of 207 cardiac genes was significantly altered in the transgenic mice compared to their non-transgenic littermates. Bioinformatics analysis of the promoter of 207 genes revealed that approximately 93% (192 of 207) of them contained CArG and/or CArG-like elements in the promoter region. These genes encode a broad spectrum of proteins involved in multiple functions including metabolism, cytoskeleton, transcription and translational regulation, extracellular matrix, ion transport, stress response, as well as protease and protease inhibitors. Our data showed that mild overexpression of SRF repressed a majority (65%) of the SRF target genes, and activated a minority (35%) of them. These data demonstrate that SRF is a transcription factor that can have repressive as well as activating effects on many SRF target genes in the mouse heart.

Experimental Procedures

Transgenic Mouse with Mild Cardiac-specific Overexpression of SRF.

The generation and characterization of transgenic mice with mild cardiac-specific overexpression of SRF was previously reported (59). At 6 months of age, the transgenic mice manifested cardiac changes suggestive of an "aged heart" (59). Therefore, 6-month-old transgenic and non-transgenic mice were used in this study.

The studies were conducted with Institutional Review Board approval from the University of Arkansas for Medical Sciences, and in accordance with the NIH Guiding Principles for Research Involving Animals.

Total RNA Isolation, GeneChip Hybridization and Preliminary Data Analysis.

Total RNA was isolated from the cardiac ventricles of the transgenic and non-transgenic mice as previously described (61). The total RNA preparations were then subjected to a purification procedure using RNeasy Mini Spin Columns (Qiagen). The total RNA preparations from five animals were pooled per group. Each sample from one group was hybridized to an independent GeneChip MGU74Av2 (Affymetrix). The GeneChip hybridization and preliminary data analysis were performed according to the standard procedures at the Genomic Center at Beth Israel Deaconess Medical Center in Boston (17).

Microarray Data Analysis.

The microarray data analysis and data interpretation were performed using ArrayTrack (46). A list of differentially expressed genes (DEGs) were identified using a t-test with a combination of cut off p-value ($p<0.05$) and fold change ($FC>2$). The ArrayTrack Gene Ontology (GO) tool Gene Ontology for Function Analysis (GOFFA) was subsequently applied to the DEGs for biological interpretation (2, 43). The statistical significance of a GO term was determined using Fisher's Exact Test. Furthermore, the GOPath and TreePrune in GOFFA were also used to identify significant biological functions based on the DEGs. In addition to GOFFA analysis, DEGs were also analyzed in canonical pathway maps using GeneGo MetaCore. Experimental data are visualized as red/blue thermometers pointing up/down, and signifying up/down-regulation of the map objects. Each edge or link on the network is based on experimental data referenced in the corresponding literature (The legend for MetaCore Networks may be viewed in Table S5).

Validation of the Array Data: Real Time PCR

Validation of the Affymetrix data was performed by qPCR analysis with the ABI PRISM 7700 Sequence Detection System (Applied Biosystem, CA) with standard procedure at the Real-time PCR core facility on the campus. Below is the list of primers used in the study:

```
ANF: (+)
                                       (SEQ ID NO: 38)
5'-GTGTACAGTGCGGTGTCCAA-3',

ANF: (-)
                                       (SEQ ID NO: 7)
5'-ACCTCATCTTCTACCGGCATC-3';

α-MHC: (+)
                                       (SEQ ID NO: 16)
5'-TGTGGTGCCTCGTTCCA-3',

α-MHC: (-)
                                       (SEQ ID NO: 17)
5'-TTTCGGAGGTACTGGGCTG-3';

β-MHC: (+)
                                       (SEQ ID NO: 18)
5'-GCATTCTCCTGCTGTTTCCTT-3',

β-MHC: (-)
                                       (SEQ ID NO: 19)
5'-TGGATTCTCAAACGTGTCTAGTGA-3';

Cardiac Actin (+)
                                       (SEQ ID NO: 20)
5'-GGAGAAGATCTGGCACCATACATT-3',
```

```
Cardiac Actin (-)
                                       (SEQ ID NO: 21)
5'-AGCAGGGTTGGGTGTTCCT-3';

Skeletal Actin (+)
                                       (SEQ ID NO: 22)
5'-GGGCTGTGTTCCCATCCAT-3', Skeletal Actin (-)
                                       (SEQ ID NO: 23)
5'-AGGAGTCCTTCTGACCCATACCT-3';

SRF (+)
                                       (SEQ ID NO: 24)
5'-CAAACTGCAGCCCATGATCA-3',

SRF (-)
                                       (SEQ ID NO: 25)
5'-CGGAGAGTCTGGCGAGTTG-3';

SERCA2 (+)
                                       (SEQ ID NO: 26)
5'-GGCAAGATCCGGGATGAAAT-3',

SERCA2 (-)
                                       (SEQ ID NO: 27)
5'-CCCCAAACTCGTCTAGCTTCTG-3';
```

Analysis of Classic CArG and CArG-like Motifs in the Gene Promoter

Figure 16:
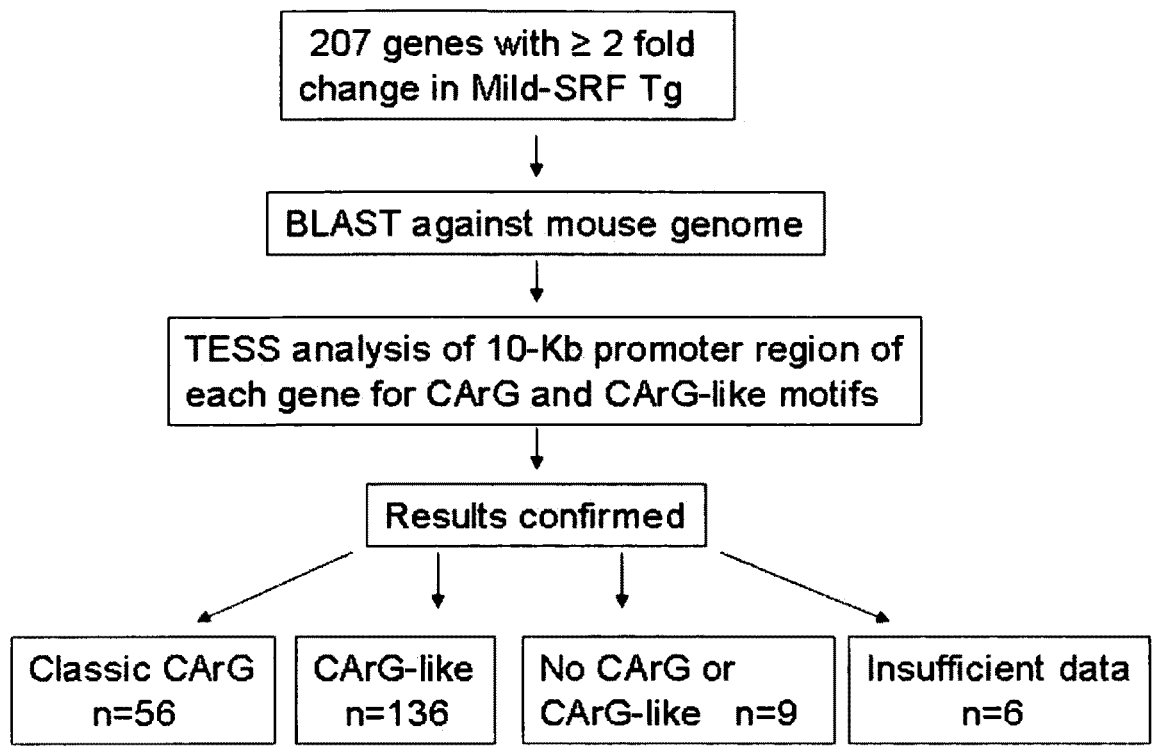
FIG. 16: Flow diagram showing method of defining CArG and/or CArG-like elements of 207 genes that were identified to be differentially regulated in the hearts of 6 month old Mild-SRF transgenic mice. The mRNA sequence of each gene was submitted to BLAST and the 10-kb promoter region was identified. Next the data were analyzed using Transcription Element Search (TESS). The results were confirmed using alignment software to identify either classic CArG or CArG-like motifs in the promoter regions (see text in methods section for details).

The criteria for the classic CArG motif is a 10-bp element that has the sequence CC(A/T)6GG and CArG-like element has a single base mismatch from its classic counterpart (29). Briefly, the mRNA sequences were obtained from the RefSeq database for most of the 207 genes; the mRNA sequences were also obtained from GenBank database for several genes that did not have reference sequences in the RefSeq database as of September 2007. The reference mRNA sequences were submitted to BLAST for comparison with the mouse genomic DNA sequence in the mouse genome database. After noting the orientation of the alignment, the appropriate 10-Kb genomic DNA sequence upstream from the transcription start point corresponding to the promoter region of each gene was isolated and analyzed using a web-based bioinformatics tool TESS at www.cbil.upenn.edu/cgi-bin/tess/tess. Because TESS results are model-based, the potential CArG and CArG-like sequences were verified by both using LALIGN (www.ch.embnet.org/software/LALIGN_form.html) and visual confirmation (FIG. 16).

Figure 17:
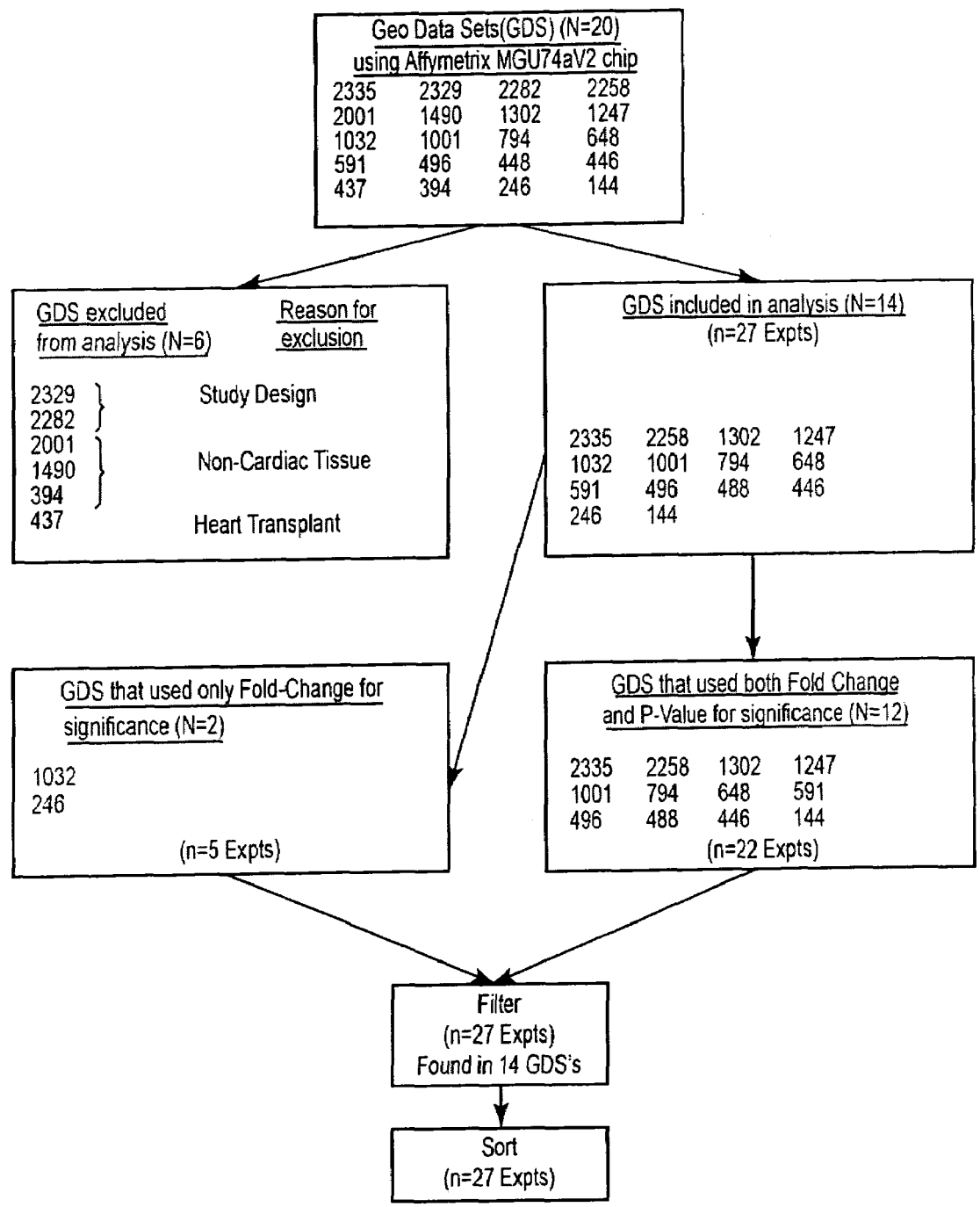
FIG. 17: Outline of the procedure used in comparing the results of expression of genes containing classic CArG boxes found in the Mild-SRF transgenic hearts with that in other cardiac microarray literature as depicted in Table 3. The GEO database was searched for gene expression data from experiments using mice utilizing the same Affymetrix gene chip as used in our experiment (MGU74aV2), and 20 GEO Data Sets (GDS) were found. Out of the 20 GDS, 6 were excluded from analysis because of difference in tissue (neural, skeletal, transplant), difference in experimental design or acute stress (acute myocardial infarction). Excluding those six GDS's, 14 remained, which included data from 27 different experiments on the hearts (some using different time points or dosages in the same study). These 27 experiments represented cardiac remodeling or hypertrophy due to over-expression of genes or stress (whether due to ischemia, exercise, or pressure overload). These GDS's were analyzed for changes in gene expression with either a significant fold change of ±1.5 and p<0.05 or, if p value was not available, a minimum fold change of ±2 (See Table S2 and S3). These genes were sorted in rank order form to compare with the classic CArG box containing genes in the Mild-SRF transgenic hearts (See Table 3).

Comparison of SRF Target Gene Expression of Mild-SRF Transgenic Mice with Other Mouse Models The expression of 207 genes in mild-SRF transgenic mice was compared with those of microarray results available online at the Gene Expression Omnibus (GEO, www.ncbi.nlm.nih.gov/geo/). The GEO database was searched for expression data from experiments using mouse hearts on the Affymetrix MGU74aV2 chip (GPL81, www.ncbi.nlm.nih.gov/geo/query/acc.cgi?acc=GPL81). Twenty GEO Data Sets (GDS's) were found. Of these, fourteen were analyzed for differential expression by fold-change and/or P-value (two-tailed T-test). The lists of differentially expressed genes were combined and filtered with our list of 207 SRF target genes. Fold-change and P-value results were tested at either +/−2-fold or +/−1.5-fold and P<0.05. Columns and rows were sorted so that the most commonly differentially expressed genes were toward the top, and the experimental systems with the most genes in common with mild overexpression of SRF were toward the left (FIG. 17).

Results

1. Mild Overexpression of SRF Altered Many Cardiac Genes in vivo.

Figure 18:
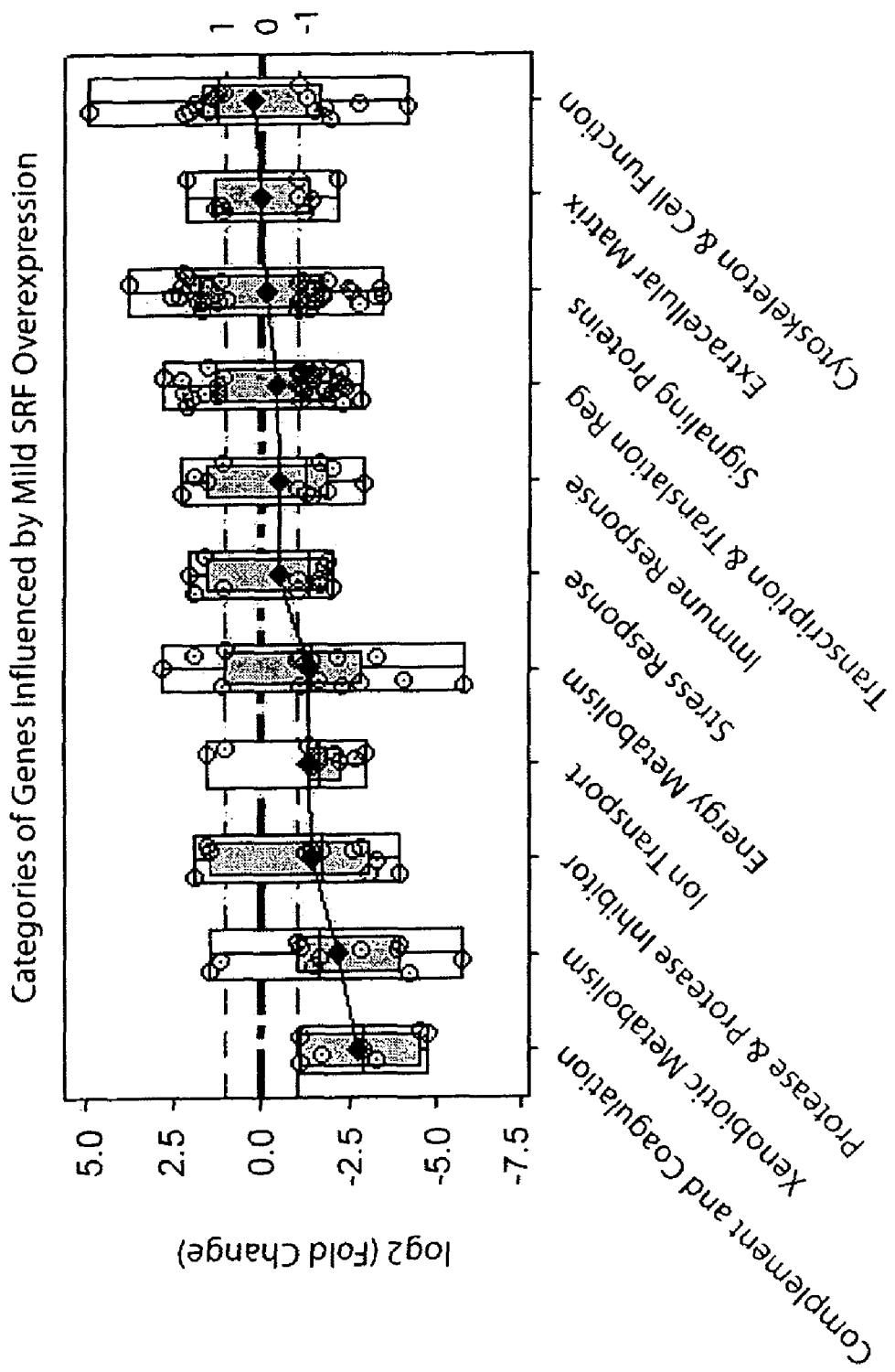
FIG. 18: A box-plot of the magnitude of change in gene expression (log 2) in the Mild-SRF transgenic distributed among 12 different functional categories (category of "other proteins" not shown). Each gene is represented by a small circle. White boxes depict the range limits, and the light gray boxes, the inter-quartile range. The diamonds represent the means and are joined by a solid line. The categories are displayed from the most down-regulated (on the left) to the most up-regulated (on the right). Note that in the ytoskeletal category more genes are upregulated than down-regulated.
Figure 19A:
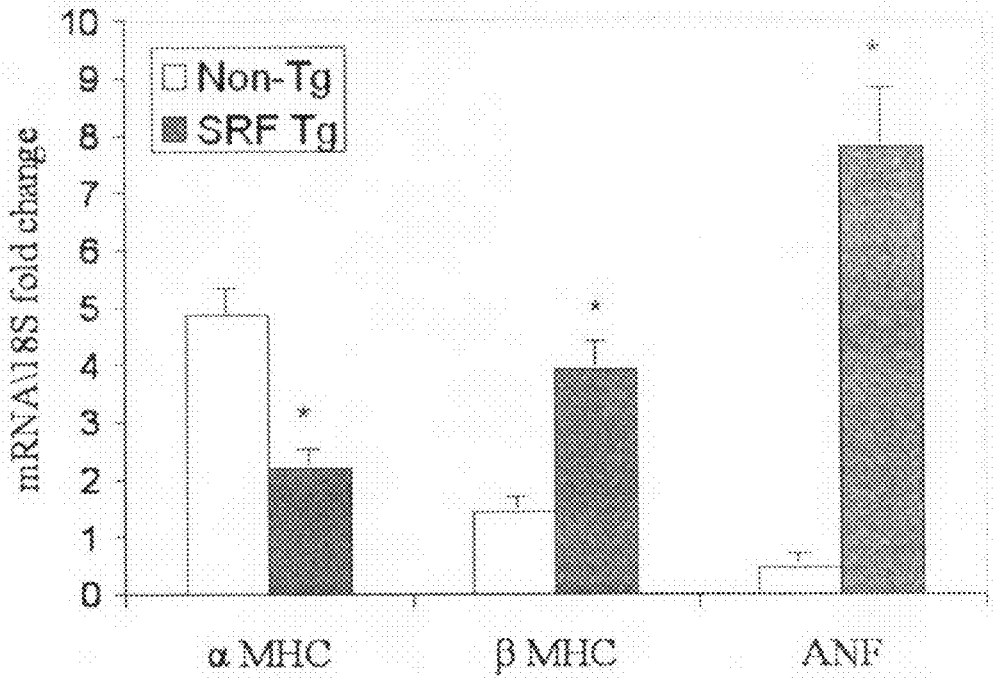
FIG. 19: The expression of cardiac genes in 6 month old Mild-SRF transgenic (Tg) and Non-transgenic (Non-Tg) was validated by real-time RT-PCR. Examples of results are given as a relative expression of fold-change in gene expression, with mRNA normalized to 18S housekeeping gene. *p<0.05 Non-Tg, vs SRF Tg using the Mann Whitney U test. x axis: MYH7=myosin heavy chain 7; NPPA=natriuretic peptide protein A.
Figure 19B:
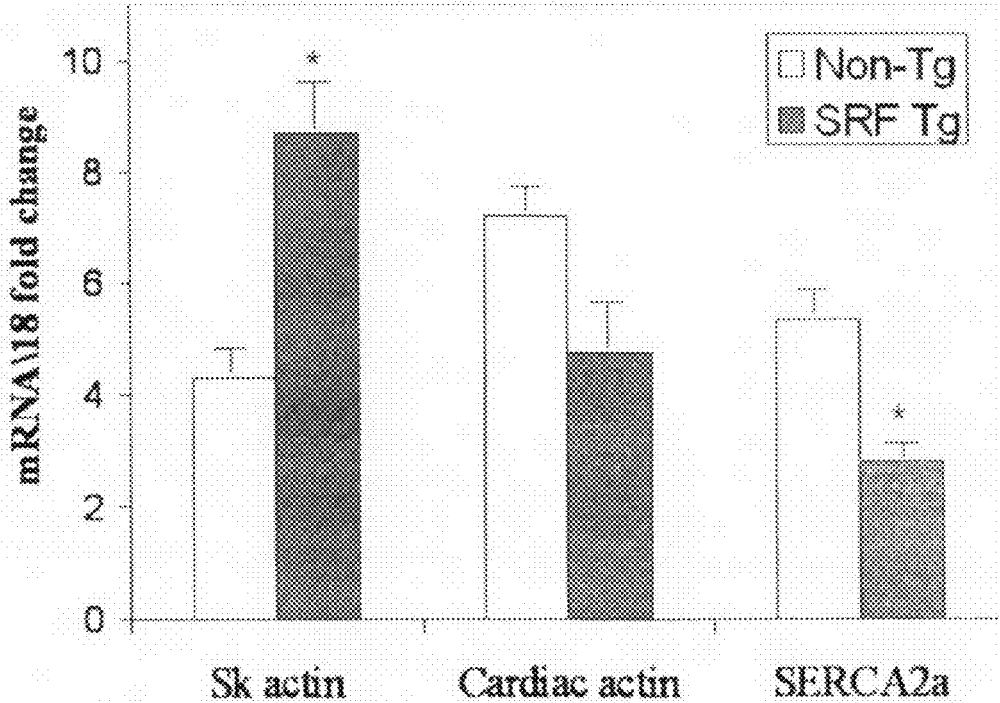

To examine the impact of mild overexpression of SRF on cardiac gene expression and to explore the potential mechanism underlying the functional changes resembling cardiac aging, microarray analysis was performed using mouse hearts from the 6-month-old transgenic mice and non-transgenic littermates. The expression of 207 cardiac genes was significantly altered in the transgenic mice compared to non-transgenic mice (see Table 20). We consider all 207 of these genes as "SRF target genes". Among them, 65% (135 of 207) of the genes were down-regulated, whereas 35% (72 of 207) of the genes were up-regulated, indicating that increased SRF expression repressed the expression of the majority of cardiac genes (FIG. 18). The expression of several genes was verified by Real-time PCR (FIG. 19).

2. Most of the Genes that were Significantly Impacted by Mild Overexpression of SRF Contained CArG and/or CArG-like Elements.

To examine whether SRF activated or repressed its target genes that contain CArG and/or CArG-like elements within their promoter regions, we further analyzed transcriptional sites within the 10-Kb promoter region in each of the 207 genes. The classic CArG element was defined as a 10-bp DNA sequence with "CC(A/T)6GG", and the "CArG-like" element was defined as a 10-bp sequence with only one substitution from the consensus sequence. As shown in the flow diagram in FIG. 16, CArG and CArG-like elements within the 10-Kb promoter region of each gene was analyzed and verified by using web-based software program TESS and LALIGN (41) (see details in "experimental procedures"). The existence of one or more of either a CArG or a CArG-like element in the promoter sequence of each of the 207 genes was visually confirmed.

Most of the genes that were significantly impacted by mild overexpression of SRF contained CArG and/or CArG-like elements. As shown in FIG. 20, approximately 93% (192 of 207) of the cardiac genes that responded significantly to SRF overexpression contained CArG and/or CArG-like elements. Roughly 29% (56 of 192) of the SRF target genes contained at least one classic CArG element, while 71% (136 of 192) of them had at least one CArG-like element. Of those 56 genes with a classic CArG element, approximately 79% (44 of 56) also contained at least one CArG-like element. Many of these genes have not been previously reported as SRF target genes (FIG. 20).

In addition, mild overexpression of SRF repressed 65% (124/192) and activated 35% (68/192) of the SRF target genes. These data indicate that SRF both represses and activates genes containing CArG and/or CArG-like elements.

3. Mild Overexpression of SRF Affected SRF Target Genes in Multiple Functional Categories.

To assess the significance of altered expression of SRF target genes on cardiac function, the 207 SRF target genes were grouped into 12 categories according to their function and Gene Ontology (GO) term. They are energy metabolism, xenobiotic metabolism, cytoskeleton, transcription and translation regulation, extracellular matrix, stress response, signaling proteins, protease and protease inhibitors, complement and coagulation, ion transport, immune response as well as other proteins (Table 3, FIG. 18). The 192 genes that contain CArG and/or CArG-like elements were distributed among all of the 12 categories. The 56 genes that contain at least one classic CArG element were also found in all except one of the 12 categories (Complement and Coagulation) (Table 3).

Mild overexpression of SRF down-regulated a majority of the genes in 10 categories, but up-regulated most of the genes in the cytoskeleton and cellular function category. An equal number of genes in the ECM category were up-regulated and down-regulated. Mild SRF overexpression not only changed the expression of cytoskeletal genes but also changed the expression of many genes in other functional categories. For instance, several ECM genes were up-regulated, which include type I collagen, fibulin and biglycan. Serpine1/PAI-1, which inhibits the degradation of ECM proteins, was also up 2.9-fold. Changes were also observed in genes that play a regulatory role in cardiac hypertrophy and fibrosis, such as TGF-beta3 (up 3-fold); CTGF, which promotes fibroblast proliferation and myocyte growth, was increased by 4-fold. GDF15, a member of TGF-beta superfamily and a potential biomarker for cardiac disease, was up 14-fold (18). Periostin, which regulates collagen I fibrillogenesis, was elevated over 4-fold (32, 33). Annexins (ANXs) are a large group of calcium-binding proteins participating in diverse important biological processes (7, 24). In the mild-SRF transgenic mouse heart, annexin a10 was up by more than 30-fold.

Alteration was also observed in the expression of genes involved in proteolysis. Ubiquitin specific peptidase 29 (USP29) was up 3.7-fold. Dipeptidyl peptidase 7 (DPP7), was up 2.7-fold. Spink3, a Kazal type 1 serine peptidase inhibitor, was down 2.5-fold. Serpina1a, a member of serine/cysteine peptidase inhibitors, was down 16-fold. Alpha-2-thiol proteinase inhibitor (Kng1) was down 29-fold.

Mild overexpression of SRF also changed the expression of genes regulating energy metabolism. For example, phosphofructokinase, a key enzyme that controls the pace of glycolysis was elevated over 2-fold. The genes that regulate fatty acid metabolism were decreased. Solute carrier family 27 (slc27a1), which catalyzes the transfer of long-chain fatty acids across the plasma membrane, was down 2-fold (39). Lipase, which catalyzes the rate-limiting step in adipose tissue lipolysis, was down 2-fold (23). Elongase 2 (Elovl2), which performs the first regulatory step (condensation) in the elongation cycle in fatty acid synthesis, was down 5-fold (15). Esterase 1 (Es-1), which hydrolyzes a variety of esters including fatty acid esters of estradiol, was down 17.5-fold. Coenzyme A synthase was decreased 2.2-fold.

Interestingly, several ion regulation genes were found to be SRF target genes. For instance, several ion transport genes were down-regulated. ATP1a1 was down 3-fold, slc4a8 was down 2.5-fold, TRPM7 was down 3-fold, KCNQ2 was down 3-fold, and Sodium/bile acid co-transporter (slc10a) was down 8-fold. Aqp4, a gene involved in water transport, was down 5-fold. Casq1, a calcium handling protein, was up 2.8-fold. The histidine rich calcium binding protein (HRC), which interacts with SERCA2, was down 2.8-fold (1).

Our data also revealed that SRF impacted the genes involved in transcriptional and translational regulation. The genes that were up-regulated include distal-less homeobox 5 (4.8-fold), activating transcription factor 3 (ATF3, up 4.5-fold), TATA box binding protein (TBP, up 3.8-fold), and four and a half lim domains 1 (Fhl1, up 3-fold), Id2, which forms heterodimer with other HLH proteins, was up 2.3-folds. The down-regulated genes include Six3 (down 2-fold), Gtf3c4 (down 2.6-fold), Lhx8 (down 2-fold), Hmx1 (down 2.2-fold), Sp4 (down 2.6-fold), and E2F3 (down 5-fold). The proprotein convertase (PCSK5), which mediates post-translational endoproteolytic processing for several integrin alpha subunits, was down 2.7-fold.

4. Altered Expression of SRF Target Genes was Also Observed in Other Mouse Models.

To examine whether the SRF target genes listed in FIG. 20 might be differentially regulated in other mouse models, cardiac gene expression data from 14 databases representing 27 experiments using various mouse models in the Gene Expression Omnibus (GEO) database were compared with that of the mild-SRF transgenic mice in the present study (see details in "Experimental procedure"). Altered expression of 194 SRF target genes was observed in the other mouse models. Among them, most of the 56 genes that contained classic CArG elements were also observed in the other mouse models (Table 3), suggesting that the SRF target genes are actively regulated in response to the various physiological and pathological stimuli. The SRF target genes with at least one classic CArG element that were also frequently observed in other mouse models include Postn, Ift81, Emp1, Fhl 1, Tpm2, Il 15, Irf8, Myh4, Emr1, Nppa, Aqp4, R3hcc1, and Myh7.

TABLE 3

Functional categories of SRF target genes.

| Category | CArG | CArG-like | No CArG, CArG-like, or insufficient data |
|---|---|---|---|
| Energy Metabolism | 4 | 10 | 1 |
| Xenobiotic Metabolism | 4 | 7 | |
| Cytoskeleton | 8 | 9 | |
| Transcription & Translation Regulation | 7 | 20 | 3 |
| Extracellular Matrix | 2 | 10 | |
| Stress Response | 2 | 10 | |
| Signalling Proteins | 7 | 24 | 2 |
| Proteases and Protease Inhibitors | 5 | 6 | |
| Complement and Coagulation | 0 | 6 | 1 |
| Ion Transport | 3 | 8 | |
| Immune Response | 1 | 6 | 4 |
| Other Proteins | 13 | 20 | 4 |
| Total | 56 | 136 | 15 |

Each of the 207 SRF target gene was assigned to one of 12 categories. 56 genes contained classic CArG element, 136 genes contained CArG-like element, 15 genes did not have both elements, or there are not sufficient data to show that they had either element. Of 207 genes, 72 were up-regulated and 135 down-regulated (see text).

The above gene expression data were also compared with that of the mild SRF transgenic to determine whether they were changed in the same or opposite direction. It was found that at all time points after myocardial infarction, the direction of change of those genes that were differentially expressed in both the myocardial infarction model and in mild SRF transgenic was very similar (one hour: 11 of 12 genes, four hours: 13 of 14 genes, one day: 7 of 8, seven days: 26 of 29 genes, 8 weeks: 9 of 13). In transverse aortic constriction models, 7 of 8, 14 of 32, and 17 of 19 genes were differentially expressed in the same direction as that in mild SRF transgenic at two, ten, and twenty-one days, respectively. In mice with overexpression of TNF alpha the direction of differential expression was found to be the same as that in mild SRF transgenic in 52 of the 67 genes that were differentially expressed in both models. In double-transgenic mice over-expressing IGF-1R and a dominant negative form of PI3K (IGF-1R, PI3K−/−), 17 of the 19 genes that were differentially expressed in both models were expressed in the double transgenic in the opposite direction to that of mild SRF transgenic mice.

We also utilized "GeneGo", a bioinformatics and data mining application in systems biology, to determine which signaling networks were affected in our model. For example, we observed that TGF-beta, Wnt and cytokine remodeling were among the pathways that were significantly impacted in the mild-SRF transgenic mouse hearts (data not shown).

Discussion

This study has several major findings. A set of 207 SRF target genes and their in vivo response to SRF regulation in the heart has been identified. Among them, 192 genes have CArG and/or CArG-like elements in their promoter regions. Based on its function and Gene Ontology term, each SRF target gene was assigned to one of the 12 functional categories. Overexpression of SRF repressed 65% of the SRF target genes. The gene profile revealed that in mild-SRF transgenic hearts, cardiac energy metabolism shifted toward carbohydrate metabolism with reduced fatty acid metabolism. It also revealed decreased expression of many genes that regulate transcriptional activity, stress response, protein turnover and ion regulation. However, the expression of cytoskeletal genes was considerably increased. Changes in cardiac gene expression are similar to those that are observed during adult aging. Our findings demonstrate that SRF has both repressive and activating effects on cardiac gene expression, and that an elevation of SRF protein level in typical aging in rodents may contribute to the altered cardiac structure and function observed during aging (59).

Since the discovery of the SRF protein, many SRF target genes have been identified. Recently, several groups have identified a number of SRF target genes, in which CArG and CArG-like elements are found in promoter region, intron or 3'-untranslated region (34, 44, 58. The effect of SRF on gene expression has been studied both in vitro and in vivo. The in vitro transfection assay with cell lines has been frequently utilized to study the effect of SRF on the expression of a number of SRF target genes (50, 58). Since many cell lines that are used in the assay may not have the same SRF cofactors as that in cardiac myocytes and fibroblasts, the experimental data in cell lines may differ from that in the intact heart. The mild-SRF transgenic mouse provides us with a specific tool to identify SRF target genes and to study the response to cardiac SRF overexpression in vivo. It is not surprising that 93% of the cardiac genes that responded significantly to SRF overexpression contained CArG and/or CArG-like elements in their promoters. With the increasing number of novel SRF target genes being uncovered, a broad list of categories such as the one used in this study is needed to reflect the multiple functions of SRF target genes.

The down-regulation of a majority of SRF target genes and up-regulation of a minority of SRF target genes in the present study support the notion that SRF-dependent gene regulation is complex. SRF target genes are regulated by multiple transcription regulators including SRF, SRF cofactors, SRF isoforms and a number of microRNA (40-42). Other mechanisms include nonsense-mediated mRNA decay (60).

In the heart, energy usually comes from beta-oxidation of fatty acids and glycolysis, the proportion of which changes during different stages of life. During fetal life, myocardial ATP is derived predominantly from glycolysis and lactate oxidation. After birth, a rapid increase in fatty acid oxidation occurs along with a decline in glycolytic and lactate oxidative rates (27). In the healthy adult heart, about 60-90% of the ATP generation in the mitochondria comes from beta-oxidation of fatty acids, and the rest comes from pyruvate that is derived from glycolysis and lactate (42). A decline in fatty acid oxidation together with an increase in carbohydrate metabolism has been observed in the senescent heart (21, 38, 49). The changes of gene expression in aged heart include an up-regulation of phosphofructokinase, an allosteric enzyme that controls the rate of glycolysis by converting fructose 6-phosphate to fructose 1,6-bisphosphate, and down-regulation of solute carrier family 27 (slc27a1), which catalyzes the transfer of long-chain fatty acids across the plasma membrane (21, 39). In the mild-SRF transgenic heart, the up-regulation of phosphofructokinase together with down-regulation of several proteins, including solute carrier family 27 (slc27a1) (39), carnitine acetyltransferase (16), long-chain acyl-CoA synthetase 1 (ASCL1) (9), lipase, and elongase 2 (Elovl2) (15), indicate that a reduction in fatty acid metabolism also occurred in this model. Thus, it is likely that SRF overexpression contributed to the altered energy metabolism in the mild-SRF transgenic heart.

In the present study, we observed that several ion regulation proteins are influenced by SRF. Altered expression of these proteins can cause cardiac arrhythmias and also affect mechanical performance. The expression level of Na+,K+-ATPase has been reported to correlate with left ventricular function (6). Altered expression of several other proteins that are involved in the calcium handling, including SERCA2a, calsequestrin 1 and CAMK2a was also observed in the mild-SRF transgenic heart. These alterations may account for the observed functional changes in the mild-SRF transgenic mouse model (59).

SRF overexpression in the heart changed the expression of a group of genes involved in transcriptional and translational regulation. Altered expression of TATA box binding protein and the subunit of general transcription factor are likely to affect the transcriptional initiation and efficiency, while altered expression of the subunit 3 of eukaryotic translation initiation factor 2 is likely to affect the translational process. Altered expression of several ribosomal proteins including ribosomal protein S4, S12, S17, and L34 are likely to affect mRNA splicing, ribosome assembly, translational fidelity and protein synthesis (14, 56). Altered expression of ribonucleotide reductase ml and thymidine kinase 1 could affect DNA synthesis and repair, nucleotide metabolism as well as cell-cycle progression (55).

During the typical aging process, most components of the cardiovascular system undergo gradual change, including a progressive loss of myocytes with subsequent hypertrophy of the remaining viable myocytes. The net result is a change in the ratio of myocytes to fibroblasts. As myocytes are lost and fibroblasts continue to divide and produce collagen, the physical properties of the aging heart become altered (52). From the point of view of molecular biology, a "selective" decline in the gene expression is a common feature of aging in various tissues across the species (13). A number of studies have demonstrated that during adult aging a majority of the genes are decreased in various tissues, including oocytes, kidney, monocytes, prostate, and heart (3, 11, 20, 26, 28, 37). However, expression of a minority of the genes is actually increased with age. For instance, a number of cytoskeletal and ECM proteins are usually increased in both the old human and rodent hearts (49). Therefore, the altered gene expression observed during aging is not purely compensatory, but is dynamic and well-regulated (13).

Comparing our data from mild-SRF transgenic mice with those in aged mice in the literature, it is found that they share similarities in terms of cardiac gene expression (22, 49). Similar to that in aged mice, the majority of cardiac genes in most of the functional categories were decreased, whereas cytoskeletal genes were increased in the transgenic mice. Some well studied ECM proteins, including collagen I were also significantly increased in the present model (mild-SRF transgenic) as well as in old age. Taken together, our findings demonstrate that the elevation of SRF protein level that is observed in the heart during typical aging in rodents may have a major impact on many cardiac genes, thereby affecting multiple aspects of cardiac structure and performance in old age.

Conclusion

To determine the in vivo effect of mildly increased SRF expression on gene regulation in the heart, we studied gene expression in a transgenic mouse model with mild cardiac-specific SRF overexpression. We identified 207 cardiac genes the expression of which were significantly altered in response to SRF regulation in vivo. Among them, 192 genes had CArG and/or CArG-like elements in the promoter region, many of which were not previously reported. We grouped these SRF target genes into 12 functional categories based on their function. The overexpression of SRF in the mouse heart repressed a majority of the SRF target genes that are important for cardiac function. For instance, cardiac energy metabolism shifted toward carbohydrate metabolism while fatty acid metabolism was reduced; the genes that are involved in transcription and ion regulation were reduced, but expression of cytoskeletal genes were increased. We found that altered expression of many SRF target genes was also present in the hearts of other mouse models, indicating that these SRF target genes are actively regulated in response to various physiological and pathological conditions. Thus, a mild elevation of SRF protein in the senescent heart may have a major impact on many SRF target genes, thereby affecting cardiac structure and performance during aging. These findings will likely enhance our understanding of SRF-dependent transcription regulation.

References

1. Arvanitis D A, Vafiadaki E, Fan G C, Mitton B A, Gregory K N, Del Monte F, Kontrogianni-Konstantopoulos A, Sanoudou D, Kranias E G (2007) Histidine-rich Ca-binding protein interacts with sarcoplasmic reticulum Ca-ATPase. Am J Physiol Heart Circ Physiol 293:H1581-9
2. Ashburner M, Ball C A, Blake J A, Botstein D, Butler H, Cherry J M, Davis A P, Dolinski K, Dwight S S, Eppig J T, Harris M A, Hill D P, Issel-Tarver L, Kasarskis A, Lewis S, Matese J C, Richardson J E, Ringwald M, Rubin G M, Sherlock G (2000) Gene ontology: tool for the unification of biology. The Gene Ontology Consortium. Nat Genet 25:25-29
3. Ashton K J, Willems L, Holmgren K, Ferreira L, Headrick J P (2006) Age-associated shifts in cardiac gene transcription and transcriptional responses to ischemic stress. Exp Gerontol 41:189-204
4. Barron M R, Belaguli N S, Zhang S X, Trinh M, Iyer D, Merlo X, Lough J W, Parmacek M S, Bruneau B G, Schwartz R J (2005) Serum response factor, an enriched cardiac mesoderm obligatory factor, is a downstream gene target for Tbx genes. J Biol Chem 280:11816-11828
5. Boxer L M, Prywes R, Roeder R G, Kedes L (1989) The sarcomeric actin CArG-binding factor is indistinguishable from the c-fos serum response factor. Mol Cell Biol 9:515-522
6. Bundgaard H, Kjeldsen K (1996) Human myocardial Na,K-ATPase concentration in heart failure. Mol Cell Biochem 163-164:277-283
7. Camors E, Monceau V, Charlemagne D (2005) Annexins and Ca2+ handling in the heart. Cardiovasc Res 65:793-802
8. Cen B, Selvaraj A, Burgess R C, Hitzler J K, Ma Z, Morris S W, Prywes R (2003) Megakaryoblastic leukemia 1, a potent transcriptional coactivator for serum response factor (SRF), is required for serum induction of SRF target genes. Mol Cell Biol 23:6597-6608
9. Durgan D J, Smith J K, Hotze M A, Egbejimi O, Cuthbert K D, Zaha V G, Dyck J R, Abel E D, Young M E (2006) Distinct transcriptional regulation of long-chain acyl-CoA synthetase isoforms and cytosolic thioesterase 1 in the rodent heart by fatty acids and insulin. Am J Physiol Heart Circ Physiol 290:H2480-2497
10. Grandi A M, Venco A, Barzizza F, Scalise F, Pantaleo P, Finardi G (1992) Influence of age and sex on left ventricular anatomy and function in normals. Cardiology 81:8-13
11. Hamatani T, Falco G, Carter M G, Akutsu H, Stagg C A, Sharov A A, Dudekula D B, VanBuren V, Ko M S (2004) Age-associated alteration of gene expression patterns in mouse oocytes. Hum Mol Genet 13:2263-2278
12. Hautmann M B, Madsen C S, Mack C P, Owens G K (1998) Substitution of the degenerate smooth muscle (SM) alpha-actin CC(A/T-rich)6GG elements with c-fos serum response elements results in increased basal expression but relaxed SM cell specificity and reduced angiotensin II inducibility. J Biol Chem 273:8398-8406
13. Helfand S L, Inouye S K (2002) Rejuvenating views of the ageing process. Nat Rev Genet 3:149-153
14. Herr A J, Atkins J F, Gesteland R F (2000) Coupling of open reading frames by translational bypassing. Annu Rev Biochem 69:343-372
15. Jakobsson A, Westerberg R, Jacobsson A (2006) Fatty acid elongases in mammals: their regulation and roles in metabolism. Prog Lipid Res 45:237-249
16. Jogl G, Tong L (2003) Crystal structure of carnitine acetyltransferase and implications for the catalytic mechanism and fatty acid transport. Cell 112:113-122
17. Jones J, Otu H, Spentzos D, Kolia S, Inan M, Beecken W D, Fellbaum C, Gu X, Joseph M, Pantuck A J, Jonas D, Libermann T A (2005) Gene signatures of progression and metastasis in renal cell cancer. Clin Cancer Res 11:5730-5739
18. Kempf T, Horn-Wichmann R, Brabant G, Peter T, Allhoff T, Klein G, Drexler H, Johnston N, Wallentin L, Wollert K C (2007) Circulating concentrations of growth-differentiation factor 15 in apparently healthy elderly individuals and patients with chronic heart failure as assessed by a new immunoradiometric sandwich assay. Clin Chem 53:284-291
19. Lakatta E G (2000) Cardiovascular aging in health. Clin Geriatr Med 16:419-444
20. Lau K M, Tam N N, Thompson C, Cheng R Y, Leung Y K, Ho S M (2003) Age-associated changes in histology and gene-expression profile in the rat ventral prostate. Lab Invest 83:743-757
21. Lee C K, Allison D B, Brand J, Weindruch R, Prolla T A (2002) Transcriptional profiles associated with aging and middle age-onset caloric restriction in mouse hearts. Proc Natl Acad Sci USA 99:14988-14993
22. Lee C K, Klopp R G, Weindruch R, Prolla T A (1999) Gene expression profile of aging and its retardation by caloric restriction. Science 285:1390-1393
23. Li Z, Sumida M, Birchbauer A, Schotz, M C, Reue K (1994) Isolation and characterization of the gene for mouse hormone-sensitive lipase. Genomics 24:259-265.
24. Liu S H, Lin C Y, Peng S Y, Jeng Y M, Pan H W, Lai P L, Liu C L, Hsu H C (2002) Down-regulation of annexin A10 in hepatocellular carcinoma is associated with vascular invasion, early recurrence, and poor prognosis in synergy with p53 mutation. Am J Pathol 160:1831-1837
25. Lu X G, Azhar G, Liu L, Tsou H, Wei J Y (1998) SRF binding to SRE in the rat heart: influence of age. J Gerontol A Biol Sci Med Sci 53:B3-10

26. Maes O C, Xu S, Yu B, Chertkow H M, Wang E, Schipper H M (2007) Transcriptional profiling of Alzheimer blood mononuclear cells by microarray. Neurobiol Aging 28:1795-1809
27. Makinde A O, Kantor P F, Lopaschuk G D (1998) Maturation of fatty acid and carbohydrate metabolism in the newborn heart. Mol Cell Biochem 188:49-56
28. Melk A Mansfield E S, Hsieh S C, Hernandez-Boussard T, Grimm P, Rayner D C, Halloran P F, Sarwal M M (2005) Transcriptional analysis of the molecular basis of human kidney aging using cDNA microarray profiling. Kidney Int 68:2667-2679
29. Miano J M (2003) Serum response factor: toggling between disparate programs of gene expression. J Mol Cell Cardiol 35:577-593
30. Miano J M, Long X, Fujiwara K (2007) Serum response factor: master regulator of the actin cytoskeleton and contractile apparatus. Am J Physiol Cell Physiol 292:C70-81
31. Niu Z, Li A, Zhang S X, Schwartz R J (2007) Serum response factor micromanaging cardiogenesis. Curr Opin Cell Biol 19:618-627
32. Norris R A, Damon B, Mironov V, Kasyanov V, Ramamurthi A, Moreno-Rodriguez R, Trusk T, Potts J D, Goodwin R L, Davis J, Hoffman S, Wen X, Sugi Y, Kern C B, Mjaatvedt C H, Turner D K, Oka T, Conway S J, Molkentin J D, Forgacs G, Markwald R R (2007) Periostin regulates collagen fibrillogenesis and the biomechanical properties of connective tissues. J Cell Biochem 101:695-711
33. Oka T, Xu J, Kaiser R A, Melendez J, Hambleton M, Sargent M A, Lorts A, Brunskill E W, Dorn G W 2nd, Conway S J, Aronow B J, Robbins J, Molkentin J D (2007) Genetic manipulation of periostin expression reveals a role in cardiac hypertrophy and ventricular remodeling. Circ Res 3;101:313-321
34. Philippar U, Schratt G, Dieterich C, Muller J M, Galgoczy P, Engel F B, Keating M T, Gertler F, Schule R, Vingron M, Nordheim A (2004) The SRF target gene Fhl2 antagonizes RhoA/MAL-dependent activation of SRF. Mol Cell 16:867-880
35. Poser S, Impey S, Trinh K, Xia Z, Storm D R (2000) SRF-dependent gene expression is required for P13-kinase-regulated cell proliferation. EMBO J 19:4955-4966
36. Pugh K G, Wei J Y (2001) Clinical implications of physiological changes in the aging heart. Drugs Aging 18:263-276
37. Rysa J, Leskinen H, Ilves, Ruskoaho H (2005) Distinct upregulation of extracellular matrix genes in transition from hypertrophy to hypertensive heart failure. Hypertension 45:927-933
38. Sample J, Cleland J G, Seymour A M (2006) Metabolic remodeling in the aging heart. J Mol Cell Cardiol 40:56-63
39. Schaffer J E, Lodish H F (1994) Expression cloning and characterization of a novel adipocyte long chain fatty acid transport protein. Cell 79:427-436
40. Schratt G, Philippar U, Hockemeyer D, Schwarz H, Alberti, S, Nordheim A (2004) SRF regulates Bcl-2 expression and promotes cell survival during murine embryonic development. EMBO J 23:1834-1844
41. Schug J, Overton G C (1997) Modeling transcription factor binding sites with Gibbs Sampling and Minimum Description Length encoding. Proc Int Conf Intell Syst Mol Biol 5:268-271
42. Stanley W C, Chandler M P (2002) Energy metabolism in the normal and failing heart: potential for therapeutic interventions. Heart Fail Rev 7:115-130
43. Sun H, Fang H, Chen T, Perkins R, Tong W (2006) GOFFA: Gene Ontology For Functional Analysis—A FDA Gene Ontology Tool for Analysis of Genomic and Proteomic Data. BMC Bioinformatics 7 Suppl 2:S23
44. Sun Q, Chen G, Streb J W, Long X, Yang Y, Stoeckert C J Jr, Miano J M (2006) Defining the mammalian CArGome. Genome Res 16:197-207
45. Taylor M, Treisman R, Garrett N, Mohun T (1989) Muscle-specific (CArG) and serum-responsive (SRE) promoter elements are functionally interchangeable in Xenopus embryos and mouse fibroblasts. Development 106:67-78
46. Tong W, Cao X, Harris S, Sun H, Fang H, Fuscoe J, Harris A, Hong H, Xie Q, Perkins R, Shi L, Casciano D (2003) ArrayTrack—supporting toxicogenomic research at the U.S. Food and Drug Administration National Center for Toxicological Research. Environ Health Perspect 111:1819-1826
47. Treisman R (1986) Identification of a protein-binding site that mediates transcriptional response of the c-fos gene to serum factors. Cell 46:567-574
48. Treisman R, Ammerer G (1992) The SRF and MCM1 transcription factors. Curr Opin Genet Dev 2:221-226
49. Volkova M, Garg R, Dick S, Boheler K R (2005) Aging-associated changes in cardiac gene expression. Cardiovasc Res 66:194-204
50. Wang D, Chang P S, Wang Z, Sutherland L, Richardson J A, Small E, Krieg P A, Olson, E N (2001) Activation of cardiac gene expression by myocardin, a transcriptional cofactor for serum response factor. Cell 105:851-862
51. Wang D, Passier R, Liu Z P, Shin C H, Wang Z, Li S, Sutherland L B, Small E, Krieg P A, Olson E N (2002) Regulation of cardiac growth and development by SRF and its cofactors. Cold Spring Harb Symp Quant Biol 67:97-105
52. Wei J Y (2004) Understanding the Aging Cardiovascular System. Geriatrics and Gerontology International 4:S298-S303
53. Wei J Y (1992) Age and the cardiovascular system. N Engl J Med 327:1735-1739
54. Weinhold B, Schratt G, Arsenian S, Berger J, Kamino K, Schwarz H, Ruther U, Nordheim A (2000) Srf(−/−) ES cells display non-cell-autonomous impairment in mesodermal differentiation. EMBO J 19:5835-5844
55. Welin M, Kosinska U, Mikkelsen N E, Carnrot C, Zhu C, Wang L, Eriksson S, Munch-Petersen B, Eklund H (2004) Structures of thymidine kinase 1 of human and mycoplasmic origin. Proc Natl Acad Sci USA 101:17970-17975
56. Winkelmann D A, Kahan L, Lake J A (1982) Ribosomal protein S4 is an internal protein: Localization by immuno-electron microscopy on protein-deficient subribosomal particles. Proc Natl Acad Sci USA 79:5184-5188
57. Zaromytidou A I, Miralles F, Treisman R (2006) MAL and ternary complex factor use different mechanisms to contact a common surface on the serum response factor DNA-binding domain. Mol Cell Biol 26:4134-4148
58. Zhang S X, Garcia-Gras E, Wycuff D R, Marriot S J, Kadeer N, Yu W, Olson E N, Garry D J, Parmacek M S, Schwartz R J (2005) Identification of direct serum-response factor gene targets during Me2SO-induced P19 cardiac cell differentiation. J Biol Chem 280:19115-19126
59. Zhang X, Azhar G, Furr M C, Zhong Y, Wei J Y (2003) Model of functional cardiac aging: young adult mice with mild overexpression of serum response factor. Am J Physiol Regul Integr Comp Physiol 285:R552-560.
60. Zhang X, Azhar G, Huang C, Cui C, Zhong Y, Huck S, Wei J Y (2007) Alternative splicing and nonsense-mediated mRNA decay regulate gene expression of serum response factor. Gene 400:131-139

61. Zhang X, Chai J, Azhar G, Sheridan P, Borras A M, Furr M C, Khrapko K, Lawitts, J, Misra R P, Wei J Y (2001) Early postnatal cardiac changes and premature death in transgenic mice overexpressing a mutant form of serum response factor. J Biol Chem 276:40033-40040

62. Zilberman A, Dave V, Miano J, Olson E N, Periasamy M (1998) Evolutionarily conserved promoter region containing CArG*-like elements is crucial for smooth muscle myosin heavy chain gene expression. Circ Res 82:566-575.

All patents, patent documents, and other references cited are hereby incorporated by reference.

What is claimed is:

1. A method of identifying candidate agents to test for treating heart failure involving diastolic impairment, the method comprising:
   testing an agent in a first testing step to determine whether it (a) binds to serum response factor (SRF), (b) reduces SRF binding to a serum response element (SRE), or (c) reduces SRF protein levels in a cell;
   wherein if the agent does one or more of (a), (b), and (c), it is identified as a candidate agent; and
   providing the candidate agent for testing in a second testing step in a vertebrate model of heart failure with diastolic impairment.

2. The method of claim 1 wherein the diastolic impairment involves a reduced E/A ratio.

3. The method of claim 1 wherein the first is in vitro.

4. The method of claim 1 wherein the method comprises testing an agent to determine whether it binds to SRF.

5. The method of claim 1 wherein the method comprises testing an agent to determine whether it reduces SRF binding to an SRE.

6. The method of claim 1 wherein the method comprises testing an agent to determine whether it reduces SRF protein levels in a cell.

7. The method of claim 6 wherein the method comprises testing an agent to determine whether it reduces SRF protein levels in vivo in a vertebrate in heart tissue.

8. The method of claim 4 wherein the agent binds to SRF and is identified as a candidate agent.

9. The method of claim 5 wherein the agent reduces SRF binding to SRE and is identified as a candidate agent.

10. The method of claim 6 wherein the agent reduces SRF protein levels in a cell and is identified as a candidate agent.

11. The method of claim 1 wherein the agent is a compound of molecular weight less than 2,000.

12. The method of claim 1 wherein the agent is a peptide nucleic acid.

13. The method of claim 1 wherein the agent is a vector comprising a nucleic acid encoding a mutant SRF with at least 90% sequence identity with wild-type SRF.

14. The method of claim 1 wherein the agent is a vector comprising a nucleic acid encoding an anti-sense SRF nucleic acid.

15. A method of screening an agent for activity in treating heart failure involving diastolic impairment, the method comprising:
   (i) testing an agent to determine whether it (a) binds to serum response factor (SRF), (b) reduces SRF binding to a serum response element (SRE), or (c) reduces SRF protein levels in a cell;
   (ii) identifying a candidate agent that does one or more of (a), (b), and (c); and
   (iii) testing the candidate agent in a vertebrate model of heart failure with diastolic impairment to determine whether the candidate agent reduces one or more symptoms of heart failure with diastolic impairment.

16. The method of claim 15 wherein the vertebrate model of heart failure with diastolic impairment is a transgenic vertebrate that overexpresses SRF in cardiac tissue.

17. The method of claim 15 wherein step (iii) comprises testing to determine whether the candidate agent reduces cardiac wall thickness, increases peak E, decreases peak A, increases E/A ratio, or increases ejection fraction.

18. A method of identifying an agent for treating heart failure comprising:
   testing one or more candidate agents in a transgenic mammal whose cells comprise a recombinant nucleic acid encoding serum response factor (SRF) and whose cells overexpress serum response factor to identify an agent that reduces one or more symptoms of heart failure;
   wherein the agent that reduces one or more symptoms of heart failure (a) binds to SRF, (b) reduces SRF binding to a serum response element (SRE), or (c) reduces SRF levels in a cell.

19. A method of screening an agent for activity in treating heart failure involving diastolic impairment, the method comprising:
   (i) obtaining a candidate agent that has been shown to (a) bind to serum response factor (SRF), (b) reduce SRF binding to a serum response element (SRE), or (c) reduce SRF protein levels in a cell; and
   (iii) testing the candidate agent in a vertebrate model of heart failure with diastolic impairment to determine whether the candidate agent reduces one or more symptoms of heart failure with diastolic impairment.

* * * * *

UNITED STATES PATENT AND TRADEMARK OFFICE
CERTIFICATE OF CORRECTION

| | | |
|---|---|---|
| PATENT NO. | : 8,043,801 B2 | Page 1 of 1 |
| APPLICATION NO. | : 12/313539 | |
| DATED | : October 25, 2011 | |
| INVENTOR(S) | : Jeanne Y. Wei et al. | |

It is certified that error appears in the above-identified patent and that said Letters Patent is hereby corrected as shown below:

In column 58, line 55, claim 19 please change the (iii) to (ii) in the line: (iii) testing the candidate agent in a vertebrate model of So the line becomes:

(ii) testing the candidate agent in a vertebrate model of

Signed and Sealed this

Thirty-first Day of July, 2012

David J. Kappos
*Director of the United States Patent and Trademark Office*

SEQUENCE LISTING

```
<160> NUMBER OF SEQ ID NOS: 39

<210> SEQ ID NO 1
<211> LENGTH: 69
<212> TYPE: DNA
<213> ORGANISM: Artificial
<220> FEATURE:
<223> OTHER INFORMATION: Primer

<400> SEQUENCE: 1
ccggaagctg ttgcagccta gtccactctg ggctccaatc ctgtcaatcc taccccgaa      60 gcagctgga                                                             69

<210> SEQ ID NO 2
<211> LENGTH: 60
<212> TYPE: DNA
<213> ORGANISM: Artificial
<220> FEATURE:
<223> OTHER INFORMATION: Primer

<400> SEQUENCE: 2
tggagcaaaa cagaatggct ggctttaatg cttcaagttt tccatttcct ttccacaggg     60

<210> SEQ ID NO 3
<211> LENGTH: 60
<212> TYPE: DNA
<213> ORGANISM: Artificial
<220> FEATURE:
<223> OTHER INFORMATION: Primer

<400> SEQUENCE: 3
tcagtcatgc agagggctgg tagatgtgtt gctaacaacg cacatgcacg cacccgaaca    60

<210> SEQ ID NO 4
<211> LENGTH: 21
<212> TYPE: DNA
<213> ORGANISM: Artificial
<220> FEATURE:
<223> OTHER INFORMATION: Primer

<400> SEQUENCE: 4
acaggtggtg aacctggaca c                                               21

<210> SEQ ID NO 5
<211> LENGTH: 19
<212> TYPE: DNA
<213> ORGANISM: Artificial
<220> FEATURE:
<223> OTHER INFORMATION: Primer

<400> SEQUENCE: 5
ccattcaagt gcaccaggc                                                  19

<210> SEQ ID NO 6
<211> LENGTH: 21
<212> TYPE: DNA
```

```
<213> ORGANISM: Artificial
<220> FEATURE:
<223> OTHER INFORMATION: Primer

<400> SEQUENCE: 6
cactggagtg gcaacttcca g                                              21

<210> SEQ ID NO 7
<211> LENGTH: 21
<212> TYPE: DNA
<213> ORGANISM: Artificial
<220> FEATURE:
<223> OTHER INFORMATION: Primer

<400> SEQUENCE: 7
acctcatctt ctaccggcat c                                              21

<210> SEQ ID NO 8
<211> LENGTH: 508
<212> TYPE: PRT
<213> ORGANISM: Homo sapiens

<400> SEQUENCE: 8

Met Leu Pro Thr Gln Ala Gly Ala Ala Ala Leu Gly Arg Gly Ser
1               5                   10                  15

Ala Leu Gly Gly Ser Leu Asn Arg Thr Pro Thr Gly Arg Pro Gly Gly
            20                  25                  30

Gly Gly Gly Thr Arg Gly Ala Asn Gly Gly Arg Val Pro Gly Asn Gly
        35                  40                  45

Ala Gly Leu Gly Pro Gly Arg Leu Glu Arg Glu Ala Ala Ala Ala
    50                  55                  60

Ala Thr Thr Pro Ala Pro Thr Ala Gly Ala Leu Tyr Ser Gly Ser Glu
65                  70                  75                  80

Gly Asp Ser Glu Ser Gly Glu Glu Glu Leu Gly Ala Glu Arg Arg
                85                  90                  95

Gly Leu Lys Arg Ser Leu Ser Glu Met Glu Ile Gly Met Val Val Gly
            100                 105                 110

Gly Pro Glu Ala Ser Ala Ala Ala Thr Gly Gly Tyr Gly Pro Val Ser
        115                 120                 125

Gly Ala Val Ser Gly Ala Lys Pro Gly Lys Lys Thr Arg Gly Arg Val
    130                 135                 140

Lys Ile Lys Met Glu Phe Ile Asp Asn Lys Leu Arg Arg Tyr Thr Thr
145                 150                 155                 160

Phe Ser Lys Arg Lys Thr Gly Ile Met Lys Lys Ala Tyr Glu Leu Ser
                165                 170                 175

Thr Leu Thr Gly Thr Gln Val Leu Leu Leu Val Ala Ser Glu Thr Gly
            180                 185                 190

His Val Tyr Thr Phe Ala Thr Arg Lys Leu Gln Pro Met Ile Thr Ser
        195                 200                 205

Glu Thr Gly Lys Ala Leu Ile Gln Thr Cys Leu Asn Ser Pro Asp Ser
    210                 215                 220

Pro Pro Arg Ser Asp Pro Thr Thr Asp Gln Arg Met Ser Ala Thr Gly
225                 230                 235                 240

Phe Glu Glu Thr Asp Leu Thr Tyr Gln Val Ser Glu Ser Asp Ser Ser
                245                 250                 255

Gly Glu Thr Lys Asp Thr Leu Lys Pro Ala Phe Thr Val Thr Asn Leu
            260                 265                 270

Pro Gly Thr Thr Ser Thr Ile Gln Thr Ala Pro Ser Thr Ser Thr Thr
```

```
                275                 280                 285
Met Gln Val Ser Ser Gly Pro Ser Phe Pro Ile Thr Asn Tyr Leu Ala
            290                 295                 300

Pro Val Ser Ala Ser Val Ser Pro Ser Ala Val Ser Ser Ala Asn Gly
305                 310                 315                 320

Thr Val Leu Lys Ser Thr Gly Ser Gly Pro Val Ser Gly Gly Leu
                325                 330                 335

Met Gln Leu Pro Thr Ser Phe Thr Leu Met Pro Gly Gly Ala Val Ala
            340                 345                 350

Gln Gln Val Pro Val Gln Ala Ile Gln Val His Gln Ala Pro Gln Gln
                355                 360                 365

Ala Ser Pro Ser Arg Asp Ser Ser Thr Asp Leu Thr Gln Thr Ser Ser
            370                 375                 380

Ser Gly Thr Val Thr Leu Pro Ala Thr Ile Met Thr Ser Ser Val Pro
385                 390                 395                 400

Thr Thr Val Gly Gly His Met Met Tyr Pro Ser Pro His Ala Val Met
                405                 410                 415

Tyr Ala Pro Thr Ser Gly Leu Gly Asp Gly Ser Leu Thr Val Leu Asn
            420                 425                 430

Ala Phe Ser Gln Ala Pro Ser Thr Met Gln Val Ser His Ser Gln Val
                435                 440                 445

Gln Glu Pro Gly Gly Val Pro Gln Val Phe Leu Thr Ala Ser Ser Gly
            450                 455                 460

Thr Val Gln Ile Pro Val Ser Ala Val Gln Leu His Gln Met Ala Val
465                 470                 475                 480

Ile Gly Gln Gln Ala Gly Ser Ser Ser Asn Leu Thr Glu Leu Gln Val
                485                 490                 495

Val Asn Leu Asp Thr Ala His Ser Thr Lys Ser Glu
            500                 505

<210> SEQ ID NO 9
<211> LENGTH: 24
<212> TYPE: DNA
<213> ORGANISM: Artificial
<220> FEATURE:
<223> OTHER INFORMATION: Primer

<400> SEQUENCE: 9
gttcatgcct tcttcttttt ccta                                      24

<210> SEQ ID NO 10
<211> LENGTH: 24
<212> TYPE: DNA
<213> ORGANISM: Artificial
<220> FEATURE:
<223> OTHER INFORMATION: Primer

<400> SEQUENCE: 10
ggtttgtcca aactcatcaa tgta                                      24

<210> SEQ ID NO 11
<211> LENGTH: 20
<212> TYPE: DNA
<213> ORGANISM: Artificial
<220> FEATURE:
<223> OTHER INFORMATION: Primer

<400> SEQUENCE: 11
gagctccact tagacggcga                                           20
```

<210> SEQ ID NO 12
<211> LENGTH: 20
<212> TYPE: DNA
<213> ORGANISM: Artificial
<220> FEATURE:
<223> OTHER INFORMATION: Primer

<400> SEQUENCE: 12
caacttccag ggccaggaga                                                     20

<210> SEQ ID NO 13
<211> LENGTH: 22
<212> TYPE: DNA
<213> ORGANISM: Artificial
<220> FEATURE:
<223> OTHER INFORMATION: Primer

<400> SEQUENCE: 13
ggatgtccat attaggacat ct                                                  22

<210> SEQ ID NO 14
<211> LENGTH: 22
<212> TYPE: DNA
<213> ORGANISM: Artificial
<220> FEATURE:
<223> OTHER INFORMATION: Primer

<400> SEQUENCE: 14
ggatgtccat attattacat ct                                                  22

<210> SEQ ID NO 15
<211> LENGTH: 21
<212> TYPE: DNA
<213> ORGANISM: Artificial
<220> FEATURE:
<223> OTHER INFORMATION: Primer

<400> SEQUENCE: 15
acagcacctt caggagatcc a                                                   21

<210> SEQ ID NO 16
<211> LENGTH: 17
<212> TYPE: DNA
<213> ORGANISM: Artificial
<220> FEATURE:
<223> OTHER INFORMATION: Primer

<400> SEQUENCE: 16
tgtggtgcct cgttcca                                                        17

<210> SEQ ID NO 17
<211> LENGTH: 19
<212> TYPE: DNA
<213> ORGANISM: Artificial
<220> FEATURE:
<223> OTHER INFORMATION: Primer

<400> SEQUENCE: 17
tttcggaggt actgggctg                                                      19

<210> SEQ ID NO 18
<211> LENGTH: 21
<212> TYPE: DNA
<213> ORGANISM: Artificial
<220> FEATURE:
<223> OTHER INFORMATION: Primer

```
<400> SEQUENCE: 18
gcattctcct gctgtttcct t                                       21

<210> SEQ ID NO 19
<211> LENGTH: 24
<212> TYPE: DNA
<213> ORGANISM: Artificial
<220> FEATURE:
<223> OTHER INFORMATION: Primer

<400> SEQUENCE: 19
tggattctca aacgtgtcta gtga                                    24

<210> SEQ ID NO 20
<211> LENGTH: 24
<212> TYPE: DNA
<213> ORGANISM: Artificial
<220> FEATURE:
<223> OTHER INFORMATION: Primer

<400> SEQUENCE: 20
ggagaagatc tggcaccata catt                                    24

<210> SEQ ID NO 21
<211> LENGTH: 19
<212> TYPE: DNA
<213> ORGANISM: Artificial
<220> FEATURE:
<223> OTHER INFORMATION: Primer

<400> SEQUENCE: 21
agcagggttg ggtgttcct                                          19

<210> SEQ ID NO 22
<211> LENGTH: 19
<212> TYPE: DNA
<213> ORGANISM: Artificial
<220> FEATURE:
<223> OTHER INFORMATION: Primer

<400> SEQUENCE: 22
gggctgtgtt cccatccat                                          19

<210> SEQ ID NO 23
<211> LENGTH: 23
<212> TYPE: DNA
<213> ORGANISM: Artificial
<220> FEATURE:
<223> OTHER INFORMATION: Primer

<400> SEQUENCE: 23
aggagtcctt ctgacccata cct                                     23

<210> SEQ ID NO 24
<211> LENGTH: 20
<212> TYPE: DNA
<213> ORGANISM: Artificial
<220> FEATURE:
<223> OTHER INFORMATION: Primer

<400> SEQUENCE: 24
caaactgcag cccatgatca                                         20

<210> SEQ ID NO 25
<211> LENGTH: 19
<212> TYPE: DNA
```

```
<213> ORGANISM: Artificial
<220> FEATURE:
<223> OTHER INFORMATION: Primer

<400> SEQUENCE: 25
cggagagtct ggcgagttg                                                    19

<210> SEQ ID NO 26
<211> LENGTH: 20
<212> TYPE: DNA
<213> ORGANISM: Artificial
<220> FEATURE:
<223> OTHER INFORMATION: Primer

<400> SEQUENCE: 26
ggcaagatcc gggatgaaat                                                   20

<210> SEQ ID NO 27
<211> LENGTH: 21
<212> TYPE: DNA
<213> ORGANISM: Artificial
<220> FEATURE:
<223> OTHER INFORMATION: Primer

<400> SEQUENCE: 27
cccaaactcg tctagcttct g                                                 21

<210> SEQ ID NO 28
<211> LENGTH: 20
<212> TYPE: DNA
<213> ORGANISM: Artificial
<220> FEATURE:
<223> OTHER INFORMATION: Primer

<400> SEQUENCE: 28
gttgctgtcc gctctaatca                                                   20

<210> SEQ ID NO 29
<211> LENGTH: 20
<212> TYPE: DNA
<213> ORGANISM: Artificial
<220> FEATURE:
<223> OTHER INFORMATION: Primer

<400> SEQUENCE: 29
tattaggcct catgctgctg                                                   20

<210> SEQ ID NO 30
<211> LENGTH: 23
<212> TYPE: DNA
<213> ORGANISM: Artificial
<220> FEATURE:
<223> OTHER INFORMATION: Primer

<400> SEQUENCE: 30
gctcccataa gacttcatac agc                                               23

<210> SEQ ID NO 31
<211> LENGTH: 20
<212> TYPE: DNA
<213> ORGANISM: Artificial
<220> FEATURE:
<223> OTHER INFORMATION: Primer

<400> SEQUENCE: 31
tttaggagac cttggcttcg                                                   20
```

```
<210> SEQ ID NO 32
<211> LENGTH: 20
<212> TYPE: DNA
<213> ORGANISM: Artificial
<220> FEATURE:
<223> OTHER INFORMATION: Primer

<400> SEQUENCE: 32
ccgttgtgtt tgttgctctt                                              20

<210> SEQ ID NO 33
<211> LENGTH: 20
<212> TYPE: DNA
<213> ORGANISM: Artificial
<220> FEATURE:
<223> OTHER INFORMATION: Primer

<400> SEQUENCE: 33
ttcccaggaa gacattcaca                                              20

<210> SEQ ID NO 34
<211> LENGTH: 20
<212> TYPE: DNA
<213> ORGANISM: Artificial
<220> FEATURE:
<223> OTHER INFORMATION: Primer

<400> SEQUENCE: 34
tttgaaacat gggaagacga                                              20

<210> SEQ ID NO 35
<211> LENGTH: 20
<212> TYPE: DNA
<213> ORGANISM: Artificial
<220> FEATURE:
<223> OTHER INFORMATION: Primer

<400> SEQUENCE: 35
ggcaacctgt ttcaggatct                                              20

<210> SEQ ID NO 36
<211> LENGTH: 20
<212> TYPE: DNA
<213> ORGANISM: Artificial
<220> FEATURE:
<223> OTHER INFORMATION: Primer

<400> SEQUENCE: 36
atcctgaagc tcattgcctt                                              20

<210> SEQ ID NO 37
<211> LENGTH: 20
<212> TYPE: DNA
<213> ORGANISM: Artificial
<220> FEATURE:
<223> OTHER INFORMATION: Primer

<400> SEQUENCE: 37
caattatgct cccaatgacg                                              20

<210> SEQ ID NO 38
<211> LENGTH: 20
<212> TYPE: DNA
<213> ORGANISM: Artificial
<220> FEATURE:
<223> OTHER INFORMATION: Primer
```

```
<400> SEQUENCE: 38
gtgtacagtg cggtgtccaa                                               20

<210> SEQ ID NO 39
<211> LENGTH: 20
<212> TYPE: DNA
<213> ORGANISM: Artificial
<220> FEATURE:
<223> OTHER INFORMATION: Primer

<400> SEQUENCE: 39
gggagaacac ggcatcattg                                               20
```